United States Patent [19]

Ramu

[11] Patent Number: 5,780,446
[45] Date of Patent: Jul. 14, 1998

[54] FORMULATIONS OF VESICANT DRUGS AND METHODS OF USE THEREOF

[75] Inventor: Avner Ramu, Houston, Tex.

[73] Assignee: Baylor College of Medicine, Houston, Tex.

[21] Appl. No.: 700,742

[22] Filed: Jul. 9, 1996

[51] Int. Cl.$^6$ .................... A61K 31/70; A61K 31/525
[52] U.S. Cl. ............................ 514/34; 514/251
[58] Field of Search ........................ 514/34, 251

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,196,281 | 4/1980 | Hearst et al. | 536/28 |
| 4,312,883 | 1/1982 | Baccichetti et al. | 424/279 |
| 4,398,031 | 8/1983 | Bender et al. | 549/282 |
| 4,827,016 | 5/1989 | Morgan | 560/16 |
| 4,906,100 | 3/1990 | Rice et al. | 356/417 |
| 5,047,245 | 9/1991 | Bally et al. | 424/450 |
| 5,049,392 | 9/1991 | Weiner et al. | 424/450 |
| 5,106,951 | 4/1992 | Morgan, Jr. et al. | 530/391.9 |
| 5,171,578 | 12/1992 | Bally et al. | 424/450 |
| 5,212,291 | 5/1993 | Murduck et al. | 536/6.4 |
| 5,216,176 | 6/1993 | Heindel et al. | 549/280 |
| 5,308,874 | 5/1994 | Sanchez et al. | 514/731 |
| 5,356,929 | 10/1994 | Heindel et al. | 514/455 |
| 5,461,080 | 10/1995 | Sanchez et al. | 514/731 |
| 5,468,499 | 11/1995 | Chan et al. | 424/450 |
| 5,475,092 | 12/1995 | Chari et al. | 530/391.7 |

OTHER PUBLICATIONS

Goodman & Gilman's *The Pharmacological Basis of Therapeutics*, 9th ed. (Ed. J.G. Hardman, et al.) (1996) "Chemotherapy of Neoplastic Diseases," MacGraw Hill, New York, pp. 1225–1237, 1242–1243, 1257–1260, 1263–1266.

Rudolph et al. (1976) "Skin Ulcers Due to Adriamycin," *Cancer* 38:1087–1094.

Devita et al., *Cancer: Principles and Practice of Oncology*, 3rd edition, Philadelphia, Lippincott, 1989:2386.

Dorr (1990) "Antidotes to Vesicant Chemotherapy Extravasations," *Blood Rev.* 4:41–60.

Andersson and Dahlstrøm (1993) "Clinical Results After Doxorubicin Extravasation Treated With Excision Guided by Fluorescence Microscopy," *Eur J. Cancer* 29A:1712–1714.

Lichtenstien and Goldman (1970) "Riboflavin–Methotrexate Interactions: Photochemical Reaction and Competition for Transport in the L1210 Mouse Leukemia Cell," *Biochem. Pharmacol.* 19:1229–1239.

Granzow et al. (1995) "Riboflavin–mediated Photosensitization of Vinca Alkaloids Distorts Drug Sensitivity Assays," *Cancer Res.* 55:4837–4843.

Yajima and Mizunoya (1981) "Kinetics of Photoinactivation and Photooxidation of Mitomycin C in the Presence of Riboflavin," *J. Biochem.* 89:929–936.

Sanfilippo et al. (1968) "Photodynamic Action of Daunomycin I –Effect on Bacteriophage T2 and Bacteria," *Giorn. Microbiol.* 16:50.

Verini et al. (1968) "Photodynamic Action of Daunomycin II –Effect on Animal Viruses," *Giorn. Microbiol.* 16:55.

Di Marco et al. (1972) "Interaction of Daunomycin with Nucleic Acids: Effect of Photoirradidiation of the Complex," *Experientia* 28:327–329.

Daugherty et al. (1979) "Direct In Vitro Photoaffinity Labeling of DNA with Daunorobicin, Adriamycin, and Rubidazone," *Biochem. Biophys. Acta* 565:13–21.

Williams and Tritton (1981) "Photoinactivation of Anthracyclines," *Photochem. Photobiol.* 34:131–134.

Gray and Phillips (1981) "Ultraviolet Photoirradiation of Daunomycin And DNA–Daunomycin Complexes," *Photochem. Photobiol.* 33:297–303.

Gray et al. (1982) "Photosensitized Degradation of DNA by Daunomycin," *Photochem. Photobiol.* 36:49–57.

Yee et al. (1984) "Photoaffinity Labeling of the Sarcoma 180 Cell Surface by Daunomycin," *Cancer Res.* 44:1898–1903.

Luedke et al. (1979) "Histopathogenesis of Skin and Subcutaneous Injury Induced by Adriamycin," *Plast. Reconstr. Surg.* 63:463–465.

Hearst (1989) "Photochemistry of the Psoralens," *Chemical Research in Toxicology*, 2:69–75.

Anderson and Vorhees (1980) "Psoralen Photochemotherapy of Cutaneous Disorders," *Ann. Rev. Pharmacol. Toxicol.*, 20:235–257.

Kharasch and Novak (1981) "The Molecular Basis for Complexation of Adriamycin with Flavin Mononucleotide and Flavin Adenine Dinucleotide," *Arch. Biochem. Biophys.* 212:20–36.

Byrom and Turnbull (1967) "Excited States of Flavine Coenzymes–II. Anaerobic Oxidation of Amino Acids by Excited Riboflavine Derivatives," *Photochem. Photobiol.* 6:125–131.

Friedrich (1988) in *Vitamins*, Friedrich, ed., W. de Gruyter, Berlin, pp. 403–471.

Kim et al. (1993) "Photosensitized Formation of Ascorbate Radicals by Riboflavin: An ESR Study," *Photochem. Photobiol.* 57:777–784.

Chinami et al. (1984) "Semiquinone Formation of Adriamycin by Oxidation at para–OH Residue," *Biochem. Int.* 8:299–304.

Silva and Godoy (1994) "Riboflavin Sensitized Photooxidation of Tyrosine," *Int. J. Vit. Nutr. Res.* 64:253–256.

(List continued on next page.)

*Primary Examiner*—Kimberly Jordan
*Attorney, Agent, or Firm*—Medlen & Carroll, LLP

[57] ABSTRACT

The present invention relates to methods of treating, as well as preventing extravasation injury. In particular, the present invention pertains to photochemotherapeutic methods of prophylaxis and/or treatment of extravasation injury induced by vesicant antineoplastic drugs and other pharmaceutical formulations. In accordance with the present invention, extravasation injury is prevented or minimized by the coadministration of photoinactivation inducing compounds in a formulation comprising a vesicant antineoplastic or other pharmaceutical formulation, and subsequently exposing the injection or infusion site to photoexciting light.

41 Claims, 38 Drawing Sheets

OTHER PUBLICATIONS

Brawley et al. (1993) "Hydrogen peroxide generation in a model paediatric parenteral amino acid solution," *Clin. Sci.* 85:709–712.

Rosenfeld et al. (1984) "Fetal and Neonatal Medicine: Prevention of bronchopulmonary dysplasia by administration of bovine superoxide dismutase in preterm infants with respiratory distress syndrome," *J. Pediatr.* 105:781–785.

Ramu et al. (1984) "Reversal of Acquired Resistance to Doxorubicin in P388 Murine Leukemia Cells by Perhexiline Maleate," *Cancer Res.* 44:144–148.

Girotti (1983) "Yearly Review: Mechanisms of Photosensitization," *Photochem. Photobiol.* 38:745–751.

Dorr et al. (1980) "Experimental Model of Doxorubicin Extravasation in the Mouse," *J. Pharmacol. Methods* 4:237–250.

Dorr et al. (1980) "The Limited Role of Corticosteroids in Ameliorating Experimental Doxorubicin Skin Toxicity in the Mouse," *Cancer Chemother. Pharmacol.* 5:17–20.

Averbuch et al. (1986) "Doxorubicin–Induced Skin Necrosis in the Swine Model: Protection With a Novel Radical Dimer," *J. Clin. Oncol.* 4:88–94.

Dahlstrøm et al., "Fluorescence Microscopic Demonstration and Demarcation of Doxorubricin Extravasation," *Cancer* 65:1722–1726 (1990).

Iyengar, "Neural Differentiation As An Expression Of UV Sensitivity," *Acta. Anatomica* 143:236–240 (1981).

Synderman and Krasna, "Adriamycin Extravasation Injuries," *Plastic & Reconstructive Surg.* 77:683–684 (1986).

Braun–Falco et al., *Dermatology* (Springer–Verlag) New York, pp. 1189–1191 (1984).

Dall'Aqua et al., "New Monofunctional Reagents for DNA as Possible Agents for the photochemotherapy of Psoriasis: Derivatives of 4,5'–Dimethylangelicin," *J. Med. Chem.* 24:178–184 (1981).

Hida et al., "Effects Of Antioxidants On Adriamycin–Induced Microsomal Lipid Peroxidation," *Biol. Trace Element Res.* 47:111–116 (1995).

Larson, "Alterations in Wound Healing Secondary to Infusion Injury," *Clinics in Plastic Surgery* 17(3):509–517 (1990).

Lawrence et al., "Topical dimethylsulfoxide may prevent tissue damage from anthracycline extravasation," *Cancer Chemother Pharmacol* 23:316–318 (1989).

Lee et al., Adriamycin Induced Myocardial Dysfunction In Vitro Is Mediated By Free Radicals, *Am. J. Physiol.* 261:H989–H9895 (1991).

Loth and Eversmann, "Treatment Methods For Extravasations Of Chemotherapeutic Agents: A Comparative Study," *J. Hand Surg.* 11:388–396 (1986).

Ludwig et al., "Prevention of Cytotoxic Drug Induced Skin Ulcers With DMSO and Alpha–Tocopherol," *Eur. J. Ca & Clin. Oncol.* 23:327–329 (1987).

Okano et al., "Doxorubicin–Induced Skin Ulcer in the Piglet," *Cancer Treatment Reports* 67(12):1075–1078 (1983).

Rudolph and Larson, "Etiology and Treatment of Chemotherapeutic Agent Extravasation Injuries: A Review," *Journal of Clinical Oncology.* 5(7):1116–1126 (1987).

Soble et al., "Dose–dependent skin ulcers in mice treated with DNA binding antitumor antibiotics," *Cancer Chemother Pharmacol* 20:33–36 (1987).

Speranza et al., "Cells Enriched for Catalase Are Sensitized to the Toxicities of Bleomycin, Adriamycin, and Paraquat," *J. Biol. Chem.* 268:19039–19043 (1993).

Taylor et al., "Glutathione Peroxidase Protects Cultured Mammalian Cells From the Toxicity of Adriamycin and Paraquat," *Arch. Biochem. & Biophysics* 305:600–605 (1993).

Tsavaris et al., "Conservative Approach to the Treatment of Chemotherapy Induced Extravasation," *J. Derm. Surg. & Oncol.* 16:519–522 (1990).

Wang et al., "Effect of Vitamin E Against Adriamycin–Induced Toxicity in Rabbits," *Ca. Res.* 40:1022–1027 (1980).

Miura et al., "Generation of Adriamycin Radical by Interaction with Serum," *Res. Comm. Chem. Path. & Pharmacol.* 71:115–124 (1991).

Ogura et al., "Riboflavin Deficiency Caused By Treatment with Adriamycin," *J. Nutritional Sci. & Vitaminology* 37:473–477 (1991).

Pinto et al., "Adriamycin Induced Increase In Serum Aldosterone Levels: Effects in Riboflavin–Sufficient and Riboflavin–Deficient Rats," *Endocrinology* 127:1495–1501 (1990).

Raiczyk et al., "Enhancement of Adriamycin–Induced Mortality during Riboflavin Administration and Riboflavin Deficiency in Rats," *Proceedings of the Society for Experimental Biology and Medicine* 188:495–499 (1988).

Caffieri et al., "Photocycloaddition of 4,5'–Dimethylangelicin to Cytosine in the Photoreaction with DNA: Isolation of the Adduct," *Medicine Biologie* 11:387–391 (1983).

Dall'Acqua et al., "Monofunctional 3,4' and 4,5'–Photocycloadducts Between 4,5'–Dimethylangelicin and Thymine," *Photochemistry and Photobiology* 37(4):373–379 (1983).

Hearst et al., "The reaction of the psoralens with deoxyribonucleic acid," *Quarterly Review of Biophysics* 17(1):1–44 (1984).

FORMULATIONS OF VESICANT DRUGS AND METHODS OF USE THEREOF

FIELD OF THE INVENTION

The present invention relates to methods of treating and or preventing extravasation injury and more particularly, to photochemotherapeutic methods of prophylaxis and/or treatment of extravasation injury induced by vesicant antineoplastic drugs and pharmaceutical formulations for use therein.

BACKGROUND OF THE INVENTION

Despite the enormous efforts and resources directed at finding a cure, cancer remains an elusive and deadly foe for mankind. The standard methods of treatment usually include chemotherapy, radiation treatment, and surgical removal or tumors and/or growths, or some combination thereof. These treatments, combined with an emphasis on preventative lifestyle modification, have afforded a measure of success in the battle against some cancers. However, cancer remains one of the leading causes of mortality, and cancers detected at matured stages are invariably fatal.

Numerous chemical agents have been devised for the treatment of cancer and they exhibit varying degrees of efficacy. However, no single drug has one hundred percent effectiveness against different cancers, and negative side-effects ranging from minor to serious are always present. Indeed, few medications in common use have a narrower therapeutic index and a greater potential for causing harmful side effects than do antineoplastic drugs.

Most antineoplastic drugs are administered by intravenous injection or infusion. Many of these drugs are vesicants or local irritants and produce severe soft tissue damage upon infiltration or extravasation into tissue surrounding an injection or infusion site. Vesicant compounds include a number of DNA-binding and or DNA-intercalating antineoplastic agents, examples of which include aclarubicin, actinomycin-D (ACT-D), amsacrine (M-AMSA), carmustine (BCNU), bisantrene, cisplatin, dacarbazine, daunorubicin (DAUNO), doxorubicin (DOX), esorubicin (ESO), estramustine phosphate, epirubicin, estoposide, mechloroethamine, mithramycin (MITH), mitoguazone, mitomycin-C, mitoxanthrone, streptozotocin, taxol, teniposide, vinblastine, vincristine, vindesine, zinostatin, and zorubicin [Goodman & Gilman's *The Pharmacological Basis of Therapeutics*, 9th ed. (1996) MacGraw Hill, New York]. Of these, the anthracyclines such as doxorubicin (DOX) are particularly well-known clinically for causing severe tissue necrosis upon paravenous extravasation. Doxorubicin-induced ulcers are unique in their prolonged course with slow healing and their propensity to invade deep structures such as tendons and joints without respect to fascial planes. (Rudolph et al. (1976) *Cancer* 38:1087). Thus, extravasation injury associated with vesicant antineoplastic agents and anthracyclines in particular presents a significant and potentially disabling side effect of cancer therapy.

Apart from measures to prevent paravenous extravasation in the first place, there has been little success with therapeutic compounds or methods to treat or prevent extravasation injury. Purported antidotes such as sodium bicarbonate, corticosteroids, propranolol, isoproterenol, N-acetylcysteine, glutathione, lidocaine, bupivacaine, hyaluronidase, diphenhydramine, cimetidine, alpha-tocopherol, dimethyl sulfoxide, and butylated hydroxytoluene have all been shown to be clinically ineffective. Hyperbaric oxygen, topical heat and cold and excision of the infiltrated tissue have also been tried with either unsatisfactory results and/or significant loss of limb function. [Devita et al., Cancer: *Principles and Practice of Oncology*, 3rd edition, Philadelphia, Lippincott, 1989:2386; Dorr (1990) *Blood Rev.* 4:41; Anderson and Dahlstrom (1993), *Eur J Cancer* 29A: 1712]. The management of extravasations resulting from the intravenous administration of antineoplastic agents continues to be controversial.

Therefore, among the many formidable challenges in treating cancer with antineoplastic drugs is the risk of extravasation injury. Clearly, there remains a need for treatment methods or compounds which minimize, prevent, or eliminate the risk of extravasation injury in humans undergoing treatment with antineoplastic agents.

SUMMARY OF THE INVENTION

The present invention relates to methods of treating and or preventing extravasation injury, and more particularly to photochemotherapeutic methods of treatment of extravasation injury induced by vesicant antineoplastic drugs. In accordance with the present invention, extravasation injury is prevented or minimized by the coadministration of photoinactivation inducing compounds (PIC) such as flavins and photoenhancer compounds in a formulation comprising a vesicant antineoplastic and subsequently exposing the injection or infusion site to long ultraviolet irradiation (UVA) or other photoexciting light. While it is not intended that the present invention be limited by the mechanism by which extravasation injury is prevented or treated, it is believed that anthracyclines are photochemically inactivated upon exposure to UVA light when coadministered with photoinactivating inducing compounds (PIC) such as flavins and photoenhancers (e.g., tyrosine, DABCO, HEPES, etc.). Though flavins are known to induce photoinactivation of a number of compounds, the destructive interaction with anthracyclines was unknown. Further, while photochemical reactions between antineoplastics and visible and ultraviolet light have been described, they have not been described in a photosensitizer or photochemotherapy context. [see, e.g., the following references which discuss: methotrexate: Lichtenstien and Goldman (1970) *Biochem. Pharmacol.* 19:1229; Vinca alkaloids: Granzow et al. (1995) *Cancer Res.* 55:4837; mitomycin C: Yajima and Mizunoya (1981) *J. Biochem.* 89:929 and anthracyclines: Sanfilippo et al. (1968) *Giorn. Microbiol.* 16:50; Verini et al. (1968) *Giorn. Microbiol.* 16:55; Di Marco et al (1972) *Experientia* 28:327; Daugherty et al. (1979) *Biochem. Biophys. Acta* 565:13; Williams and Tritton (1981) *Photochem. Photobiol.* 34:131; Gray and Phillips (1981) *Photochem. Photobiol.* 33:297; Gray et al. (1982) *Photochem. Photobiol.* 36:49; and Yee et al. (1984) Cancer Res. 44:1898]. Therefore, it has been surprisingly found that the use of photosensitizers, in particular flavins, when combined with anthracyclines in a formulation, greatly accelerates the rate of anthracycline inactivation upon exposure to UVA irradiation (i.e., 320–400 nm). Thus, the cytotoxic activity of the anthracyclines is eliminated in localized tissues, thereby eliminating the risk of extravasation injury, while the cytotoxic activity is retained in non-UVA irradiated tissues.

In one embodiment, the present invention provides a method of treatment, comprising: a) providing: i) a subject; and ii) a formulation comprising a photoinactivation inducing compound; and b) administering intravenously said formulation to said subject; and c) exposing the intravenous administration site to UVA light. In a preferred embodiment, the subject is a mammal and in a particularly preferred embodiment, a human. In another preferred embodiment, the formulation further comprises a vesicant chemotherapeutic.

The method of the present invention is not limited by the nature of the chemotherapeutic used. In one embodiment, the chemotherapeutic is an antineoplastic drug. In another embodiment, the antineoplastic drug is an anthracycline or an anthracycline derivative. A particularly preferred anthracycline is doxorubicin. In another embodiment the antineoplastic is a Vinca alkaloid (e.g., vinblastine, vincristine and vindesine).

The present invention is not limited by the photoinactivation inducing compound employed. In one embodiment, the photoinactivation inducing compound is a flavin which is preferably selected from the group consisting of riboflavin, flavin mononucleotide, and flavin adenine dinucleotide.

In a preferred embodiment, the method of the present invention uses a formulation which further comprises at least one photoenhancer compound. The present invention is not limited by the photoenhancer compound chosen. In one embodiment, the photoenhancer compound is a tertiary aliphatic amine, such as 1,4-diazabicyclo(2.2.2)octane. In another embodiment, the photoenhancer compound is a piperazine, such as N-2-hydroxyethylpiperazine-N'-2-ethanesulfonic acid and 1,4-dimethylpiperazine. In a still further embodiment, the photoenhancer compound is selected from the group consisting of tyrosine, tryptophan, histidine, methionine, superoxide dismutase and ethylenediaminetetraacetic acid (EDTA). In another embodiment, the method of the present invention employs a formulation further comprising catalase.

In one embodiment, the present invention provides a method of preventing or treating extravasation injury in a human undergoing intravenous chemotherapy, comprising: a) providing: i) a human subject; and ii) a formulation comprising a vesicant chemotherapeutic and a photoinactivation inducing compound; and b) administering intravenously said formulation under conditions such that said vesicant chemotherapeutic is not inactivated; and c) exposing the intravenous administration site to UVA light under conditions such that a portion of said vesicant chemotherapeutic is photoinactivated. The irradiation is conducted such that the vesicant chemotherapeutic which has extravasated into the tissues surrounding the injection site is photoinactivated but the vesicant chemotherapeutic present in the vessel or at sites of intended therapy is not significantly photoinactivated.

The method of the present invention is not limited by the nature of the chemotherapeutic used. In one embodiment, the chemotherapeutic is an antineoplastic drug. In another embodiment, the antineoplastic drug is an anthracycline or an anthracycline derivative. A particularly preferred anthracycline is doxorubicin. In another embodiment the antineoplastic is a Vinca alkaloid (e.g., vinblastine, vincristine and vindesine).

The present invention is not limited by the photoinactivation inducing compound employed. In one embodiment, the photoinactivation inducing compound is a flavin which is preferably selected from the group consisting of riboflavin, flavin mononucleotide, and flavin adenine dinucleotide.

In a preferred embodiment, the method of the present invention uses a formulation which further comprises at least one photoenhancer compound. The present invention is not limited by the photoenhancer compound chosen. In one embodiment the photoenhancer compound is a tertiary aliphatic amine, such as 1,4-diazabicyclo(2.2.2)octane. In another embodiment, the photoenhancer compound is a piperazine, such as N-2-hydroxyethylpiperazine-N'-2-ethanesulfonic acid and 1,4-dimethylpiperazine. In a still further embodiment, the photoenhancer compound is selected from the group consisting of tyrosine, tryptophan, histidine, methionine, superoxide dismutase and ethylenediaminetetraacetic acid (EDTA). In another embodiment, the method of the present invention employs a formulation further comprising catalase.

The present invention further provides a composition comprising a serum-free saline solution comprising a vesicant chemotherapeutic and a photoinactivation inducing compound. In one embodiment, the saline solution is a 0.9% saline solution (i.e., normal saline). In a preferred embodiment, the composition further comprises dextrose (e.g., 5% dextrose). In still another embodiment, the composition further comprises lactose and/or methylparaben. The compositions of the present invention are not limited by the type of chemotherapeutic employed. In one embodiment, the chemotherapeutic is an antineoplastic drug. In another embodiment, the antineoplastic drug is an anthracycline or an anthracycline derivative. A particularly preferred anthracycline is doxorubicin. In another embodiment, the antineoplastic is a Vinca alkaloid.

The present invention is not limited by the photoinactivation inducing compound employed. In one embodiment, the photoinactivation inducing compound is a flavin which is preferably selected from the group consisting of riboflavin, flavin mononucleotide, and flavin adenine dinucleotide.

In a preferred embodiment, the composition of the present invention further comprises at least one photoenhancer compound. The present invention is not limited by the photoenhancer compound chosen. In one embodiment, the photoenhancer compound is a tertiary aliphatic amine, such as 1,4-diazabicyclo(2.2.2)octane. In another embodiment, the photoenhancer compound is a piperazine, such as N-2-hydroxyethylpiperazine-N'-2-ethanesulfonic acid and 1,4-dimethylpiperazine. In a still further embodiment, the photoenhancer compound is selected from the group consisting of tyrosine, tryptophan, histidine, methionine, superoxide dismutase and EDTA.

In a preferred embodiment, the composition contains the vesicant antineoplastic and the photoinactivation inducing compound in a ratio of between 80:1 and 1:1. In another embodiment, the composition further comprises catalase.

The present invention also provides a composition comprising a vesicant chemotherapeutic, a photoinactivation inducing compound and at least one photoenhancer compound. The composition is preferably serum-free.

The compositions of the present invention are not limited by the type of chemotherapeutic employed. In one embodiment, the chemotherapeutic is an antineoplastic drug. In another embodiment, the antineoplastic drug is an anthracycline or an anthracycline derivative. A particularly preferred anthracycline is doxorubicin. In another embodiment the antineoplastic is a Vinca alkaloid.

The present invention is not limited by the photoinactivation inducing compound employed. In one embodiment, the photoinactivation inducing compound is a flavin which is preferably selected from the group consisting of riboflavin, flavin mononucleotide, and flavin adenine dinucleotide.

In a preferred embodiment, the composition of the present invention further comprises at least one photoenhancer compound. The present invention is not limited by the photoenhancer compound chosen. In one embodiment, the photoenhancer compound is a tertiary aliphatic amine, such as 1,4-diazabicyclo(2.2.2)octane. In another embodiment, the photoenhancer compound is a piperazine, such as N-2-hydroxyethylpiperazine-N'-2-ethanesulfonic acid and 1,4-dimethylpiperazine. In a still further embodiment, the photoenhancer compound is selected from the group consisting of tyrosine, tryptophan, histidine, methionine, superoxide dismutase and EDTA. In another embodiment, the composition further comprises catalase.

DEFINITIONS

Figure 1A:
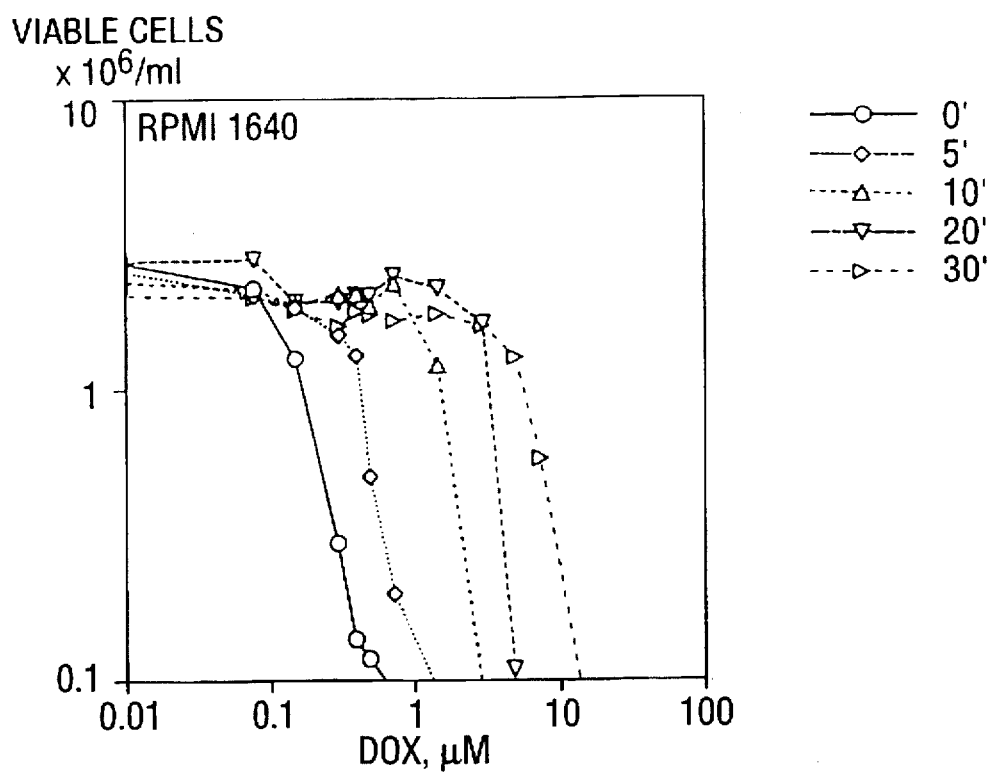
FIGS. 1A and 1B show the effect of the length of UVA irradiation of DOX dissolved in RPMI medium 1640 or in phosphate buffered saline (PBS), respectively on the growth inhibitory effect of the drug on P388 cells.

To facilitate understanding of the invention, a number of terms are defined below.

The term "chemotherapeutic" refers to a compound (i.e., a drug or agent) administered to an animal, including a human, for the treatment of disease, including but not limited to infectious disease and cancer. Chemotherapeutics encompass antibiotics as well as antineoplastics.

The term "antineoplastic" refers to a compound (i.e., a drug or agent) administered to an animal, including a human, for the treatment of cancers or neoplasms.

The term "vesicant chemotherapeutic" refers to chemotherapeutic agents or drugs which are vesicants or local irritants. Vesicant chemotherapeutics produce soft tissue damage which can be severe upon infiltration or extravasation into tissue surrounding an injection or infusion site. Vesicant chemotherapeutics comprise a number of DNA-binding and or DNA-intercalating antineoplastic agents [e.g., aclarubicin, actinomycin-D (ACT-D), amsacrine (M-AMSA), BCNU, bisantrene, cisplatin, dacarbazine, daunorubicin (DAUNO), doxorubicin (DOX), esorubicin (ESO), estramustine phosphate, epirubicin, estoposide, mecloroethamine, mithramycin (MITH), mitoguazone, mitomycin-C, mitoxanthrone, streptozotocin, taxol, teniposide, vinblastine, vincristine, vindesine, zinostatin, and zorubicin].

The term "formulation comprising a vesicant chemotherapeutic" refers to a composition comprising a vesicant chemotherapeutic. The formulation may contain other active compounds such as PICs and photoenhancers as well as inactive compounds such as excipients (e.g., diluents, expanders, binders, carriers, preservatives, stabilizing agents, buffers, etc.).

The term "photosensitizer" as used herein refers to a compound which absorbs light energy and passes it to other molecules which themselves cannot absorb energy at the wavelength(s) of light which excite the photosensitizer.

The term "photoinactivation inducing compounds" is not presently used in the art but is introduced here to describe aspects of the present invention. The terms photoinactivation inducing compounds or "PICs" refer to compounds which when present in a solution containing an anthracycline mediate the UVA-inactivation of the anthracycline. Photoinactivation inducing compounds encompass but are not limited to photosensitizers such as flavins.

The term "light-inactivation of an anthracycline" refers to either 1) a reduction in the growth inhibitory activity of the anthracycline or 2) a decrease in the absorbance of an anthracycline solution following exposure to light. The growth inhibitory activity of an anthracycline is demonstrated by growing cells in culture in medium containing or lacking an anthracycline. A reduction in the ability of the cells to grow in medium containing the anthracycline as compared to growth in the absence of the anthracycline demonstrates the growth inhibitory activity of the anthracycline. The growth of culture cells is conveniently measured by counting the number of viable cells per milliliter of culture medium after a given period of incubation (see, e.g., the assay described in Example 1). In addition, as shown herein, a reduction in the growth inhibitory activity of anthracyclines correlates with structural changes in the anthracycline which may be detected by obtaining the absorbance spectrum (between 350 to 600 nm) of the DOX solution (maximum at 480 nm) (e.g., using the assay described in Example 2). A decrease in the absorbance spectrum of the DOX between 425 and 550 nm reflects light-inactivation of the DOX.

The term "photoenhancer" refers to compounds which enhance or accelerate the PIC-mediated photoinactivation of anthracyclines (e.g., DOX). As shown herein, the presence of a photoenhancer (e.g., DABCO, HEPES, tyrosine, tryptophan, etc.) in an anthracycline solution lacking a PIC has little or no effect on the light photoinactivation of the anthracycline. However, when a photoenhancer is added to a solution containing an anthracycline (e.g., DOX) and a PIC (e.g., a flavin), the light-induced photoinactivation of the anthracycline is greatly enhanced. The addition of a photoenhancer to a formulation containing an anthracycline and a PIC allows either 1) a lower dose of light (e.g., a shorter irradiation time) to be used to inactivate the anthracycline, 2) a lower concentration of PIC to be used to achieve the same level of inactivation of the anthracycline (relative to the concentration of PIC required in the absence of a photoenhancer), 3) or both.

The term "flavin" refers to riboflavin and derivative of riboflavin, including but not limited to FMN and FAD.

The term "piperazine" refers to piperazine (i.e., diethylenediamine) and piperazine derivatives (e.g., N-2-hydroxyethylpiperazine-N'-2-ethanesulfonic acid and 1,4-dimethylpiperazine).

Light plays an important role in many dermatological conditions. This has led to the fields of photobiology, photodiagnosis and phototherapy. Light is one part of the electromagnetic spectrum. The electromagnetic waves from the sun which play a part in photobiological reactions are mainly long ultraviolet light (300–400 nm; UVB and UVA) and visible light (400–760 nm). UV radiation is divided into three wavelength regions, UVC, UVB and UVA, based upon biological-physical factors such as the capacity to induce erythema or melanin pigmentation.

UVA comprises the 320–400 nm wavelength of the electromagnetic spectrum. In small doses, UVA provokes neither erythema nor pigmentation, while in high doses it can cause erythema and immediate pigmentation and in combination with UVB, an intensified erythema. UVA in doses up to 100 J/cm$^2$ does not lead to histologically to phototoxic changes in the epidermis nor to marked dilation of the vessels in the upper dermis. Just as in reontegen therapy, defined units exist for UV radiation: Watt=output or intensity of the lamp; Watt×second=joule (J); and Joule=unit of energy. The unit of dosage, i.e., the energy supplied (J) is given per unit surface area (skin surface): W×sec./cm$^2$=J/cm$^2$.

"Phototoxicity" is a photochemically evoked inflammatory skin reaction in an irradiated region without an immunological basis. The principle of phototoxicity is sued in photochemotherapy or psoralens-UVA (PUVA). While sunburn is caused by a quantitative radiation overdose, the precipitation of a phototoxic reaction requires a photosensitizer in the presence of radiation. Photosensitizers may arise endogenously (e.g., porphyrins) or may be supplied exogenously via the skin, gastrointestinal tract or parenterally (e.g., drugs) and the light can be visible or long ultraviolet.

DESCRIPTION OF THE INVENTION

The present invention relates to improved formulations of vesicant anticancer agents, and more particularly, to novel formulations of anthracyclines especially doxorubicin, such that the side effects of extravasation are reduced or eliminated. The description of the invention is divided into the following sections: (I) Properties of Anthracyclines and Other Vesicant Chemotherapeutic Drugs; (II) Photochemotherapy and Photoinactivation Inducing Compounds; (III) Properties of the Novel Anthracycline Formulations; (IV) Production of Novel Anthracycline Formulations; and (V) Method of Treating or Preventing Extravasation Injury.

I. Properties Of Anthracyclines And Other Vesicant Chemotherapeutic Drugs

The anthracyclines are members of the Rhodomycin group of antibiotics produced by *Streptomyces peucetius* and include doxorubicin, daunorubicin and idarubicin. They have considerable activity against a wide array of tumors, with daunorubicin and idarubicin used primarily in the acute leukemias whereas doxorubicin displays broader activity against human neoplasms, including a variety of solid tumors. The clinical value of these agents is limited by an unusual cardiomyopathy, the occurrence of which is related to the total dose of the drug and is often irreversible.

In a search for agents with high antitumor activity but reduced cardiac toxicity, hundreds of anthracycline derivatives and related compounds have been prepared. Several of these have shown promise in clinical studies, including idarubicin, epirubicin, and the synthetic compound mitoxanthrone, which is an amino anthracendedione [Goodman & Gilman's The Pharmacological Basis of Therapeutics, 9th ed. (1996) MacGraw Hill, New York].

The anthracycline antibiotics have tetracycline ring structures with an unusual sugar, daunosamine, attached by glycosidic linkage. Cytotoxic agents of this class all have quinone and hydroquinone moieties on adjacent rings that permit them to function as electron-accepting and -donating groups (see following structure).

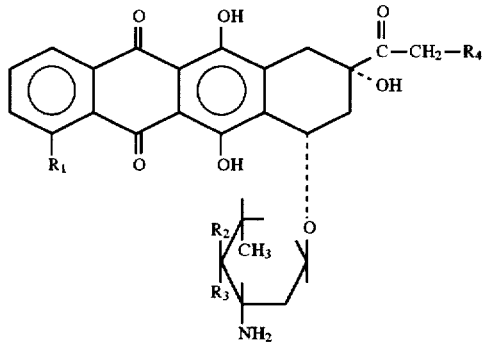

|   | Doxorubicin | Daunorubicin | Epirubicin | Idarubicin |
|---|---|---|---|---|
| $R_1 =$ | $OCH_3$ | $OCH_3$ | $OCH_3$ | H |
| $R_2 =$ | H | H | OH | H |
| $R_3 =$ | OH | OH | H | OH |
| $R_4 =$ | OH | H | OH | H |

Daunorubicin, idarubicin, doxorubicin and analogs of doxorubicin (e.g., mitoxantrone) are usually administered intravenously and are rapidly cleared from the plasma. Recommended dosages comprise, for doxorubicin hydrochloride: 60 to 75 mg/m² administered as a single rapid intravenous (IV) injection at 21 day intervals; for daunorubicin hydrochloride: 30 to 60 mg/m² administered IV daily for 3 days; idarubicin hydrochloride: 12 mg/m² administered IV daily for 3 days; and mitoxantrone: 12 mg/m² administered daily for 3 days.

Toxic manifestations of doxorubicin and daunorubicin are similar. Myelosuppression is a major dose-limiting complication. Stomatitis, gastrointestinal disturbances, and alopecia are common but reversible. Erythematous streaking near the site of infusion (i.e., Adriamycin Flare) is a benign local allergic reaction and is not to be confused with extravasation. The drugs may also produce severe local toxicity in X-ray irradiated tissues (e.g., the skin, heart, lung esophagus, and gastrointestinal mucosa) which may occur even when the two therapies are not administered concomitantly.

Anthracyclines are also members of a larger class of vesicant anticancer agents which includes intercalating antibiotics such as mithramycin; alkylating agents (mitomycin, dibarbazine); and the Vinca alkaloids (vinblastine, vincristine, and vindesine). All vesicant drugs may induce extravasation injury by infiltrating into surrounding tissue at the infusion site. This is characterized histologically by the presence of ischemic necrosis without inflammation, early vascular obliteration and collagen necrobiosis [Luedke et al. (1979) *Plast. Reconstr. Surg.* 63:463].

II. Photochemotherapy And Photoinactivation Inducing Compounds

A. Background

Many proliferative skin diseases (psoriasis, vitiligo, eczema, mycosis fungoides, etc), cancerous conditions (T cell lymphomas), and autoimmune disorders are being treated by the combined utilization of photosensitizing chemicals [applied topically or taken orally] plus UVA and/or UVB. Terms such as photosensitization, photochemotherapy, photopheresis and PUVA (psoralens ultra violet A radiation) are commonly used to refer to special applications of this method. Clinically useful behavior has been found in such chemical families as heme-derived products, porphyrins, phthalocyanins, and psoralens. The oldest and most established phototherapeutics are the psoralens or linear furocoumarins in which three major commercial pharmaceuticals dominate: 8-methoxypsoralen (methoxsalen or 8-MOP); 4,5',8-trimethylpsoralen (trioxsalen or TMP), and 5-methoxypsoralen (5-MOP).

The widely accepted mechanism of action for psoralens is penetration of the target cell's membrane, intercalation into nuclear DNA, and photo-induced bis 2+2 cycloaddition crosslinking of the double helix. Structural and mechanism studies have shown that the 3,4-double bond and the 4',5'-double bond in psoralen form cyclobutane adducts with the double bonds in the pyrimidine bases of DNA. This renders the DNA unable to uncoil and serve as a template for new gene expression. Thus, the target cell is rendered non-viable [Hearst (1989) *Chemical Research in Toxicology*, 2:69; Anderson and Vorhees (1982) *Ann. Rev. Pharmacol. Toxicol.*, 10:177].

However, all of these classes possesses characteristics which makes them less than ideal in the phototherapeutic function: skin staining, suspected mutagenic/carcinogenic properties, poor absorption rates, and systemic toxicity. More importantly, in all of these cases the compounds are not employed to photoinactivate a coadministered pharmaceutical in order to treat or prevent a non-proliferative skin condition such as extravasation but to enhance the therapeutic effect of irradiation of the skin in proliferative skin diseases.

An in vitro screen for phototherapeutics used to treat proliferative skin diseases has been described [e.g., U.S. Pat. No. 5,356,929, the disclosure of which is herein incorporated by reference]. Beneficial phototherapeutics in the treatment of proliferative skin diseases inhibit binding in cells of epithelial origin with epidermal growth factor (EGF). Epidermal growth factor is a low molecular weight polypeptide which binds to cell surface receptors and which is known to be an important regulator of growth in those cells which possess these particular cell surface receptors. Psoriasis, mycosis fungoides, eczema, cancer, and similar proliferative diseases are often characterized by abnormal cell growth regulation which may be related to the action of EGF on the cells in question. Application of PUVA therapy to correct skin disorders, especially psoriasis, is one clinical expression of photochemotherapy. The use of the assay described above was based on the observation that phototherapeutics for proliferative skin diseases are extremely potent inhibitors of binding of epidermal growth factor to cell surface receptors in mammalian cells including humans and that inhibition of this binding arrests the proliferative disorder. In contrast, in the present invention, a class of compounds called photoinactivating inducing compounds (PIC) are defined functionally as those compounds which when coadministered with a chemotherapeutic agent such as an antineoplastic, induce a chemical change in the coadministered chemotherapeutic agent upon exposure to light, such that the chemotherapeutic agent loses its cytotoxic effect.

B. Photochemical Reactions

Photochemical reactions between antineoplastic compounds and light (visible and ultraviolet) have been described |methotrexate (Lechtenstein and Goldman, 1970 Biochem. Pharmacol., 19:1229), Vinca alkaloids (Granzow et al. 1995, Cancer Res., 55:4837), mitomycin C (Yajima and Mizunoya, 1981, J Biochem., 89:929) and anthracycline (Sanfilippo et al., 1968, Giorn. Microbiol., 16:50; Verini et al., 1968, Giorn. Microbiol., 16:55; Di Marco et al., 1972, Experientia, 28:327; Daugherty et al., 1979, Biochem. Biophys. Acta., 565:13; Williams and Tritton, 1981, Photochem. Photobiol., 34:131; Gary and Phillips, 1981, Photochem. Photobiol., 33:297; Gary et al., 1982, Photochem. Photobiol., 36:49; Yee et al., 1984, Cancer Res. 44:1898)|. The majority of this literature teaches that light enhances the binding of anthracyclines to DNA and membranes; such an enhancement would be beneficial if it occurred at the intended site of treatment (i.e., the tumor) and detrimental if it occurred elsewhere in the body.

Williams and Tritton report that the cytotoxic activity of anthracyclines is reduced in vitro as a result of long ultraviolet (UVA) irradiation |(1991) Photochem. Photobiol. 34:131|. The half-time for inactivation of doxorubicin or daunomycin by two 15 W tubes emitting 365 nm light was reported to be 9 hours (Williams and Tritton, supra). The length of time required to inactivate anthracyclines under the conditions reported by Williams and Tritton is too long to be practical for clinical applications. Furthermore, Williams and Tritton do not suggest that photoinactivation may be used therapeutically to prevent the cytotoxic activity of doxorubicin at undesired sites and the use of photosensitizers (e.g., flavins) to enhance photoinactivation of anthracyclines is not described.

The present invention demonstrates that PICs, such as the flavins, greatly accelerate the rate of inactivation of antineoplastic compounds (e.g., anthracyclines) by UVA irradiation in a localized manner when co-administered within a formulation containing the antineoplastic compound. Using the methods and compositions of the present invention, the cytotoxic activity of anthracyclines is eliminated locally, thereby avoiding the risk of extravasation injury, while retaining the desirable systemic cytotoxic activity in non-UVA irradiated tissues.

III. Properties Of The Novel Anthracyclines Formulations

The present invention provides novel formulations for in vivo administration comprising vesicant chemotherapeutics (e.g., anthracyclines) and PICs. The presence of the PIC in the chemotherapeutic formulation allows the treatment of extravasation injury caused by the vesicant chemotherapeutic. Sites of extravasation are irradiated with long wavelength ultraviolet light (i.e., 320–400 nm). The presence of the PIC in the chemotherapeutic formulation mediates the photoinactivation of the vesicant chemotherapeutic in the tissues surrounding the injection site.

The present invention demonstrates that chemotherapeutics (e.g., anthracyclines such as doxorubicin) can be inactivated by exposure to UVA light (i.e., photoinactivated) when a PIC is present in solution with the chemotherapeutic. Chemotherapeutic drugs are toxic to cells. Placing cultured cells in a medium containing a chemotherapeutic drug results in a reduced rate of cell growth or an inhibition of cell growth. As shown herein, the growth inhibitory activity of chemotherapeutic drugs, such as anthracyclines, is not appreciably diminished by exposure of the drug to doses of UVA light typically used in a clinical setting. However, exposure of vesicant chemotherapeutics (e.g., anthracyclines such as DOX) to UVA light in the presence of a PIC causes photoinactivation of the anthracycline which results in a reduction in the growth inhibitory activity of the chemotherapeutic. A reduction in the growth inhibitory activity of chemotherapeutic drugs, such as anthracyclines, was shown herein to correlate with structural changes in the drug which are reflected in a decrease in the absorbance spectrum of the drug.

As shown herein, the effects of UVA light on the cell growth inhibitory activity of anthracyclines (e.g., DOX) cell growth inhibitory activity and absorbance spectrum are dependent on the composition of the solution. When the drug was dissolved in PBS, its cell growth inhibitory activity could not be reduced by exposing it, in nmol quantities dissolved in a 1 mm thick solution, to 20 joules of UVA energy. However, in RPMI medium 1640 this irradiation energy was sufficient to destroy about 90% of the drug activity. When 60 nmol of DOX dissolved in a 3.75 mm thick layer of RPMI medium 1640 were exposed to 80 joules of UVA, the drug absorbance between 425 and 550 nm was reduced to background level. When DOX was dissolved in a solution that contained only the inorganic salts of RPMI medium 1640 or in PBS, this UVA energy had only a minor effect on the drug absorbance spectrum. To determine which of the 40 components of the RPMI medium 1640 mediate the effect of UVA irradiation on DOX, studies were carried out in solutions that contained only some of the medium components. These studies revealed that the major mediator of the effect of UVA on DOX was riboflavin, a known photosensitizer.

The present invention also demonstrates that other naturally occurring flavins, such as FMN and FAD, also mediate the effect of UVA on DOX. Although FMN was as effective as riboflavin, the FAD concentration had to be raised 5 fold to obtain a comparable effect. The lower efficacy of FAD in mediating the effect of UVA on DOX may be related to its lower ability to associate with DOX than with riboflavin or FMN |Kharasch and Novak (1981) Arch. Biochem. Biophys. 212:20|.

It is known that flavins, excited by 365 nm light, can undergo photoreduction while oxidizing certain substrates |Byron and Turnbull (1967) Photochem. Photobiol. 6:125|. While not limiting the present invention to any particular mechanism, the changes in the cell growth inhibitory activity and in the absorbance spectrum of DOX after UVA irradiation in the presence of flavins may reflect oxidation of the drug. This possibility is supported by the following observations which are described herein. In the presence of ascorbate (without DOX), UVA-irradiated riboflavin lost its 400 to 500 nm absorbance maximum at a faster rate than that measured in the absence of this reducing agent. It is known that riboflavin in its oxidized state has two absorbance maxima at 360 and 445 nm, while its reduced form shows only the first absorbance maximum [Friedrich (1988) in Vitamins, Friedrich, ed., W. de Gruyter, Berlin, pp. 403–471]. The increased rate of loss of riboflavin absorbance at 445 nm when irradiated with UVA in the presence of ascorbate indicated that the photo-excited riboflavin is reduced at a faster rate in the presence of oxidizable substrate (ascorbate). In the presence of DOX, UVA-irradiated riboflavin also lost its 400 to 500 nm absorbance maximum at a faster rate than that measured in the absence of DOX. Therefore, the facilitating effect of DOX on the rate of decrease in riboflavin absorbance at 445 nm under UVA could also reflect an increased rate of reduction of the photo-excited riboflavin because of the availability of oxidizable substrate (DOX). In addition, the relative efficacies of riboflavin, FMN and FAD in mediating the effect of UVA on DOX described herein are similar to those reported previously for their relative abilities to photooxidize ascorbate [Kim et al. (1993) Photochem. Photobiol. 57:777]. This similarity further supports the idea that DOX is photooxidized by UVA and flavin. The observation that a reducing agent, ascorbic acid (1.6 mM), blocked the changes occurring in the absorbance spectrum of DOX (20 μM) when irradiated in the presence of 20 μM riboflavin could be interpreted as a competition between oxidizable substrates for the limited availability of an oxidizing agent (e.g., the UVA excited riboflavin). Although it is not yet certain whether DOX is indeed oxidized by UVA and riboflavin, it was previously shown that it could undergo oxidation [Chinami et al. (1984) Biochem. Int. 8:299]. Alternatively, the effect of UVA and riboflavin on DOX may involve other chemical reactions, e.g., polymerization. DOX polymers were previously obtained, with a very low quantum efficiency, by irradiating DOX with UVA in the absence of a photosensitizer [Williams and Tritton, supra].

In the presence of a photosensitizer, the only amino acids that are known to be affected by UVA irradiation at an appreciable rate are: histidine, methionine, tryptophan and tyrosine [Gollnik (1975), supra]. The photosensitizing effect of riboflavin was indeed greatly enhanced in the presence of these (and not the other) amino acids in concentration as in RPMI medium 1640. The mechanism by which histidine, methionine, tryptophan and tyrosine enhance the UVA and riboflavin effect on DOX is not known. Light excited riboflavin was shown to interact directly with certain amino acids, such as tyrosine [Silva and Godoy (1994) Int. J Vit. Nutr. Res. 64:253], and it was also reported that hydrogen peroxide could be generated in a mixture of amino acids and riboflavin exposed to light [Brawley et al. (1993) Clin. Sci. 85:709]. This raised the possibility that the hydrogen peroxide was involved in the destruction of DOX. However, as described herein, DOX dissolved in a solution of RPMI medium 1640 inorganic salts, vitamins and amino acids was not protected by catalase from the effect of UVA, it seems to be an unlikely possibility. These results are in accordance with a previous study that found that the riboflavin-sensitized photooxidation of ascorbate also did not involve hydrogen peroxide [Kim et al., (1993) Photochem. Photobiol. 57:777].

The present invention also provides novel formulations comprising anthracyclines, PICs and photoenhancers. Photoenhancers are defined as compounds which enhance or accelerate the PIC-mediated photoinactivation of anthracyclines (e.g., DOX). As shown herein, the presence of a photoenhancer (e.g., DABCO, HEPES, tyrosine, tryptophan, superoxide dismutase, EDTA, etc.) in an anthracycline solution lacking a PIC has little or no effect on the UVA photoinactivation of the anthracycline. However, when a photoenhancer is added to a solution containing an anthracycline (e.g., DOX) and a PIC (e.g., a flavin)anthracycline is greatly activation of the anthracycline is greatly enhanced. The addition of a photoenhancer to a formulation containing an anthracycline and a PIC allows either 1) a lower dose of UVA (e.g., a shorter irradiation time) to be used to inactivate the anthracycline, 2) a lower concentration of PIC to be used to achieve the same level of inactivation of the anthracycline (relative to the concentration of PIC required in the absence of a photoenhancer), 3) or both.

IV. Production Of Novel Anthracycline Formulations

The present invention demonstrates that anthracyclines (e.g., DOX) in solution can be chemically changed with a concomitant loss of growth inhibitory activity and change in absorbance spectrum by long ultraviolet light UVA at intensities that are used clinically. To obtain this effect, the anthracycline is combined in a formulation with a photoinactivation inducing compounds (PICs) (e.g., flavins such as riboflavin, FMN, FAD). In some embodiments, the anthracycline (e.g., DOX) is combined with a flavin at molar quantity ratios of 1:80 to 1:1 flavin:DOX, with:

a) 1:50 to 1:500 DOX:DABCO molar ratio (or other tertiary aliphatic amines); or b) 1:50 to 1:500 DOX:HEPES molar ratio (or other piperazines); or c) 1:1 to 1:6 DOX:tyrosine or tryptophan molar ratio (histidine, methionine, or EDTA may be used in place of tyrosine or tryptophan) and with 1:50 to 1:500 DOX:piperazine.

As it was reported that hydrogen peroxide may be formed when amino acids are exposed to UVA in the presence of photosensitizers [Brawley et al. (1993) Clin. Sci. 85:709], catalase is added to the formulation in some embodiments in order to protect the tissue from hydrogen peroxide that may be formed when a solution of flavin and amino acids are exposed to UVA. In addition, oxygen radicals may be by-products of the photoinactivation reaction (i.e., the UVA-mediated destruction of anthracycline in the presence of PICs and/or photoenhancers). Accordingly, superoxide dismutase (SOD) is added to the formulation in some embodiments to protect the UVA irradiated tissue from damage due to the generation of oxygen radicals. In addition to protecting tissue from oxygen radicals, as shown herein, SOD further acts as a photoenhancer and accelerates the UVA-mediated destruction of anthracyclines (Ex. 9, infra).

Recombinant human CuZn superoxide dismutase is available from Bio-Technology General Corp. (Iselin, N.J.) and has been approved by the FDA (IND 28,225) for use in clinical trials. Bovine superoxide dismutase has been administered subcutaneously to humans (premature infants) at a dose of 0.26 mg/kg [Rosenfeld et al. (1984) J Pediatr. 105:781].

V. Method Of Treating Or Preventing Extravasation Injury

The present invention contemplates using therapeutic formulations of chemotherapeutics, such as anthracyclines, photoinactivation inducing compounds (PICs), photoenhancing compounds and hydrogen peroxide degrading agents (e.g., catalase). It is not intended that the present invention be limited by the particular nature of the therapeutic preparation. For example, such compositions can be provided together with physiologically tolerable liquid, gel or solid carriers, diluents, adjuvants and excipients. In addition, the formulations may be combined other antineoplastic agents, including other vesicant drugs such as the Vinca alkaloids. Formulations for such administrations may comprise an effective amount of a vesicant anticancer drug in combination with an effective amount of PICs and/or photoenhancers in sterile water or physiological saline.

On the other hand, formulations may contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The compositions are preferably prepared as injectables, either as liquid solutions or suspensions; solid forms suitable for solution in, or suspension in, liquid prior to injection may also be prepared.

The vesicant drug/photoinactivation inducing compound/photoenhancer combinations of the present invention are often mixed with diluents or excipients which are compatible and physiologically tolerable. Suitable diluents and excipients are, for example, water, saline, dextrose, lactose, glycerol, or the like, and combinations thereof. In addition, if desired the compositions may contain minor amounts of auxiliary substances such as wetting or emulsifying agents, stabilizing or pH buffering agents.

EXPERIMENTAL

The following examples serve to illustrate certain preferred embodiments and aspects of the present invention and are not to be construed as limiting the scope thereof.

In the experimental disclosure which follows, the following abbreviations apply: DOX [Doxorubicin HCl (Adriamycin RDF)]; EDTA (ethylenediaminetetraacetic acid); PBS (Dulbecco's phosphate buffered saline); HCl (hydrogen chloride); NaCl (sodium chloride); HEPES ((N-[2-hydroxyethyl] piperazine-N'-[2-ethanesulfonic acid])); µl (microliters); µg (micrograms); ml (milliliters); L (liters); mg (milligrams); g (grams); hr (hours); mM (millimolar); µM (micromolar); nM (nanomolar); N (normal); nm (nanometers); min (minutes); sec (seconds); IU (international units); s.c. (subcutaneous); mm (millimeter); MTD (maximally tolerated dosage); i.p. (intraperitoneal); kg (kilograms); UV (ultraviolet); UVA (long ultraviolet light); VIS (visible); W (watt); GibcoBRL (GibcoBRL, Gaithersburg, Md.); Sigma (Sigma Chemical Co., St. Louis, Mo.)

Riboflavin, flavin mononucleotide (FMN), flavin adenine dinucleotide (FAD), ascorbic acid and catalase (2200 units/mg protein) were purchased from Sigma. RPMI medium 1640, RPMI medium 1640 without riboflavin, RPMI medium 1640 without phenol red, Dulbecco's phosphate-buffered saline (PBS) and HEPES buffer solution were purchased from GibcoBRL. RPMI medium 1640 Select-Amine Kit, which contained: a) 4× concentrate of inorganic salt mixture ($Ca^{2+}(NO_3)_2.4H_2O$ 400 mg/L, KCl 1600 mg/L, $MgSO_4$ 195.36 mg/L, NaCl 24000 mg/L); b) 100× concentrate of vitamin mixture (Biotin 20 mg/L, D-$Ca^{2+}$ pantothenate 25 mg/L choline-Cl 300 mg/L, folic acid 100 mg/L, i-inositol 3500 mg/L, niacinamide 100 mg/L, p-aminobenzoic acid 100 mg/L, pyridoxine.HCl 100 mg/l, riboflavin 20 mg/L, thiamine.HCl 100 mg/L vitamin $B_{12}$ 0.5 mg/L and reduced glutathione 100 mg/L); and c) 100× concentrate of amino acid mixture (1-arginine 20000 mg/L, 1-asparagine 5000 mg/L, 1-aspartic acid 2000 mg/L, 1-cystine 5000 mg/L, 1-glutamic acid 2000 mg/L, 1-glutamine 30000 mg/L, glycin 1000 mg/L, 1-histidine 1500 mg/L, 1-hydroxyproline 2000 mg/L, 1-isoleucine 5000 mg/L, 1-leucine 5000 mg/L, 1-lysine.HCl 4000 mg/L, 1-methionine 1500 mg/l, 1-phenylalanine 1500 mg/L, 1-proline 2000 mg/L, 1-serine 3000 mg/L, 1-threonine 2000 mg/L, 1-tryptophan 500 mg/L, 1-tyrosine 2000 mg/L and 1-valine 2000 mg/L) was purchased from GibcoBRL. Doxorubicin HCl (Adriamycin RDF) was purchased from Farmitalia Carlo Erba (Milan, Italy).

EXAMPLE 1

In Vitro Cell Culture Assay For Monitoring The Photoinactivation Of Anthracyclines An in vitro assay was employed which allows for the rapid screening of various formulations for their ability to enhance UVA-mediated inactivation of anthracyclines. Application of solutions containing anthracyclines to the culture medium of cells causes an inhibition of the growth of the cells (i.e., the anthracyclines are cytotoxic). The growth inhibitory activity of anthracyclines was found to be reduced by exposure of the anthracycline solution to long ultraviolet light (UVA) prior to the addition of cultured cells. The reduction in growth inhibitory activity was found to correlate with a decrease in the absorbance spectrum of the anthracycline (e.g., doxorubicin) (described in Example 2). This in vitro assay permits the rapid screening of compounds for the ability to enhance the photoinactivation of anthracyclines by UVA irradiation. The in vitro assay is illustrated below using the P388 cell line; however, any mammalian cell line can be employed.

a) Cell Culture

Cell culture was carried out as previously described [Ramu et al. (1984) *Cancer Res.* 44:144]. Briefly, P388 murine leukemia cells (i.e., $P388D_1$ available from the ATCC; ATCC CCL 46) were maintained in RPMI medium 1640 supplemented with 10% fetal calf serum (FCS), penicillin base (50 units/ml) and streptomycin (50 µg/ml) (all from GibcoBRL) and 10 µM 2-mercaptoethanol (Sigma) (herein after "complete culture medium"). An inoculum of cells was transferred to fresh medium once every 4 days to maintain exponential growth. Four days after the seeding of $1\times10^5$ viable cells/ml, cell growth was assessed by measurements of cell density in a Coulter Counter with multisizer (Coulter Electronics Ltd., Beds, England). Sensitivity to DOX was assessed by culturing the cells in 24 well cell culture clusters (Costar, Cambridge, Mass.) in a volume of 1 ml/well with various drug concentrations and by measuring cell density 4 days later.

b) Long Ultraviolet (UVA) Light Exposure

Various concentrations of DOX were dissolved in RPMI medium 1640 or other solutions described infra (referred to as drug solutions or DOX solutions). Drug solutions (0.2 ml/well) in 24 well culture clusters without the lid were irradiated in a laminar flow hood with 3 Blacklight Blue 40 W lamps (Vilber Lourmat, Marne la Vallee, France). The energy flow rate delivered to the DOX solutions was 5 to 6 $mW/cm^2$ as measured with a Cole-Parmer 97503-00 Radiometer (Niles, Ill.) with a 365 nm sensor. The hood air flow was found to be sufficient to prevent warming of the irradiated solutions throughout the length of the experiments. After the exposure of the DOX solutions to UVA, $1\times10^5$ viable cells in 0.8 ml of the complete culture medium were added to each well, and the cell density was measured after 4 days of culture.

FIG. 1 shows the effect of the length of UVA irradiation of DOX, dissolved in RPMI medium 1640 or in PBS, on the growth inhibitory effect of the drug on P388 cells that were added after the irradiation of the drug solution. For the results shown in FIG. 1A, various concentrations of DOX (0.01, 0.1, 1.0, 10 or 100 µM), dissolved in 0.2 ml of RPMI medium 1640, were placed in the wells of a 24 well culture plate and the plate was exposed to UVA for 0, 5, 10, 20 or 30 minutes as described above. P388 cells were then added to each well ($1\times10^5$ viable cells in 0.8 ml of complete culture medium) and the plates were incubated for 4 days. Following the incubation, the density of the cells in each well was determined.

Figure 1B:
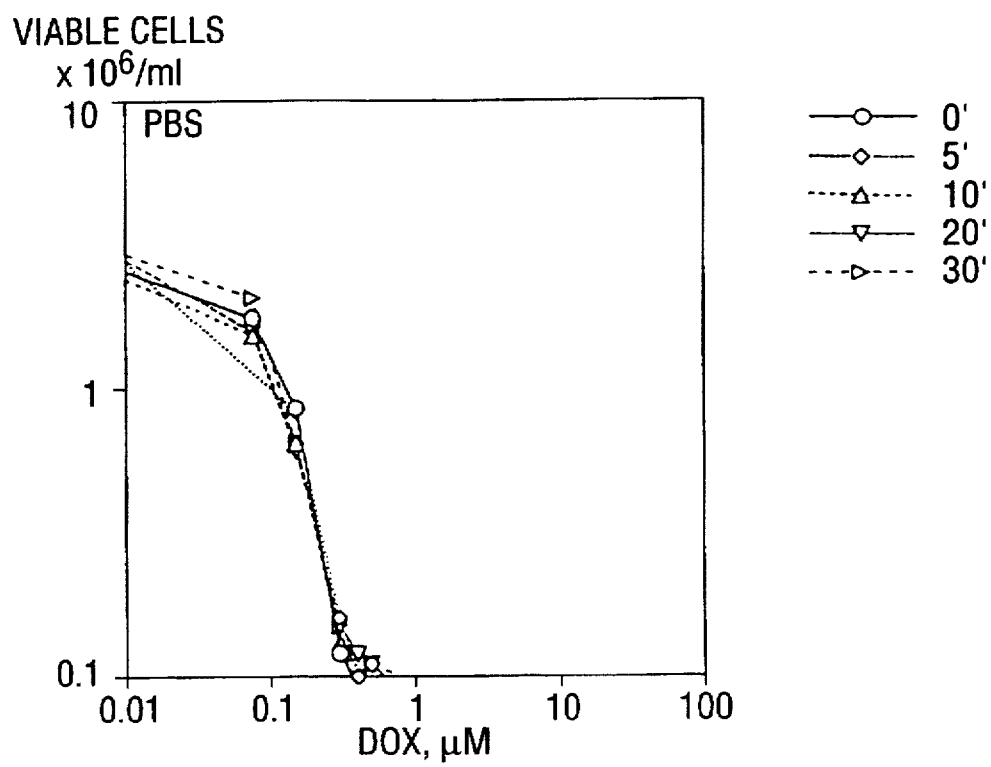
Figure 2A:
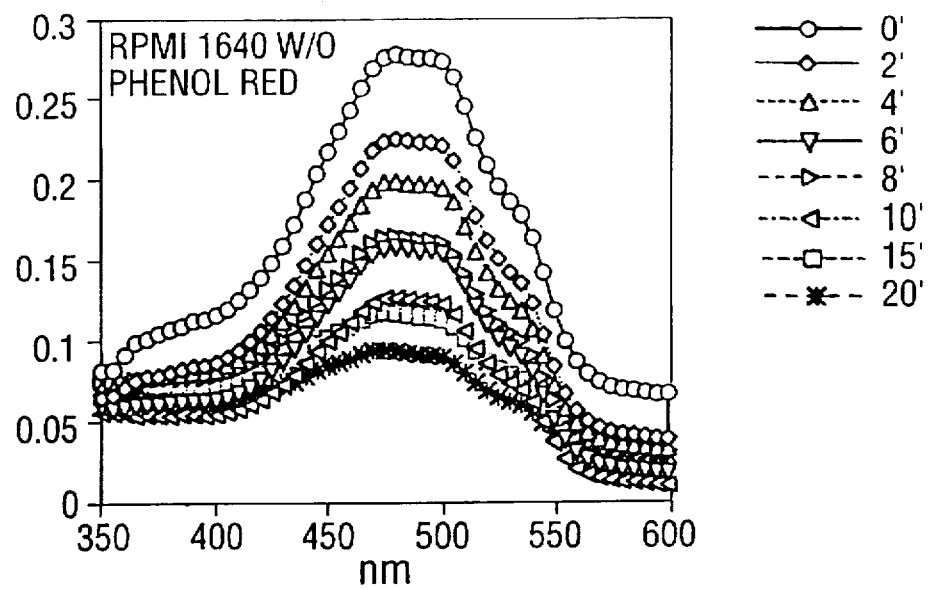
FIGS. 2A–2F show the effect of length of UVA irradiation of 20 µM DOX in various media with 50 mM HEPES (pH=7.2) on the absorbance spectrum of DOX.
Figure 2B:
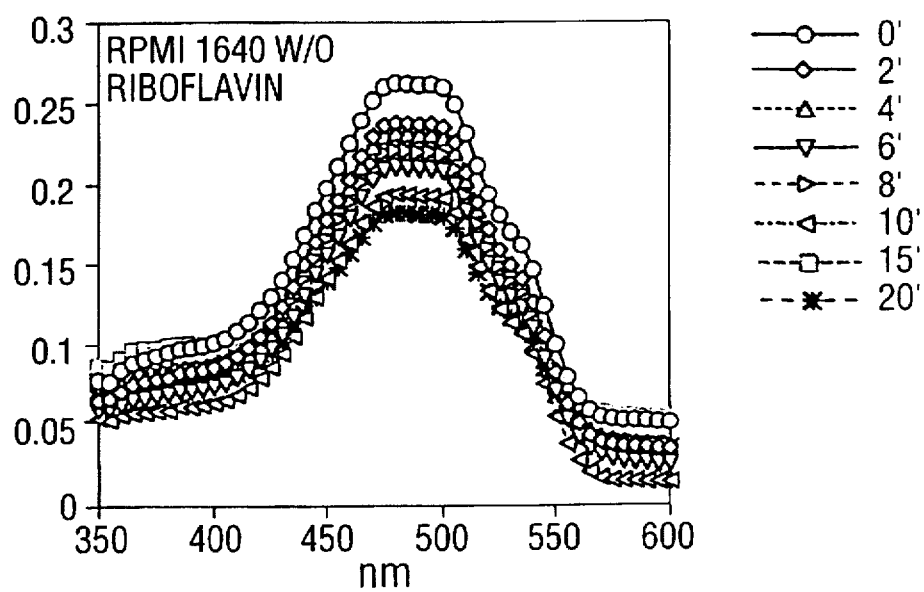
Figure 2C:
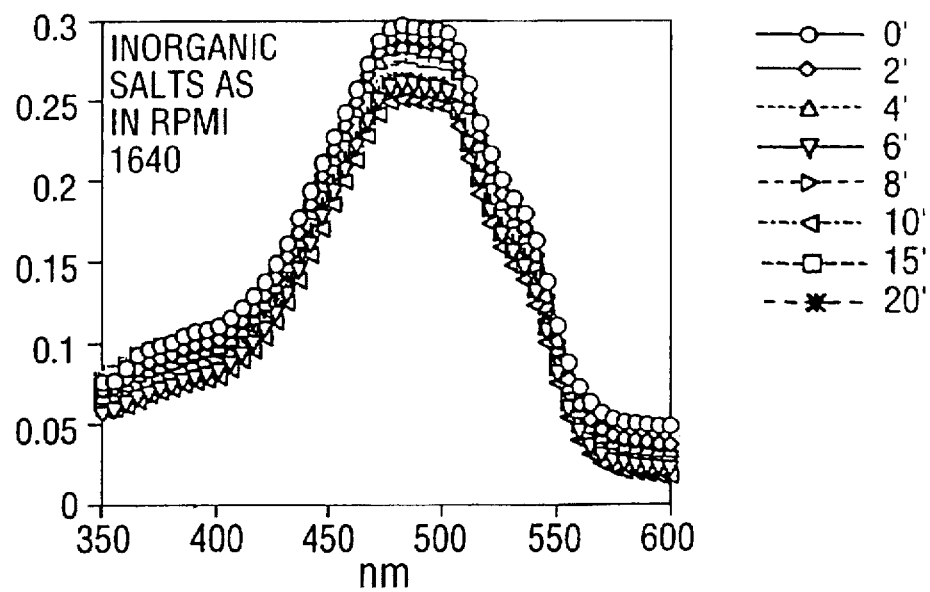
Figure 2D:
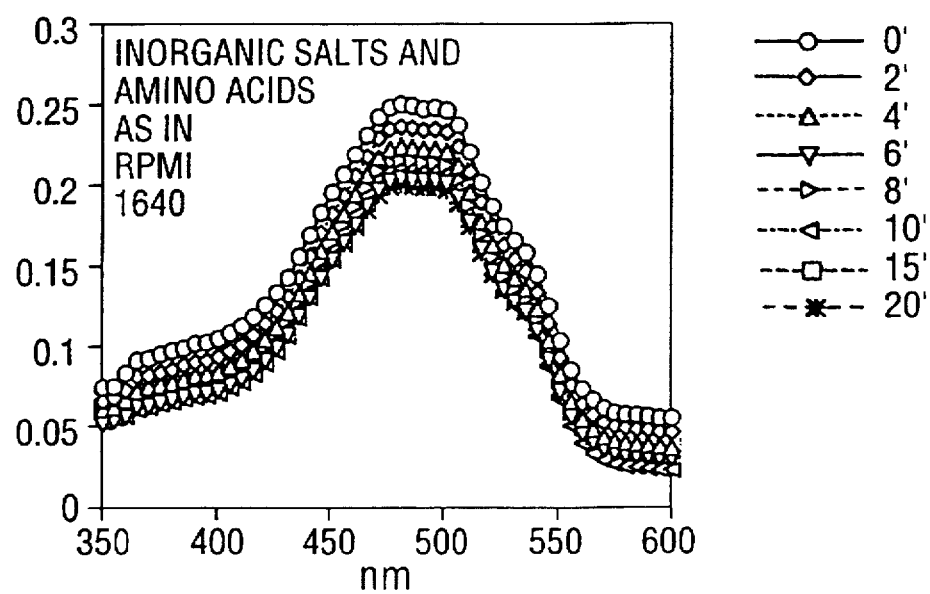
Figure 2E:
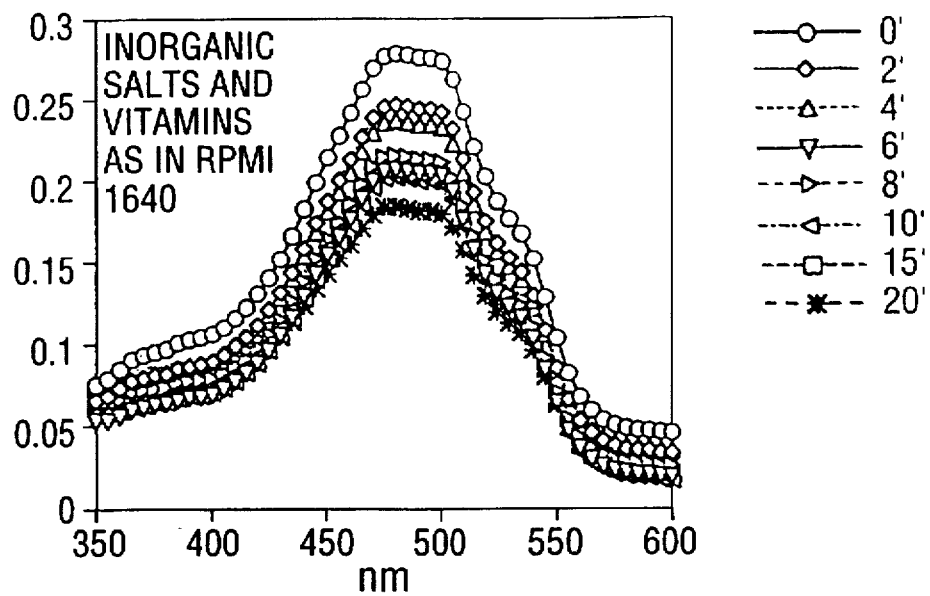
Figure 2F:
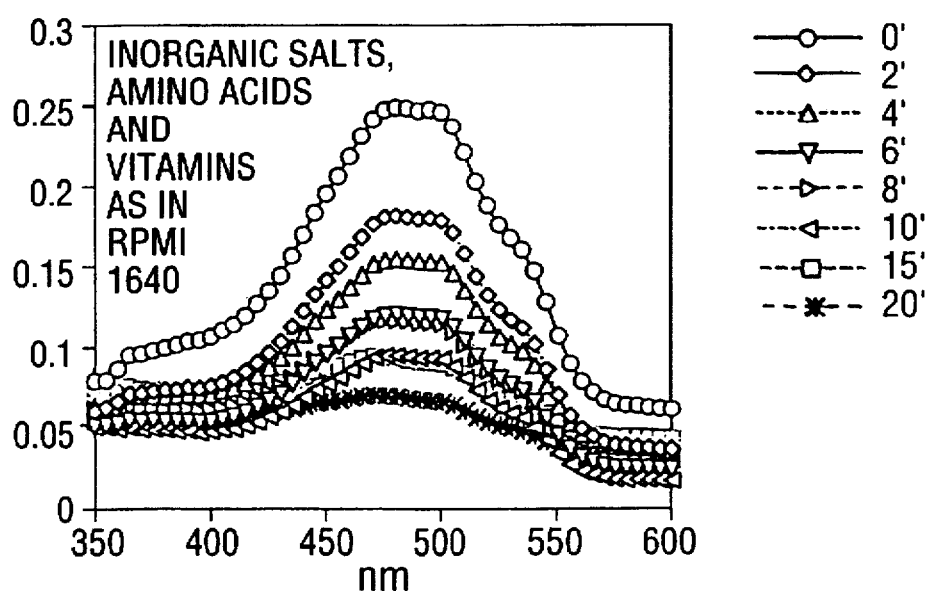

The results shown in FIG. 1B were obtained as described for FIG. 1A with the exception that the DOX was dissolved in PBS rather than RPMI medium 1640 prior to irradiation.

The results shown in FIG. 1 demonstrated that irradiating DOX in PBS for up to 30 minutes did not affect the growth inhibitory effect of the drug, but irradiating DOX in RPMI medium 1640 resulted in a decrease of the drug activity that was proportional to the length of irradiation. When RPMI medium 1640 was irradiated prior to adding the drug, no reduction in the growth inhibitory effect was observed; this suggested that if the UVA activated some component(s) of the RPMI medium 1640 that could inactivate the drug, this component decayed rapidly and did not affect the DOX that was added later. Replacing the standard RPMI medium 1640 with RPMI medium 1640 without phenol red did not affect the results, indicating that the dye did not participate in the drug inactivation process.

EXAMPLE 2

Effect of Long Ultraviolet Light Irradiation On The Absorbance Spectrum of Doxorubicin The results shown above demonstrated that UVA irradiation ameliorated the growth inhibitory activity of DOX. In order to investigate whether this photoinactivation reflected structural changes in the DOX molecule, the following experiments were conducted.

a) Spectral Measurements

Three milliliters of 20 µM DOX solutions were placed in 35 mm open cell culture dishes and irradiated with UVA in a laminar flow hood for up to 20 min. (as described above). After the irradiation, the 350 to 600 nm absorbance spectra were measured in a double beam UV-VIS scanning spectrometer (Shimadzu Scientific Instruments Inc., Columbia, Md.). In some experiments, to deplete the dissolved oxygen, the drug solutions were bubbled with nitrogen for 10 min prior to and through the length of exposure to UVA. The DOX absorbance (measured at 480 nm) decayed exponentially over the length of the UVA irradiation time. The first order rate constant of the decrease in DOX absorbance ($K_{DOX}$) was calculated. In repeated experiments, the standard deviation of this parameter was consistently <17% of the mean value.

b) Exposure To Long Ultraviolet Light Effects The Absorbance Spectrum Of Doxorubicin Because the reduction in the DOX growth inhibitory activity by UVA irradiation may reflect structural changes in the DOX molecule, the effect of UVA irradiation on the absorbance spectrum of DOX was studied. The results are summarized in FIGS. 2 and 3.

In FIGS. 2 and 3, various solutions containing 20 µM DOX and 50 mM HEPES (pH 7.2) was irradiated for 0, 2, 4, 6, 8, 10, 15 or 20 minutes and the absorbance between 350–600 nm was measured. FIG. 2A shows the absorbance spectra obtained when DOX was dissolved in RPMI medium 1640 without phenol red. FIG. 2B shows the absorbance spectra obtained when DOX was dissolved in RPMI medium 1640 without riboflavin. FIG. 2C shows the absorbance spectra obtained when DOX was dissolved in a solution containing the inorganic salts found in RPMI medium 1640. FIG. 2D shows the absorbance spectra obtained when DOX was dissolved in a solution containing the 20 amino acids and inorganic salts found in RPMI medium 1640. FIG. 2E shows the absorbance spectra obtained when DOX was dissolved in a solution containing the vitamins and inorganic salts found in RPMI medium 1640. FIG. 2F shows the absorbance spectra obtained when DOX was dissolved in a solution containing the vitamins, 20 amino acids and inorganic salts found in RPMI medium 1640.

Figure 3A:
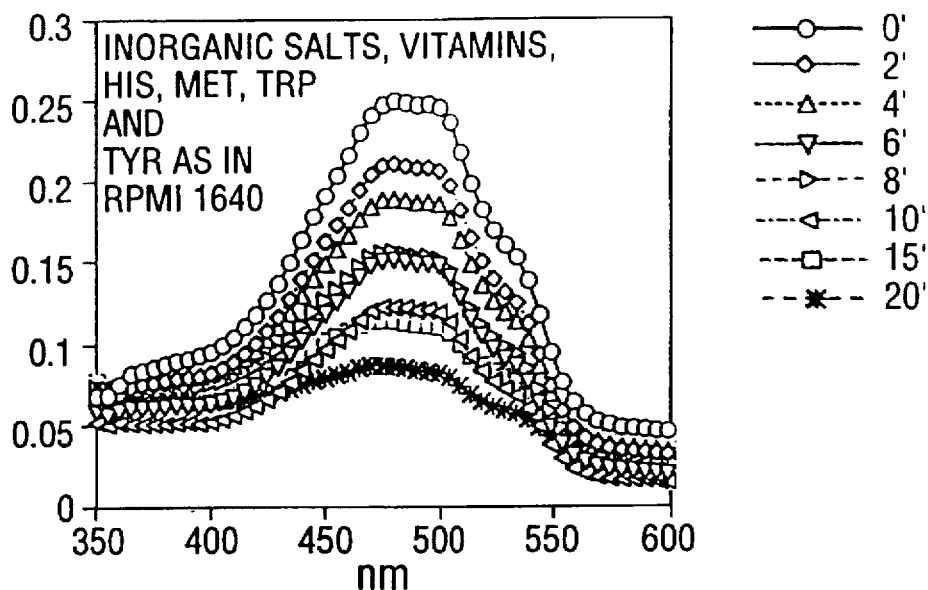
FIGS. 3A–3F show the effect of length of UVA irradiation of 20 µM DOX in various media with 50 mM HEPES (pH=7.2) on the absorbance spectrum of DOX.
Figure 3B:
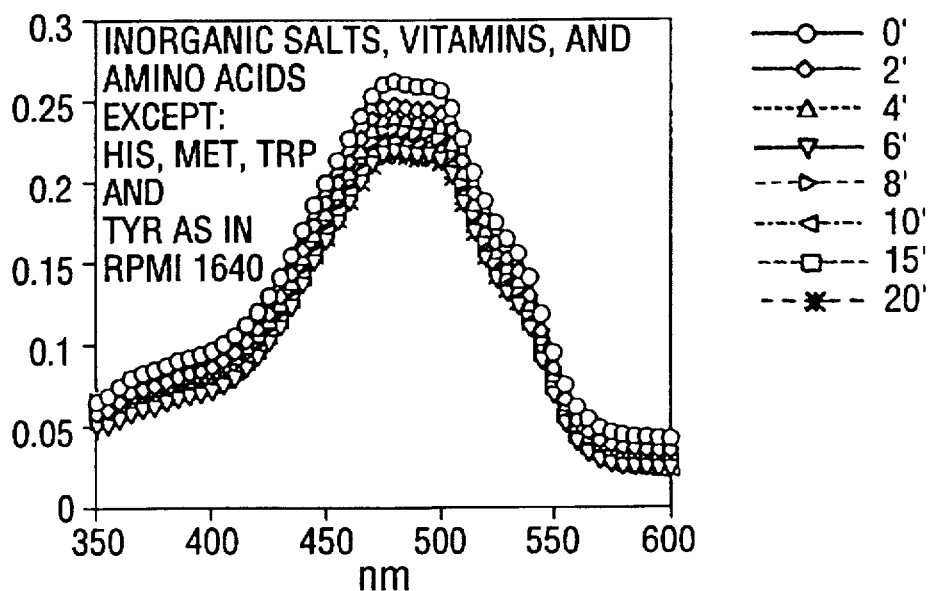
Figure 3C:
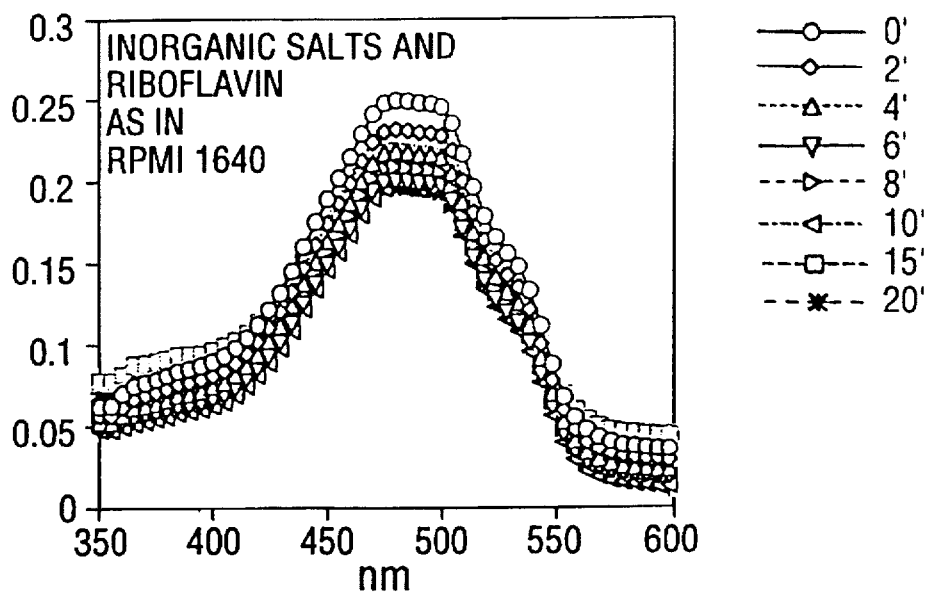
Figure 3D:
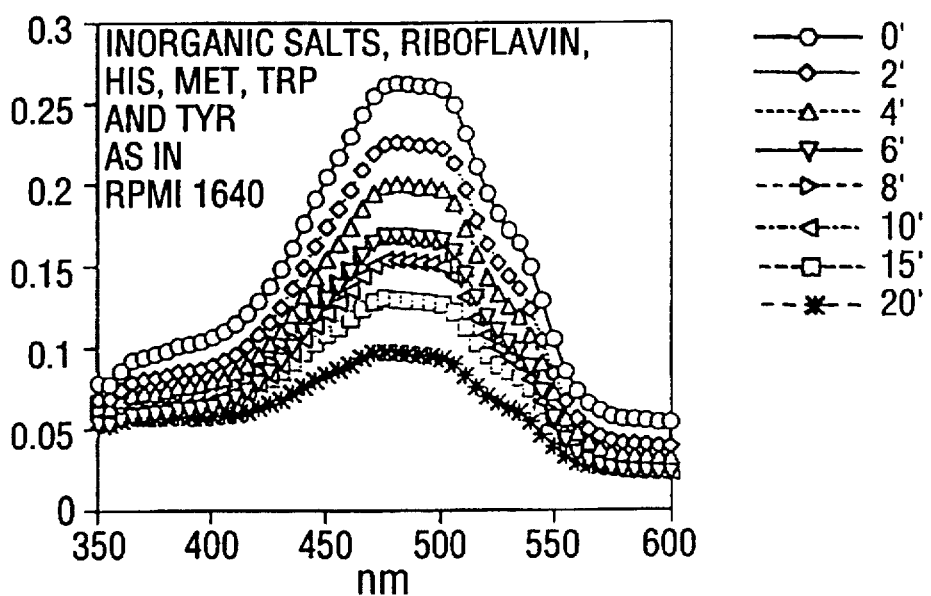
Figure 3E:
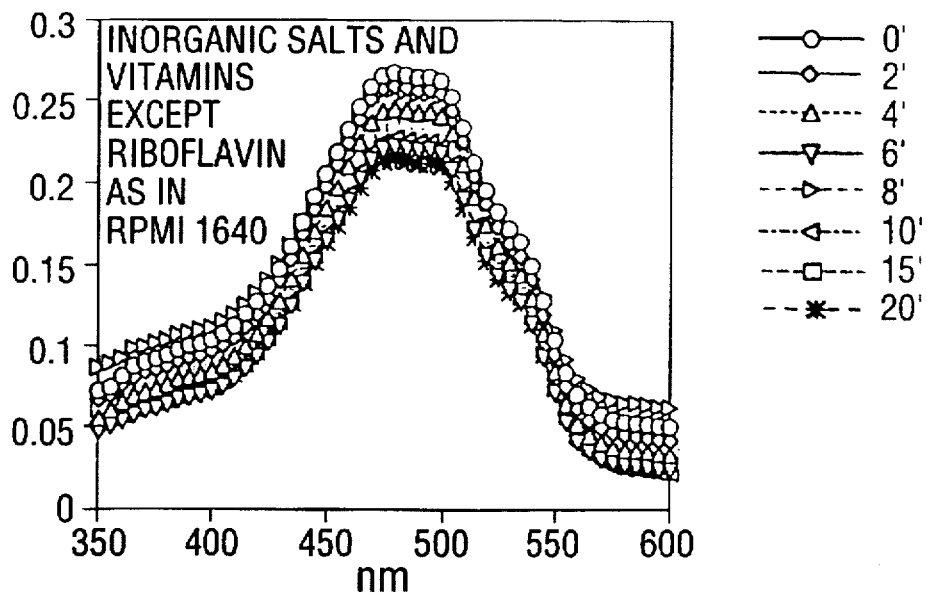
Figure 3F:
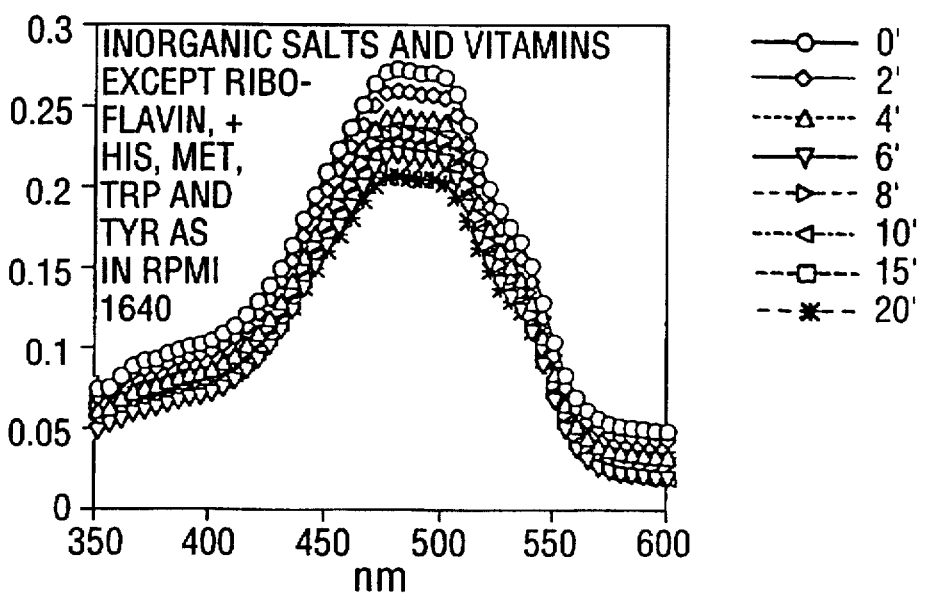

FIG. 3A shows the absorbance spectra obtained when DOX was dissolved in a solution containing the inorganic salts, vitamins and histidine, methionine, tryptophan and tyrosine found in RPMI medium 1640. FIG. 3B shows the absorbance spectra obtained when DOX was dissolved in a solution containing the inorganic salts, vitamins and all amino acids found in RPMI medium 1640 except histidine, methionine, tryptophan and tyrosine. FIG. 3C shows the absorbance spectra obtained when DOX was dissolved in a solution containing the inorganic salts and riboflavin found in RPMI medium 1640. FIG. 3D shows the absorbance spectra obtained when DOX was dissolved in a solution containing the inorganic salts, riboflavin and histidine, methionine, tryptophan and tyrosine found in RPMI medium 1640. FIG. 3E shows the absorbance spectra obtained when DOX was dissolved in a solution containing the inorganic salts and vitamins except riboflavin found in RPMI medium 1640. FIG. 3F shows the absorbance spectra obtained when DOX was dissolved in a solution containing the inorganic salts, vitamins except riboflavin and histidine, methionine, tryptophan and tyrosine found in RPMI medium 1640.

The results shown in FIG. 2 demonstrate that irradiating the drug in RPMI medium 1640 without phenol red containing 50 mM HEPES (to maintain pH=7.2) resulted in a decrease in absorbance in the 425–550 nm range. This decrease was an exponential function of the irradiation time with a first order rate constant of 0.025/min. When DOX was dissolved in a solution containing only the inorganic salts of RPMI medium 1640, the effect of UVA irradiation on the absorbance spectrum of DOX was 10 fold slower ($K_{DOX}$= 0.002/min).

Adding the 20 amino acids that are present in RPMI medium 1640 to its inorganic salts in concentration as in this medium accelerated somewhat the decrease in DOX absorbance resulting from the UVA irradiation ($K_{DOX}$=0.004/min). Adding the vitamin mixture to the inorganic salt solution also accelerated this reaction ($K_{DOX}$=0.007/min). However, when the amino acid and vitamin mixtures were added together to the inorganic salt solution, the reaction rate ($K_{DOX}$=0.029/min) reached a level comparable to that obtained in the standard RPMI medium 1640.

As shown in FIG. 3, to maintain the reaction at a high rate ($K_{DOX}$=0.025/min), it was sufficient to add just the following 4 amino acids: histidine, methionine, tryptophan and tyrosine with the vitamins. Furthermore, the other 16 amino acids did not accelerate the effect of UVA and vitamins on the absorbance spectrum of DOX ($K_{DOX}$=0.003/min). Without the vitamin mixture, histidine, methionine, tryptophan and tyrosine did not enhance the UVA irradiation effect on DOX ($K_{DOX}$=0.002/min). These results indicated that the effect of UVA on DOX in RPMI medium 1640 is carried out through some component(s) of the vitamin mixture serving as a photosensitizer and that the photosensitizer effect is enhanced by at least one of the following amino acids: histidine, methionine, tryptophan and tyrosine.

Riboflavin is a known photosensitizer [Girotti (1983) Photochem. Photobiol. 38:745]. Adding riboflavin to the concentration found in RPMI medium 1640 (0.5 µM) to the inorganic salt mixture somewhat accelerated the reaction ($K_{DOX}$=0.006/min). However, if histidine, methionine, tryptophan and tyrosine were also added, the reaction was highly accelerated ($K_{DOX}$=0.022/min). The effect of UVA irradiation on DOX dissolved in RPMI medium 1640 without riboflavin (FIG. 2) proceeded at a rate ($K_{DOX}$=0.007/min) that was significantly slower than that observed in the standard RPMI 1640. Similarly, the addition of a vitamin mixture lacking riboflavin to the inorganic salt mixture (FIG. 3) resulted in marginal acceleration of the reaction ($K_{DOX}$=0.004/min), which was not enhanced by adding histidine, methionine, tryptophan and tyrosine ($K_{DOX}$=0.005/min).

These data indicated that the major component mediating the destruction of DOX dissolved in RPMI medium 1640 by UVA is riboflavin and that this effect is accelerated, i.e., enhanced, by the presence of one or more of the following amino acids: histidine, methionine, tryptophan and tyrosine. In addition, the data suggested that the amino acid and vitamin mixtures may contain other minor photosensitizing components.

These results also demonstrate that the amelioration of the DOX growth inhibitory activity by UVA irradiation (shown in Example 1) correlates with structural changes in the DOX molecule. Therefore, the ability of a compound, alone or in combination with other compounds, to decrease the absorbance of DOX between 425 and 550 nm following UVA irradiation may be used to rapidly screen compounds for the ability to photoinactivate DOX.

EXAMPLE 3

The Effect Of Long Ultraviolet Light On Doxorubicin Is Mediated By Flavins

The preceding example demonstrated that the major component mediating the destruction of DOX dissolved in RPMI medium 1640 by UVA is riboflavin. Although many compounds have been shown to be modified by UVA and flavins (Girotti, supra), DOX has not previously been identified as such a compound. In this example, the ability of various flavins to cause the photoinactivation of DOX was examined by cell culture assays and spectral studies.

a) Effect Of Flavins And UVA Upon The Growth Inhibitory Effect Of DOX

DOX, at a concentration of 0.3 µM, was dissolved in 0.2 ml PBS with increasing concentrations of FMN or FAD. These solutions were then irradiated with UVA for 8 min. After irradiation, 1×10⁵ viable P388 cells in 0.8 ml complete growth medium were added to each well. After 4 days of culture, the cell density was measured. The results are presented in FIG. 4.

Figure 4:
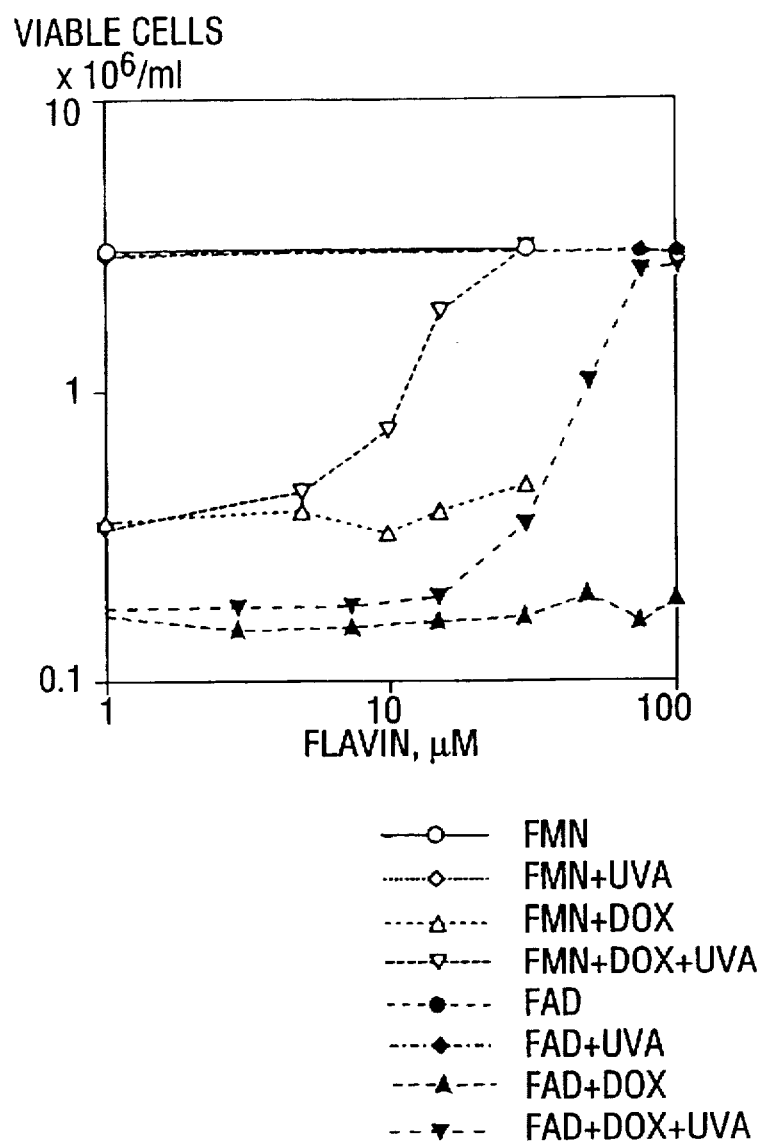
FIG. 4 shows the effect of an 8 min UVA irradiation of 0.3 µM DOX dissolved with FMN or FAD in 0.2 ml PBS on the growth inhibitory effect of DOX on P388 cells that were added after the irradiation in 0.8 ml growth medium.

In FIG. 4, the number of viable cells (×10⁶/ml) is plotted against the concentration of flavin (FMN or FAD) present in the DOX solution during irradiation. In FIG. 4, the results obtained using a solution containing either FMN or FAD in the absence of DOX and without irradiation are shown by the solid lines containing either an open circle or a filled circle (○, ●), respectively. The dotted lines containing either an open or a filled diamond (◇, ◆) represent the results obtained from irradiating a solution containing either FMN or FAD in the absence of DOX, respectively. The dashed lines containing either an open or a filled triangle (△, ▲) represent the results obtained using a solution containing either FMN or FAD in the presence of DOX but without irradiation, respectively. The dashed lines containing either open or filled inverted triangles (▽,▼) represent the results obtained using a solution containing either FMN or FAD in the presence of DOX and irradiation, respectively.

As can be seen in FIG. 4, UVA irradiation of DOX in PBS for 8 minutes did not affect the growth inhibitory affect of DOX. Similarly, DOX in combination with flavins at the specified concentrations without irradiation, showed no affect on the growth inhibitory effect of DOX. However, UVA irradiation of DOX in the presence of flavins at the specified concentrations obliterated the growth inhibitory effect of DOX on P388 cells. FMN was found to be as effective as riboflavin, and 5 fold more effective than FAD.

b) Effect Of Flavins And UVA Upon The Absorbance Spectrum Of DOX

The effect of UVA irradiation of 20 µM DOX, 20 µM riboflavin or 20 µM DOX with 20 µM riboflavin in PBS on the absorbance spectra of DOX and riboflavin was measured using the assay described in Example 2. The results are shown in FIGS. 5 and 6.

Figure 5A:
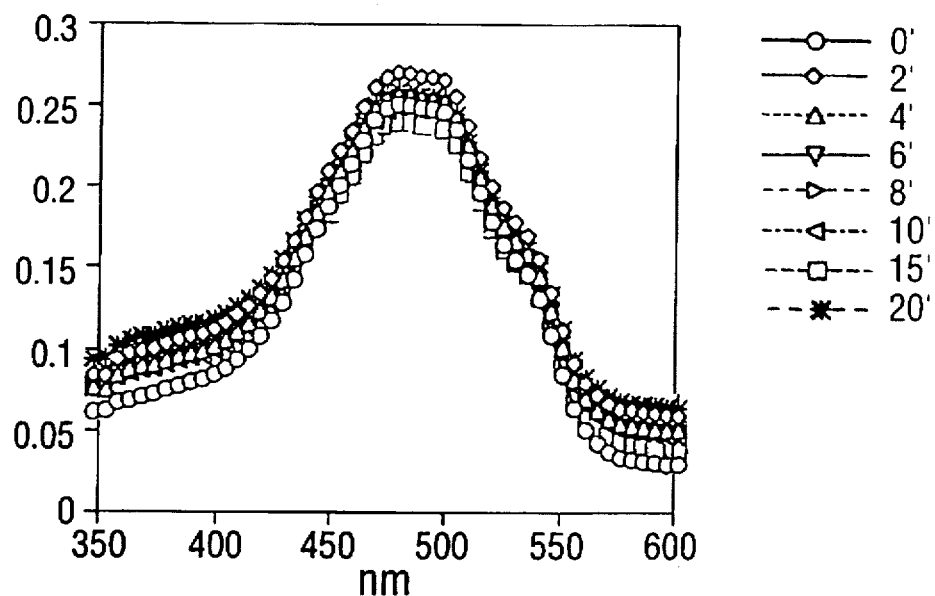
FIGS. 5A and 5B show the effect of the length of UVA irradiation of 20 µM DOX dissolved in PBS, in the absence or presence of 20 µM riboflavin, on the absorbance spectrum of DOX.
Figure 5B:
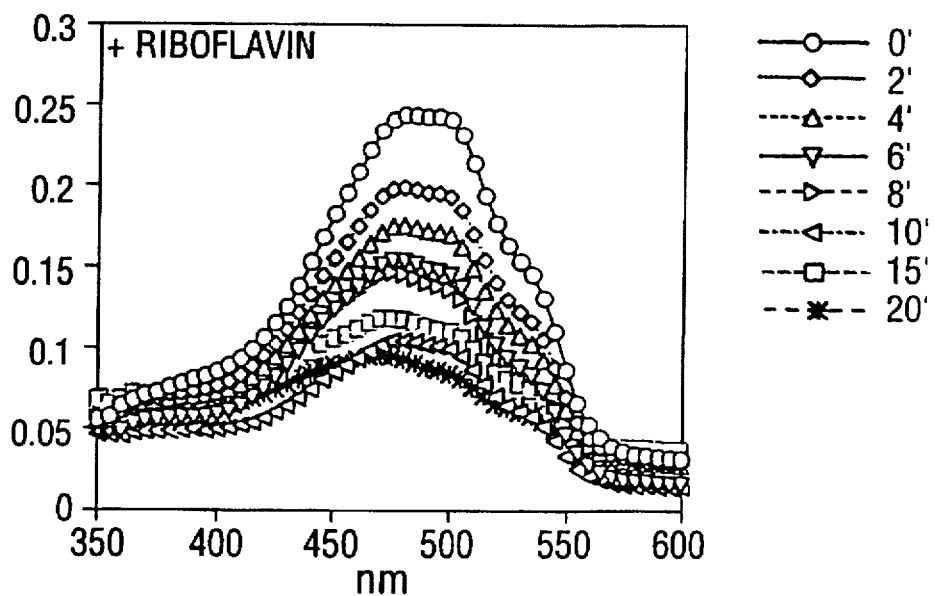

In FIGS. 5A and 5B, solutions containing 20 µM DOX in PBS were irradiated for 0, 2, 4, 6, 8, 10, 15 or 20 minutes in the absence or presence of 20 µM riboflavin, respectively and the absorbance spectrum between 350–600 nm was measured.

Figure 6A:
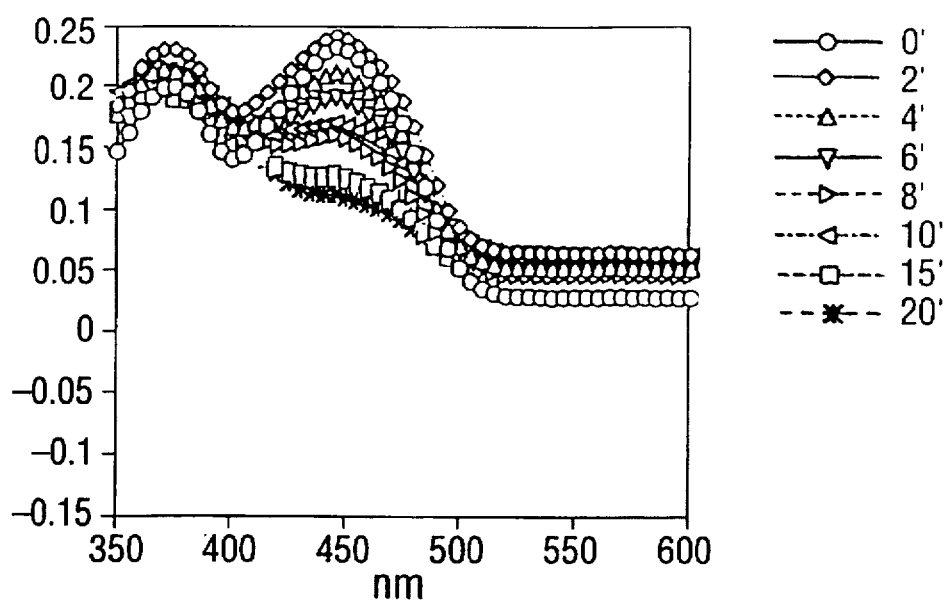
FIGS. 6A and 6B show the effect of the length of UVA irradiation of 20 µM riboflavin dissolved in PBS, in the absence or presence of 20 µM DOX, on the absorbance spectrum of riboflavin.
Figure 6B:
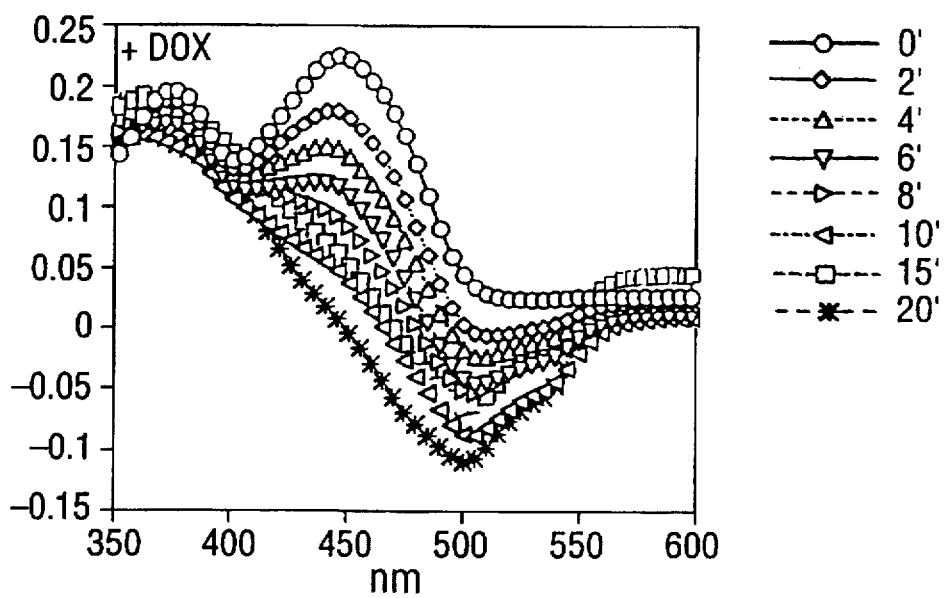

In FIGS. 6A and 6B, solutions containing 20 µM riboflavin in PBS were irradiated for 0, 2, 4, 6, 8, 10, 15 or 20 minutes in the absence or presence of 20 µM DOX, respectively and the absorbance spectrum between 350–600 nm was measured.

The results shown in FIGS. 5 and 6 demonstrate that in the presence of riboflavin, the UVA irradiation caused a much larger decrease in the absorbance of DOX than in its absence. In the presence of DOX, UVA irradiation of riboflavin resulted in a larger decrease in the vitamin absorbance maximum at 445 nm (but not at 360 nm maximum) than in its absence. These results indicate that the UVA effects on DOX and on riboflavin are enhanced by their combined presence.

EXAMPLE 4

Effects Of Ascorbic Acid, De-aeration And Catalase Upon The Absorbance Spectrum Of DOX The results shown in Example 3 demonstrated that the effect of UVA irradiation on DOX and on riboflavin were enhanced by the combination of these two compounds. It is known that flavins, excited by 365 nm light, can undergo photoreduction while oxidizing certain substrates [Byron and Turnbill (1967) Photochem. Photobiol. 6:125]. Therefore, the changes in the cell growth inhibitory activity and in the absorbance spectrum of DOX after UVA irradiation in the presence of flavins could reflect oxidation of the drug.

To test this hypothesis, the experiment described in Example 3b was repeated as described with the exception that 0.16 or 1.6 mM of ascorbic acid was added to each solution. The absorbance spectrum of DOX irradiated in the presence of riboflavin did not decline, while the absorbance spectrum of riboflavin declined at a much faster rate than that observed in the absence of ascorbate. Thus, ascorbate protected DOX from UVA while enhancing the effect of the irradiation on riboflavin.

Figure 7:
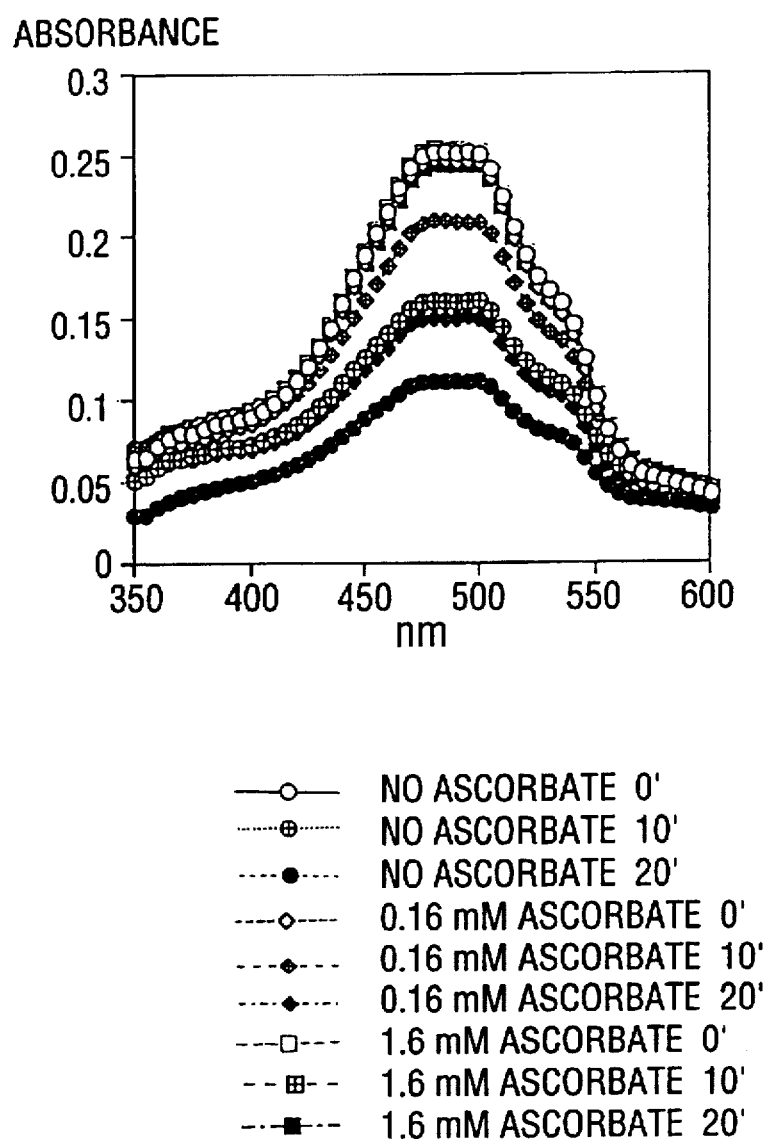
FIG. 7 shows the effect of the presence of ascorbic acid on the changes that UVA irradiation induce in the absorbance spectrum of 20 µM DOX irradiated in RPMI medium 1640 without phenol red.

The protective effect of ascorbate on DOX from UVA is further demonstrated by the results shown in FIG. 7. FIG. 7 depicts the absorbance spectrum obtained from solutions of 20 µM DOX in RPMI medium 1640 containing 0, 0.16 or 1.6 mM ascorbate were irradiated for 0, 10 or 20 minutes.

In FIG. 7, the circles represent solutions lacking ascorbate; the open circles represent no irradiation; the hatched and filled circles represent 10 and 20 minutes of irradiation, respectively. The diamonds represent solutions containing 0.16 mM ascorbate; the open diamonds represent no irradiation; the hatched and filled diamonds represent 10 and 20 minutes of irradiation, respectively. The squares represent solutions containing 1.6 mM ascorbate; the open squares represent no irradiation; the hatched and filled squares represent 10 and 20 minutes of irradiation, respectively.

The results shown in FIG. 7 demonstrate the protective effect of ascorbate. The irradiation of 20 µM DOX in RPMI medium 1640 (no ascorbate) resulted in decreased DOX absorbance. However, in the presence of 0.16 mM ascorbate this decrease was smaller and in the presence of 1.6 mM ascorbate, even after 20 minutes of irradiation, there were no changes in the absorbance spectrum of DOX.

As demonstrated in Example 3b, UVA irradiation of a solution of 20 µM DOX and 20 µM riboflavin in PBS resulted in the decline of DOX absorbance spectrum. Because some of the photosensitizing effects might be mediated through dissolved oxygen, the experiment was repeated after depleting the solution of oxygen by nitrogen bubbling prior to the irradiation. The results indicated that oxygen deprivation had no effect on the decline in DOX absorbance and suggested that oxygen does not participate in the destruction of DOX by the combination of UVA and riboflavin.

Hydrogen peroxide is also known to be produced and participate in certain photosensitizing reactions [Brawley et al. (1993) *Clin. Sci.* 85:709]. Therefore, the effect of adding 150 units/ml catalase (which at room temperature could decompose 450 µmole/min hydrogen peroxide), to 20 µM DOX dissolved in RPMI medium 1640 was tested. It was found that the presence of catalase in this solution did not affect the rate of destruction of DOX by the UVA irradiation. This result suggested that it is unlikely that hydrogen peroxide mediates the destruction of DOX by the UVA-riboflavin combination.

EXAMPLE 5

Effect Of Irradiation Time Upon The Growth Inhibitory Activity Of Doxorubicin Solutions Containing Flavins The effect of increasing the length of UVA irradiation of solutions containing 0.3 µM DOX in PBS with increasing concentrations of flavins (riboflavin, FMN or FAD) was examined.

The effect of increasing the length of UVA irradiation of solutions containing 0.3 µM DOX in PBS with increasing concentrations of riboflavin was examined as follows. Two-tenths of a milliliter of 0.3 µM DOX with increasing concentrations of riboflavin (0 to 15 µM) in PBS (pH 7.2) was placed in 24 well culture clusters and exposed to 3 Blacklight Blue 40 W lamps (emitting 5–6 mW/cm$^2$ at 365 nm) for various amounts of time (0 to 8 min.). Growth medium (0.8 ml) containing $1 \times 10^5$ P388 murine leukemia cells was then added and the cultures were allowed to incubate for 4 days and the cell density was determined. The results are shown in FIG. 8.

Figure 8:
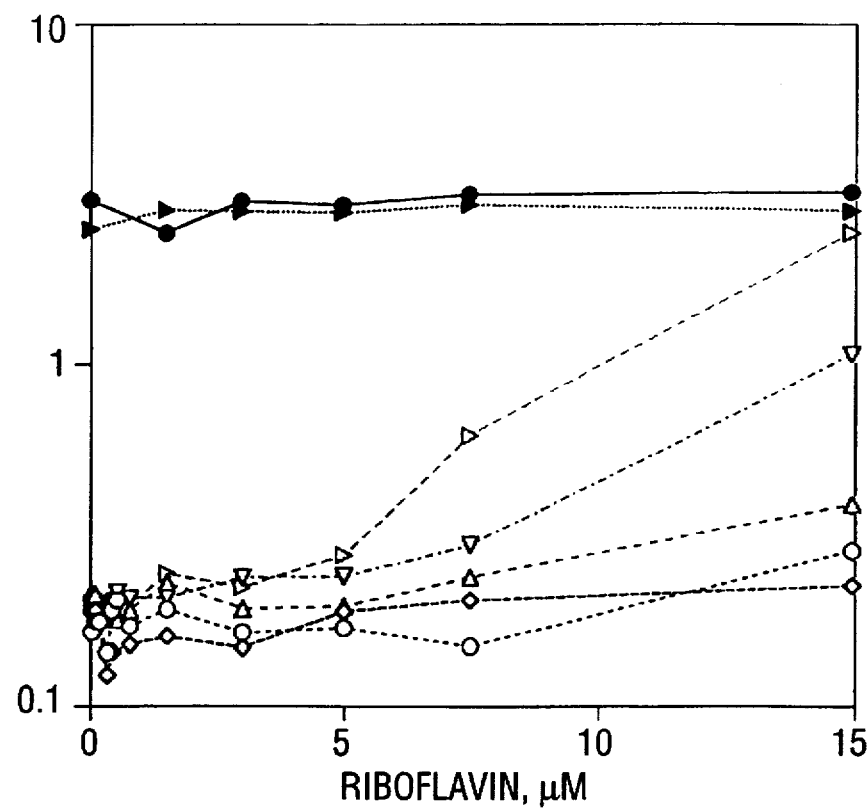
FIG. 8 shows the effect of the length of UVA irradiation of 0.3 µM DOX containing increasing amounts of riboflavin in PBS (pH=7.2) on the growth inhibitory effect of DOX on P388 cells.

In FIG. 8, the filled circles and filled triangles represent the density of cells present 4 days after exposure of cells to 0.2 ml of PBS containing increasing amounts of riboflavin (0 to 15 µM) which received either 0 or 8 minutes of irradiation, respectively (positive controls). The density of cells present after exposure to 0.2 ml of a solution containing 0.3 µM DOX with increasing concentrations of riboflavin (0 to 15 µM) in PBS (pH 7.2) and 0, 2, 4, 6, and 8 minutes of irradiation are shown by the open circles, open diamonds, open triangles, open inverted triangles and open side-ways triangles, respectively. It is noted that the final (i.e., after the addition of the cells) concentration of riboflavin present in each well is 5-fold lower than the value shown along the x-axis of FIG. 8 (as well, the final concentration of DOX is 5 fold lower than the stated initial concentration).

The results shown in FIG. 8 demonstrate that the presence of increasing amounts of riboflavin increases the photoinactivation of DOX. As the amount of riboflavin was increased, a gradual loss of the DOX growth inhibitory activity toward $1 \times 10^5$ P388 murine leukemia cells was observed. In the presence of 15 µM riboflavin, the growth inhibitory effect of DOX was destroyed after 8 minutes of exposure to UVA light. Similar effects were obtained in the presence of the riboflavin analogs, flavin mononucleotide (FMN) and flavin adenine dinucleotide (FAD) (FIG. 9).

Figure 9:
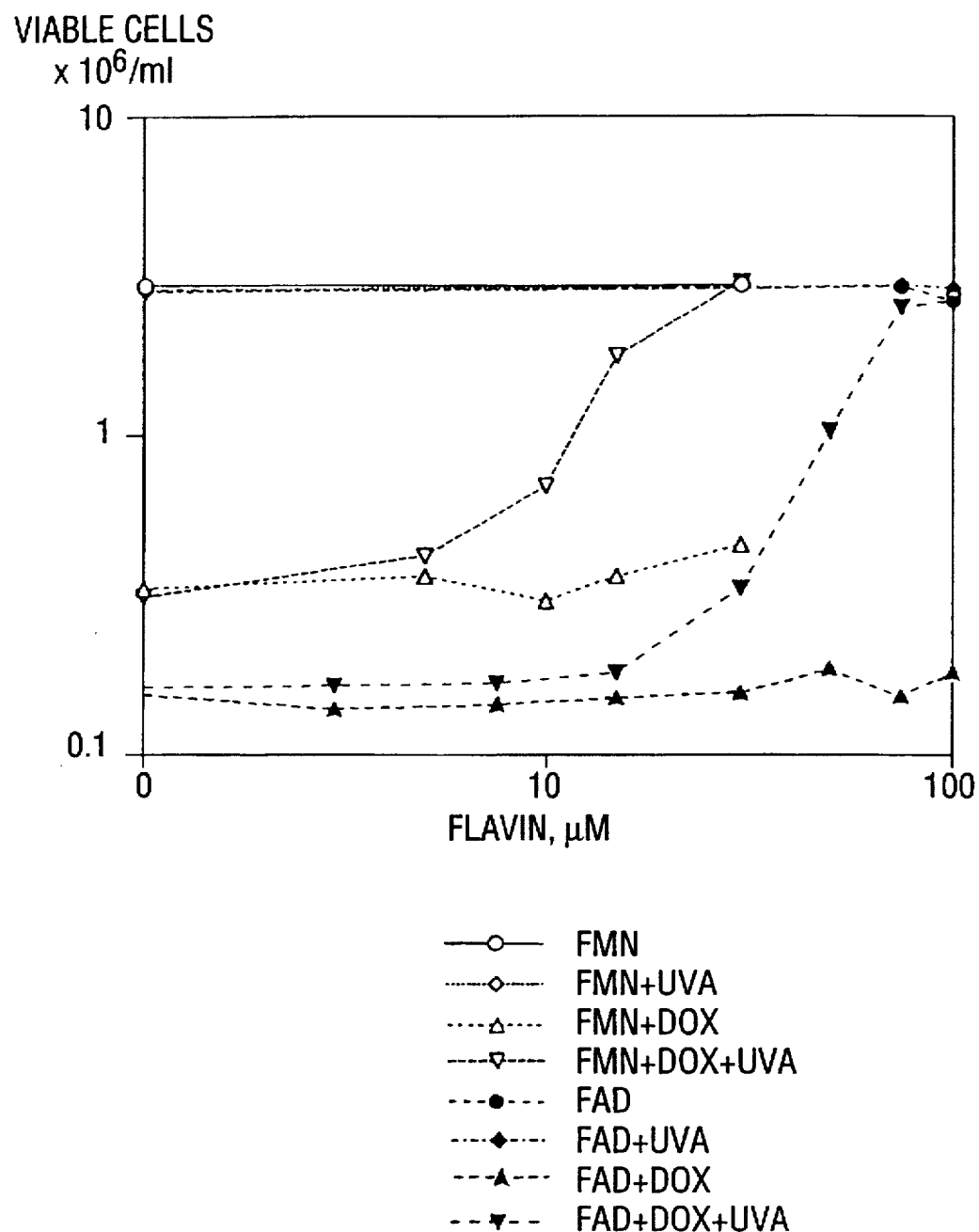
FIG. 9 shows the effect of an 8 minute UVA irradiation of 0.3 µM DOX containing increasing amounts of FMN or FAD in PBS (pH=7.2) on the growth inhibitory effect of DOX on P388 cells.

The results shown in FIG. 9 were generated as described above with the exception that FMN or FAD was used in place of riboflavin and the concentrations of flavins varied from 0 to 100 µM. In FIG. 9, the open and filled symbols represent results obtained using FMN and FAD, respectively. The circles represent results obtained using flavin solutions lacking DOX which were not irradiated. The diamonds represent the results obtained using flavin solutions lacking DOX which were irradiated for 8 minutes. The triangles represent the results obtained using flavin solutions containing DOX which were not irradiated. The inverted triangles represent flavin solutions containing DOX which were irradiated for 8 minutes.

Figure 10A:
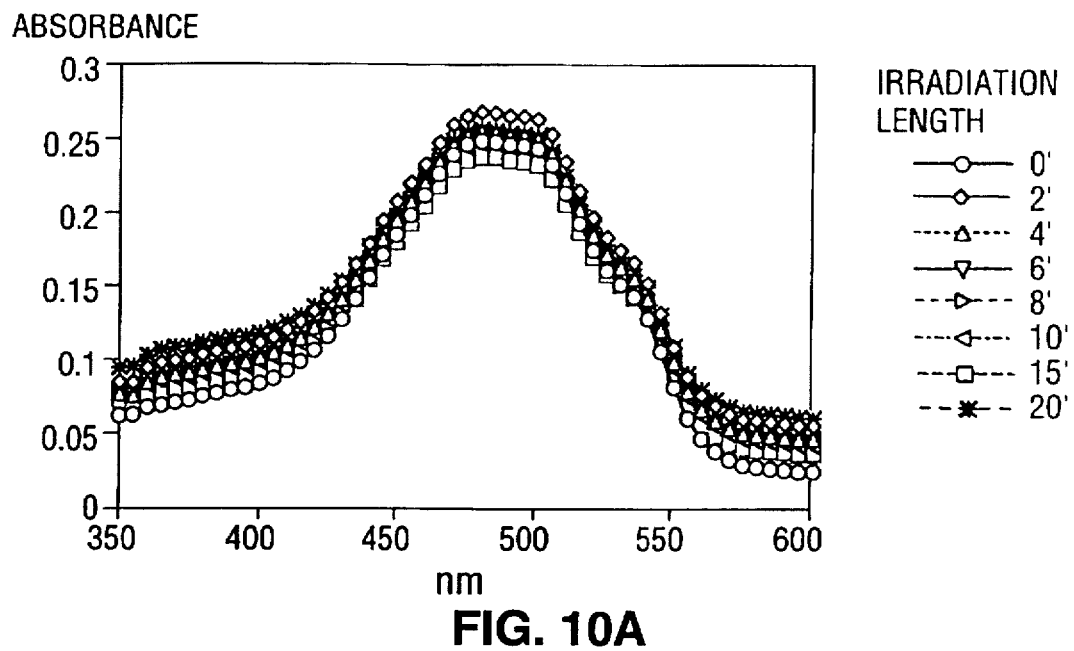
FIGS. 10A–10C show the effect of the length of UVA irradiation of 20 µM DOX dissolved in PBS, in the absence or presence of 2 or 20 µM riboflavin, on the absorbance spectrum of DOX.
Figure 10B:
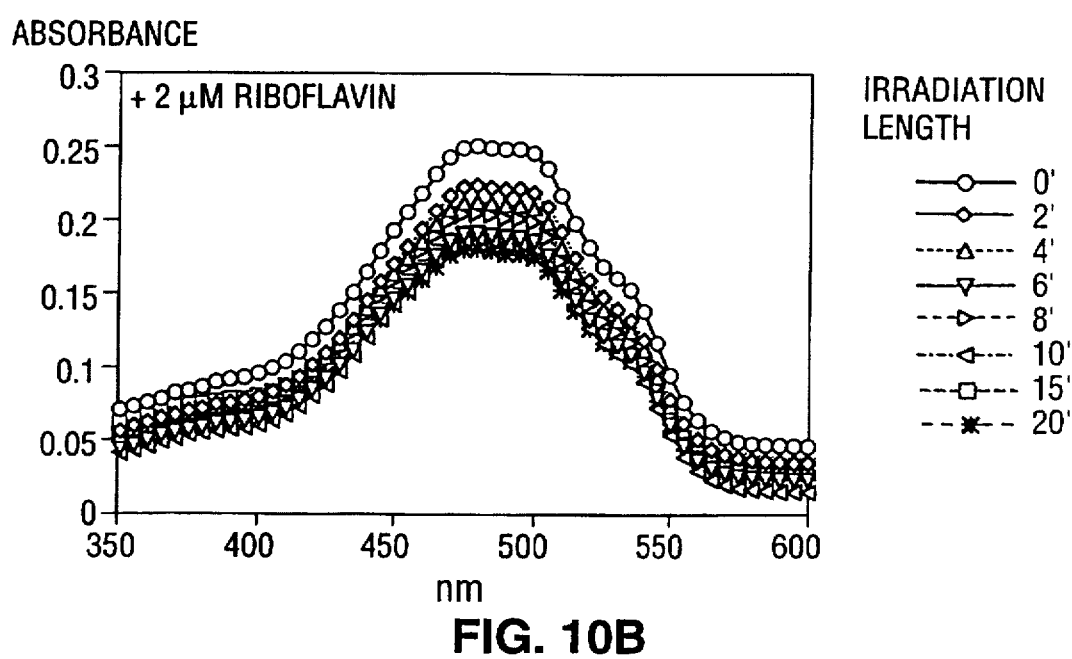
Figure 10C:
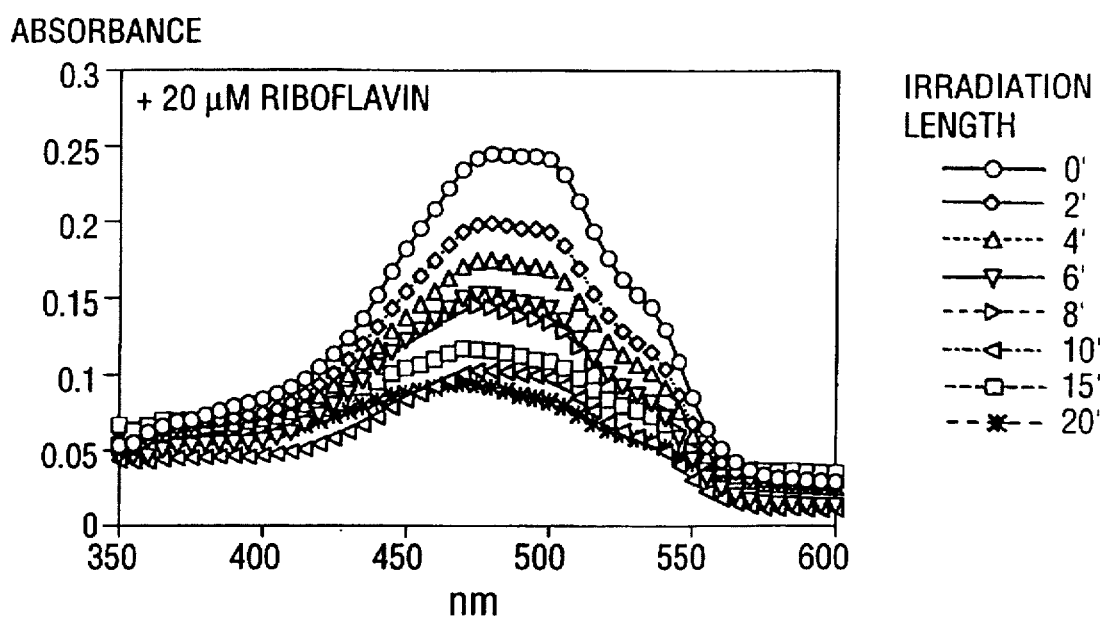

The absorbance spectrum of solutions containing 0.3 µM DOX in PBS and 0, 2 or 20 µM riboflavin was determined as described in Example 2; irradiation times varied from 0 to 20 minutes. The results are shown in FIG. 10. FIG. 10A shows absorbance spectrum from solutions containing 0.3 µM DOX in PBS without riboflavin; FIGS. 10B and 10C show absorbance spectrum from solutions containing 0.3 µM DOX in PBS with either 2 or 20 µM riboflavin, respectively. The following symbols indicate 0, 2, 4, 6, 8, 10, 15 or 20 minutes of irradiation, respectively: ○, ◇, △, ▽, ▶, ◀, □, *.

The results shown in FIG. 10 demonstrate that the reduction in the growth inhibitory activity of DOX by UVA irradiation resulted from changes in its chemical structure. FIG. 10, shows that riboflavin, in a concentration dependent manner, enhances the decrease in 400 to 550 nm absorbance of DOX which is caused by UVA induced chemical changes.

EXAMPLE 6

The Photoinactivation of Doxorubicin In The Presence Of Flavins Is Enhanced By Other Compounds In this experiment, the ability of compounds to enhance the photoinactivation of DOX by flavins was examined. The following compounds were examined: 1,4-diazabicyclo(2, 2,2)octane (DABCO), N-2-hydroxyethylpiperazine-N'-2-ethanesulfonic acid (HEPES), 1,4-Dimethylpiperazine and tyrosine.

a) The Addition Of DABCO Accelerates The Destruction Of DOX By Riboflavin

Figure 11A:
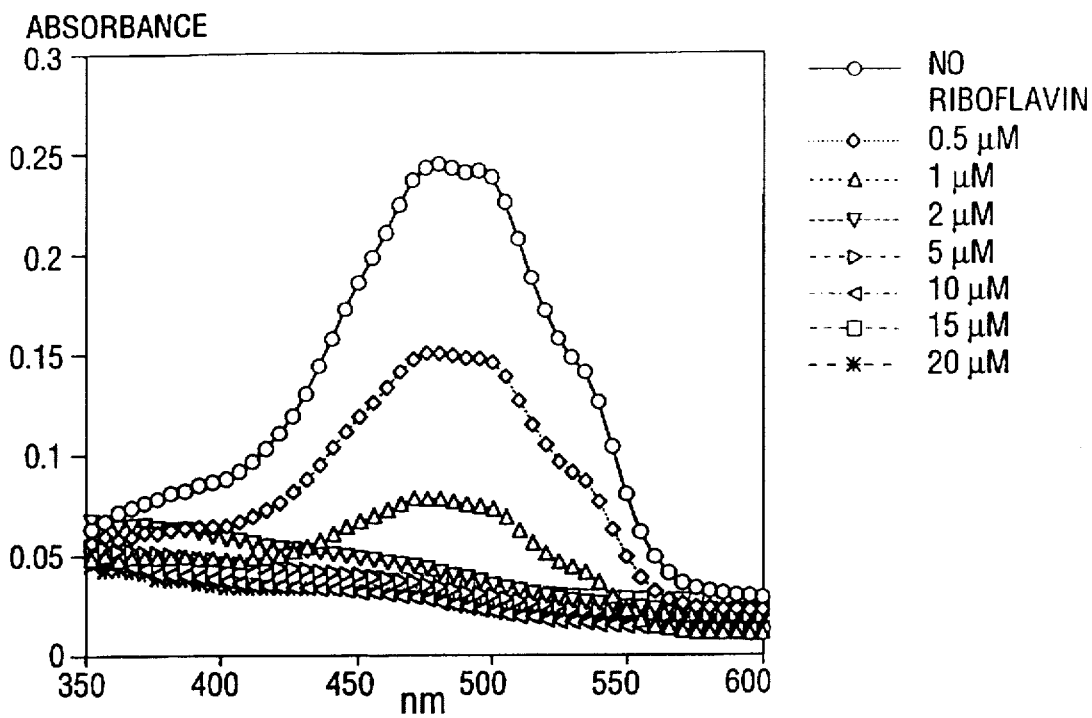
FIG. 11A shows the effect of 20 minutes of UVA irradiation of 20 µM DOX with 5 mM DABCO dissolved in PBS and increasing concentrations of riboflavin on the absorbance spectrum of DOX.

The UVA mediated destruction of DOX with riboflavin is enhanced by the presence of 1,4-diazabicyclo(2,2,2)octane (DABCO) (FIGS. 11–13). In FIG. 11A, the effect on the absorbance spectrum of DOX is shown when solutions containing 5 mM DABCO and 20 µM DOX in PBS (pH 7.2) and increasing concentrations of riboflavin (0 to 20 µM) were irradiated for 20 minutes. In FIG. 11A, the following symbols represent 0, 0.5, 1, 2, 5, 10, 15 and 20 µM riboflavin, respectively: ●, ◊, ▲, ▽, ▶, ◀, □, and *.

Figure 11B:
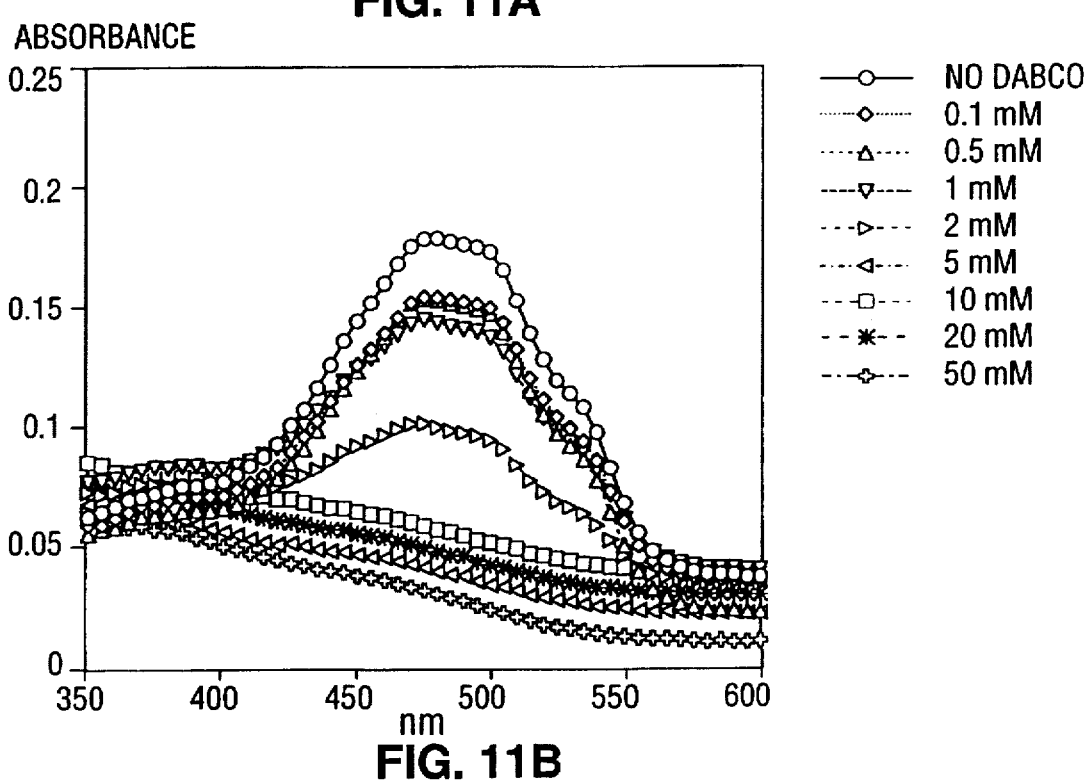
FIG. 11B shows the effect of 20 minutes of UVA irradiation of 20 µM DOX with 2 µM riboflavin dissolved in PBS and increasing concentrations of DABCO on the absorbance spectrum of DOX.

In FIG. 11B, the effect on the absorbance spectrum of DOX is shown when solutions containing 2 µM riboflavin and 20 µM DOX in PBS (pH 7.2) and increasing concentrations of DABCO (0 to 50 mM) were irradiated for 20 minutes. In FIG. 11B, the following symbols represent 0, 0.1, 0.5, 1, 2, 5, 10, 20 and 50 mM DABCO, respectively: ●, ◊, ▲, ▽, ▶, ◀, □, *, and †.

Figure 12A:
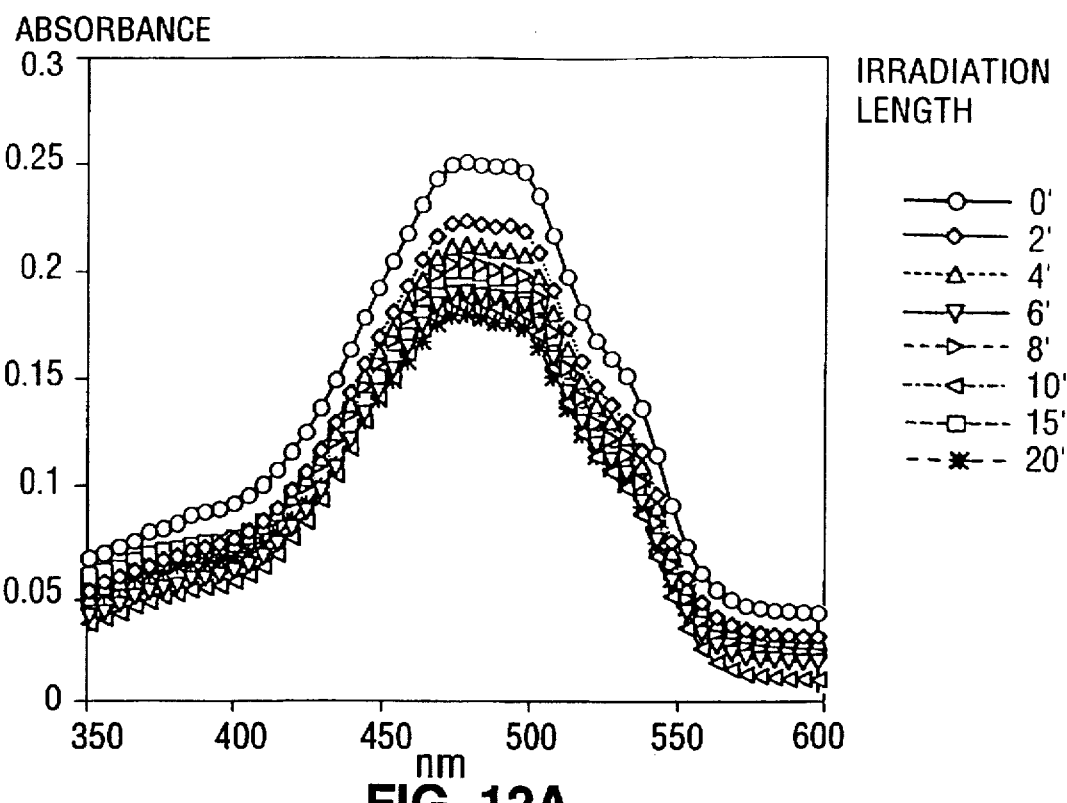
FIGS. 12A and 12B show the effect of the length of UVA irradiation of 20 µM DOX with 2 µM riboflavin in PBS, in the absence or presence of 5 mM DABCO on the absorbance spectrum of DOX.
Figure 12B:
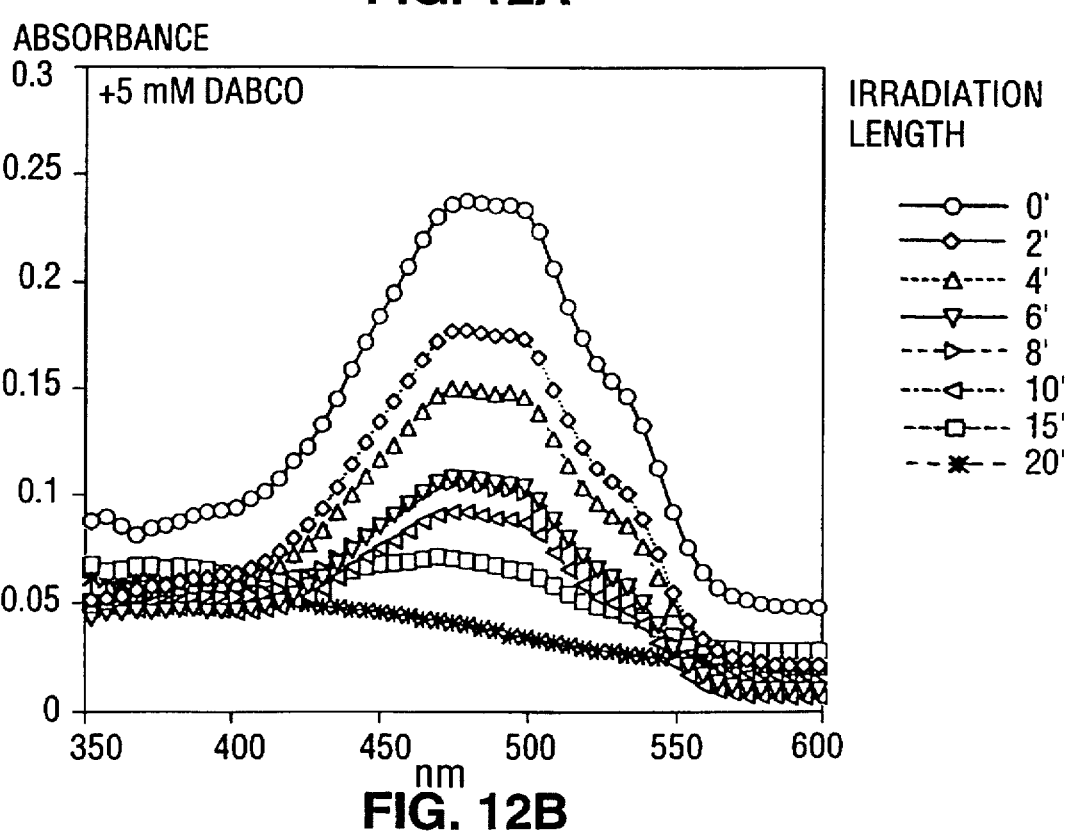

In FIG. 12, the effect of UVA irradiation of solutions containing 20 µM DOX and 2 µM riboflavin in PBS (pH 7.2) with or without 5 mM DABCO is shown. In FIG. 12A, the effect on the absorbance spectrum of DOX is shown when solutions containing 2 µM riboflavin and 20 µM DOX in PBS (pH 7.2) were exposed to UVA for increasing periods of time. In FIG. 12A, the following symbols represent 0, 2, 4, 6, 8, 10, 15 and 20 minutes of irradiation, respectively: ●, ◊, ▲, ▽, ▶, ◀, □, and *. FIG. 12B shows the effect on the absorbance spectrum of DOX is shown when solutions containing 2 µM riboflavin, 5 mM DABCO and 20 µM DOX in PBS (pH 7.2) were exposed to UVA for increasing periods of time. In FIG. 12B, the following symbols represent 0, 2, 4, 6, 8, 10, 15 and 20 minutes of irradiation, respectively: ●, ◊, ▲, ▽, ▶, ◀, □, and *.

Figure 13A:
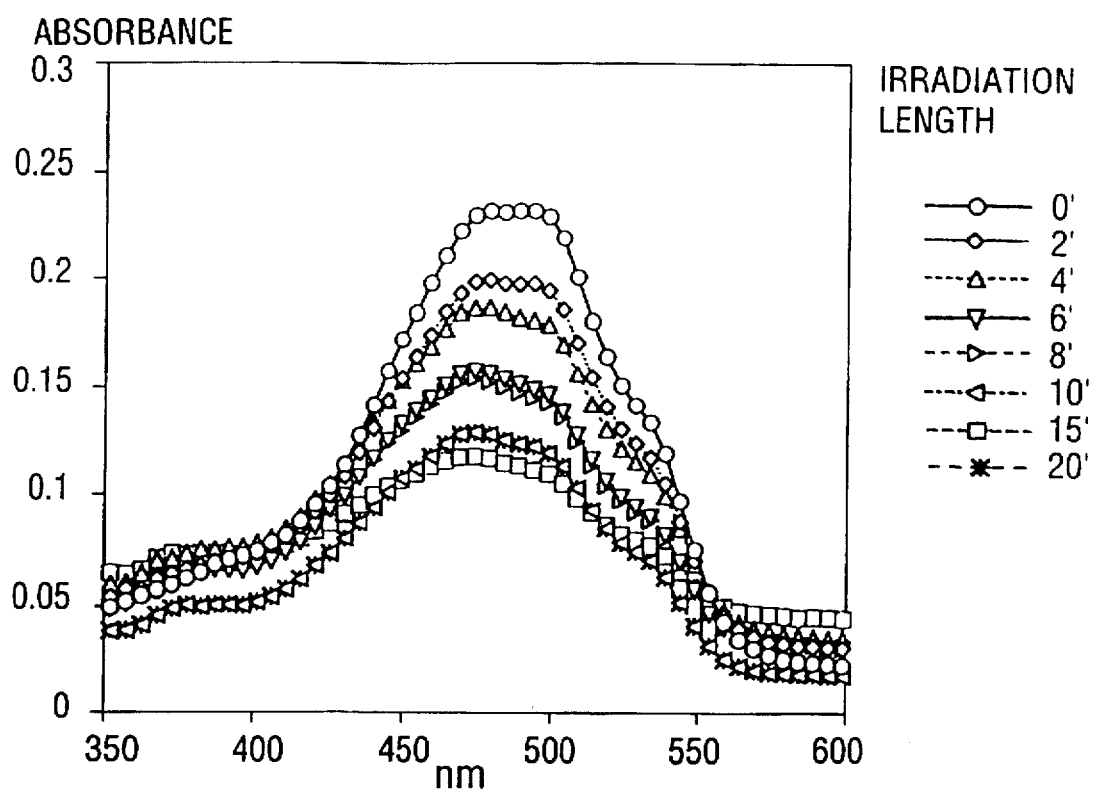
FIGS. 13A–13C show the effect of the length of UVA irradiation of 20 µM DOX with 20 µM riboflavin in PBS, in the absence or presence of 5 mM DABCO on the absorbance spectrum of DOX.
Figure 13B:
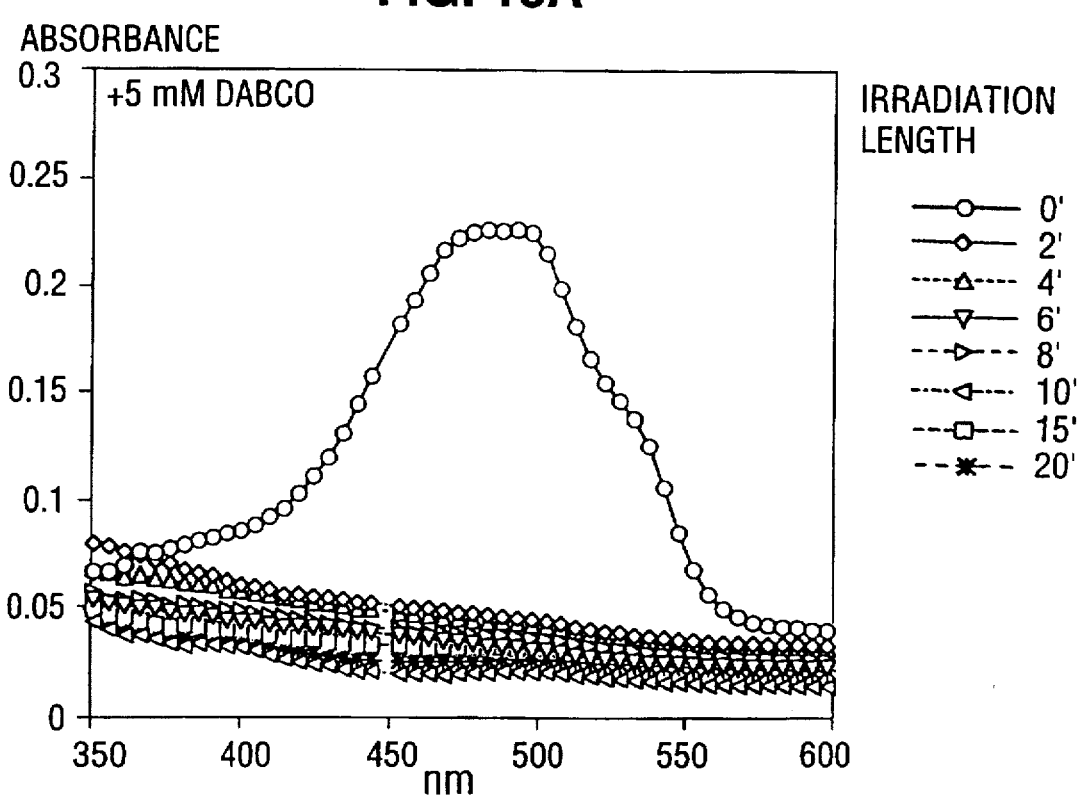
Figure 13C:
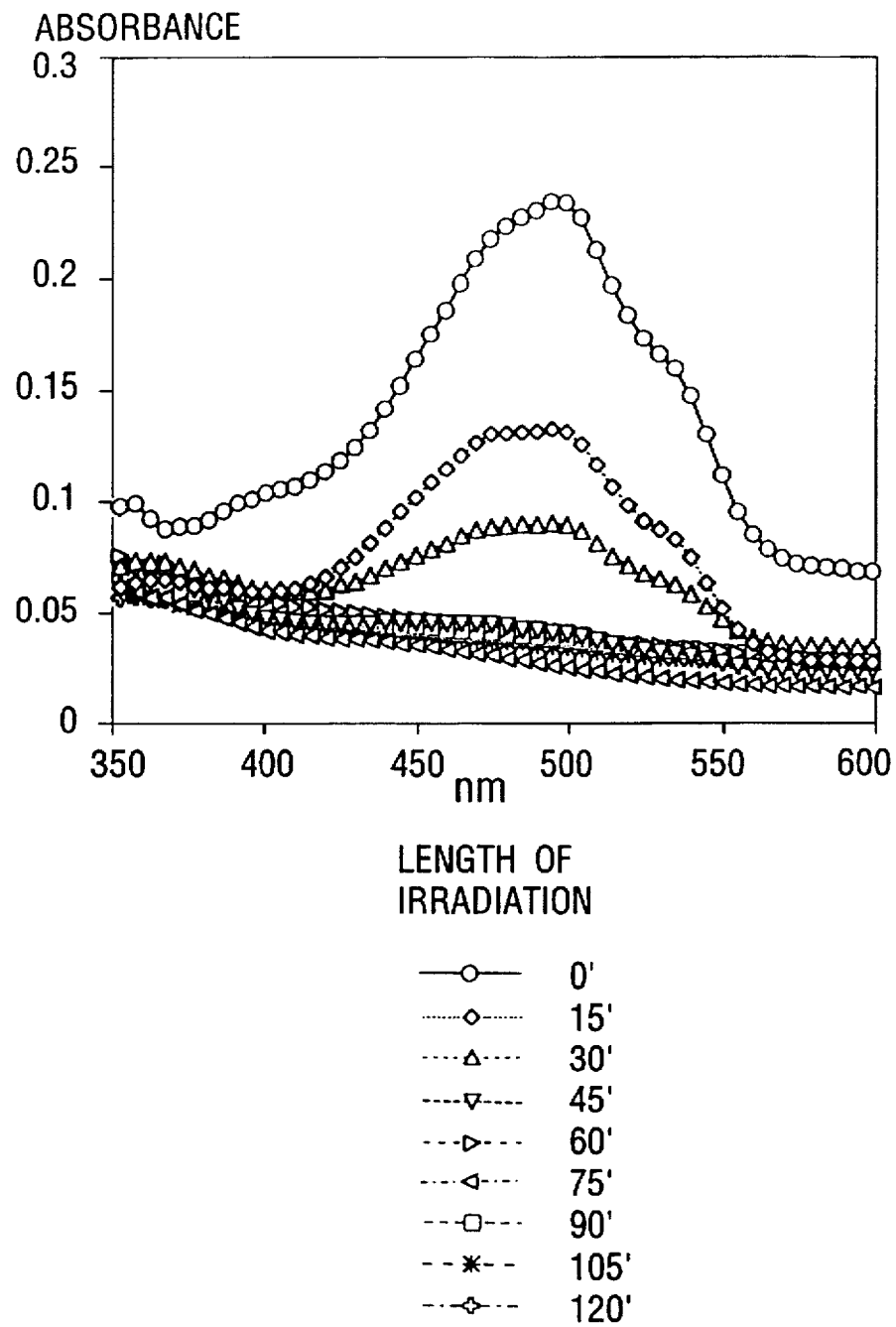

In FIG. 13, the effect of UVA irradiation of solutions containing 20 µM DOX and 20 µM riboflavin in PBS (pH 7.2) with or without 5 mM DABCO is shown. In FIG. 13A, the effect on the absorbance spectrum of DOX is shown when solutions containing 20 µM riboflavin and 20 µM DOX in PBS (pH 7.2) were exposed to UVA for increasing periods of time. In FIG. 13A, the following symbols represent 0, 2, 4, 6, 8, 10, 15 and 20 minutes of irradiation, respectively: ●, ◊, ▲, ▽, ▶, ◀, □, and *. FIG. 13B shows the effect on the absorbance spectrum of DOX when solutions containing 20 µM riboflavin, 5 mM DABCO and 20 µM DOX in PBS (pH 7.2) were exposed to UVA for increasing periods of time. In FIG. 13B, the following symbols represent 0, 2, 4, 6, 8, 10, 15 and 20 minutes of irradiation, respectively: ●, ◊, ▲, ▽, ▶, ◀, □, and *. FIG. 13C shows the effect on the absorbance spectrum of DOX when solutions containing 20 µM riboflavin, 5 mM DABCO and 20 µM DOX in PBS without $Ca^{2+}$ and $Mg^{2+}$ (pH 7.2) were exposed to UVA for very short periods of time. In FIG. 13C, the following symbols represent 0, 15, 30, 45, 60, 75, 90, 105 and 120 seconds of irradiation, respectively: ●, ◊, ▲, ▽, ▶, ◀, □, *, and †.

The results shown in FIGS. 11–13 demonstrate that the addition of DABCO further accelerates the destruction of DOX by riboflavin and UVA. In the presence of 5 mM DABCO, 2 µM riboflavin was sufficient to destroy the DOX absorbance spectrum (20 µM DOX) in the 425–550 nm range after 20 minutes of UVA irradiation (FIG. 11A) (loss of absorbance in the 425–550 nm range was shown above to correlate with a loss of cytotoxic activity). FIG. 11B shows that in the presence of 2 µM riboflavin, less than 5 mM, but more than 2 mM, DABCO were sufficient to destroy the DOX absorbance spectrum in the 425–550 nm range after 20 minutes of UVA irradiation. In the presence of 2 µM riboflavin and 5 nM DABCO, 20 minutes of UVA irradiation were required to destroy the DOX absorbance spectrum (FIG. 12). However, raising the concentration of riboflavin to 20 µM, decreased the amount of UVA irradiation required to destroy DOX absorbance (FIGS. 13A–C). FIG. 13B shows that less than 2 minutes of UVA irradiation was required to eliminate the DOX absorbance spectrum at these concentrations and FIG. 13C shows that the DOX absorbance spectrum disappeared in less than 1 minute in the presence of 20 µM riboflavin and 5 mM DABCO.

b) The Addition Of DABCO Accelerates The Destruction Of DOX By FAD

The UVA mediated destruction of DOX with FAD is enhanced by the presence of 1,4-diazabicyclo(2.2.2)octane (DABCO).

Figure 14A:
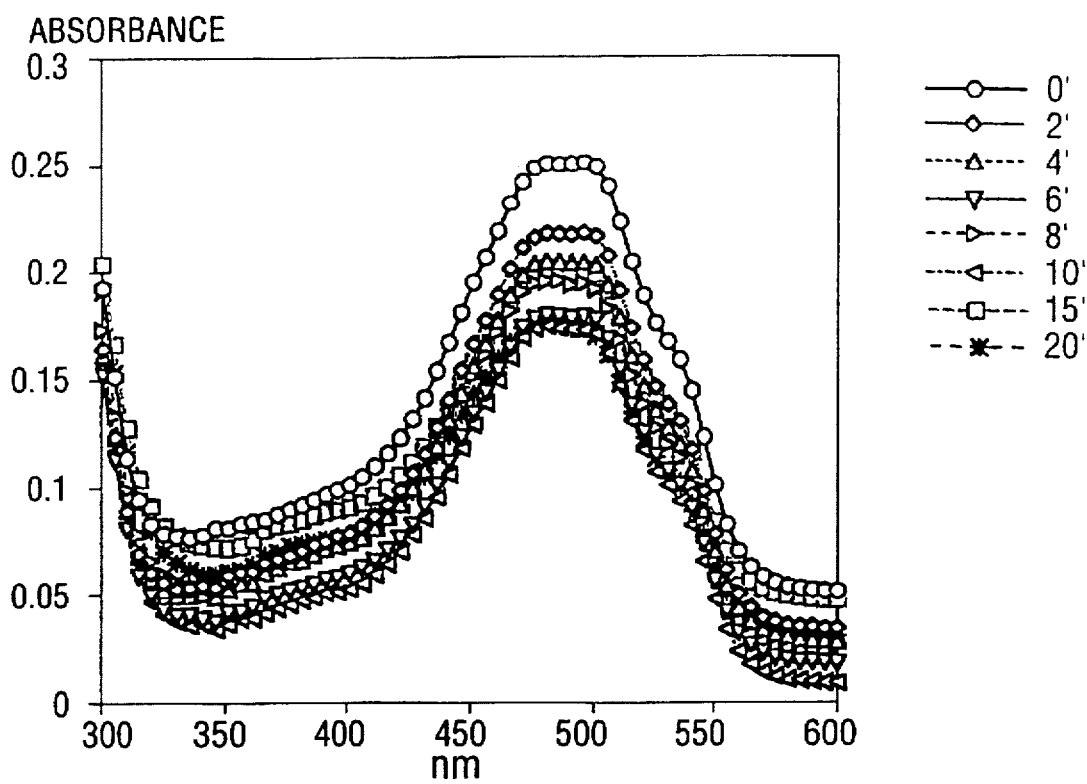
FIGS. 14A and 14B show the effect of the length of UVA irradiation of 20 µM DOX with 20 µM FAD in PBS, in the absence or presence of 5 mM DABCO on the absorbance spectrum of DOX.

In FIG. 14, the effect of UVA irradiation of solutions containing 20 µM DOX and 20 µM FAD in PBS lacking $Ca^{2+}$ and $Mg^{2+}$ (pH 7.2) with or without 5 mM DABCO is shown. In FIG. 14A, the effect on the absorbance spectrum of DOX is shown when solutions containing 20 µM FAD and 20 µM DOX in PBS lacking $Ca^{2+}$ and $Mg^{2+}$ (pH 7.2) were exposed to UVA for increasing periods of time. In FIG. 14A, the following symbols represent 0, 2, 4, 6, 8, 10, 15 and 20 minutes of irradiation, respectively: ●, ◊, ▲, ▽, ▶, ◀, □, and *.

Figure 14B:
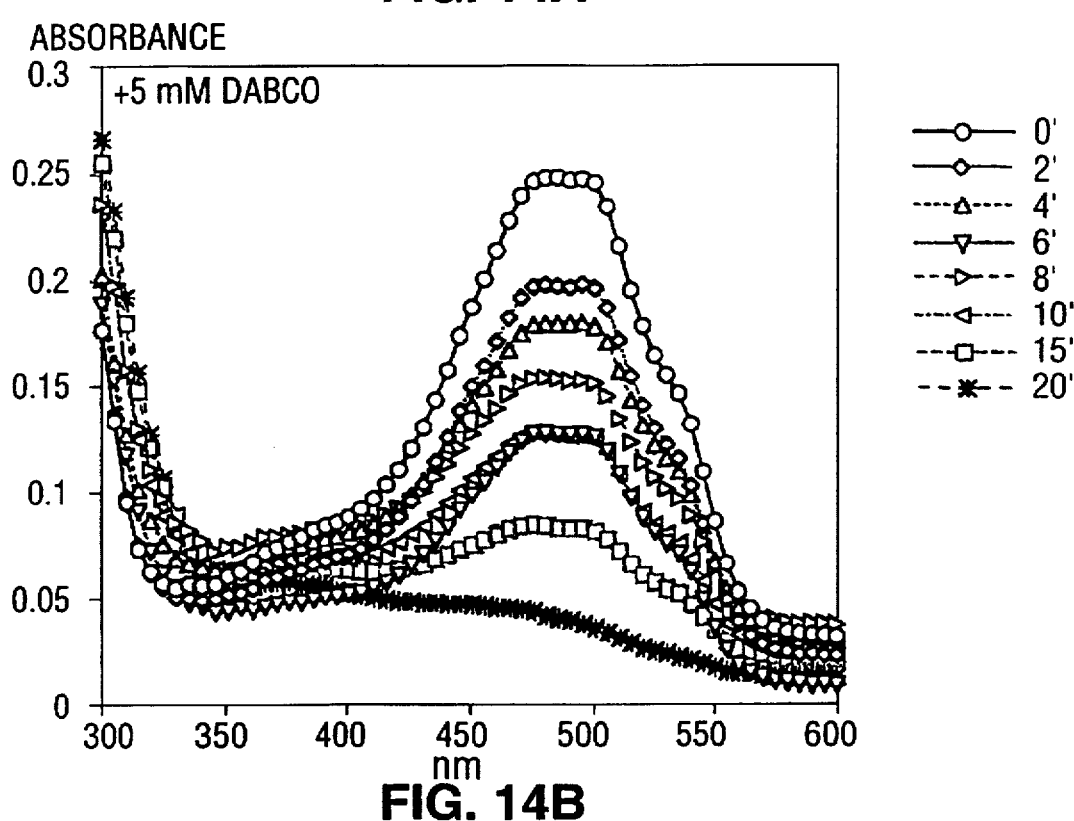

FIG. 14B shows the effect on the absorbance spectrum of DOX is shown when solutions containing 20 µM FAD, 5 mM DABCO and 20 µM DOX in PBS lacking $Ca^{2+}$ and $Mg^{2+}$ (pH 7.2) were exposed to UVA for increasing periods of time. In FIG. 14B, the following symbols represent 0, 2, 4, 6, 8, 10, 15 and 20 minutes of irradiation, respectively: ●, ◊, ▲, ▽, ▶, ◀, □, and *.

The results shown in FIG. 14 demonstrate that the addition of DABCO further accelerates the destruction of DOX by FAD and UVA. A comparison of the results shown in FIG. 12 and FIG. 14 demonstrates that FAD was not as effective as riboflavin in mediating the UVA inactivation of DOX, in the presence or absence of DABCO. However, the results shown in FIG. 14 demonstrate that DABCO considerably enhanced the effect of FAD-UVA on DOX.

c) The Addition of Piperazine Compounds And/Or Tyrosine Accelerates The Destruction of DOX By Riboflavin The ability of piperazine compounds such as N-2-hydroxyethylpiperazine-N'-2-ethanesulfonic acid (HEPES) and 1,4-Dimethylpiperazine to enhance the riboflavin-mediated UVA destruction of DOX was examined. In addition, the ability of HEPES and 1,4-Dimethylpiperazine to enhance the destruction of DOX by the combination of UVA-riboflavin-tyrosine was examined. Furthermore, the ability of tyrosine to act as a photoenhancer in the absence of piperazine compounds was examined. The UVA irradiation and spectral measurements were carried as described in Example 2.

Figure 15A:
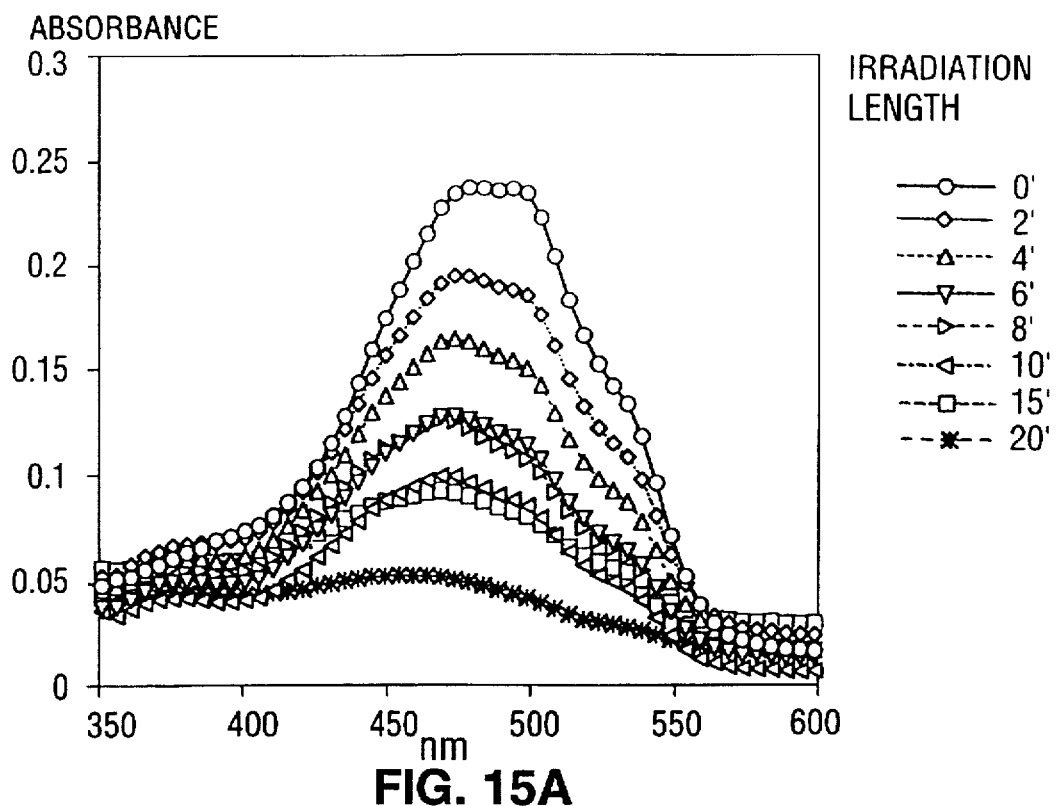
FIGS. 15A and 15B show the effect of the length of UVA irradiation of 20 µM DOX with 20 µM riboflavin in PBS, in the absence or presence of 5 mM HEPES on the absorbance spectrum of DOX.
Figure 15B:
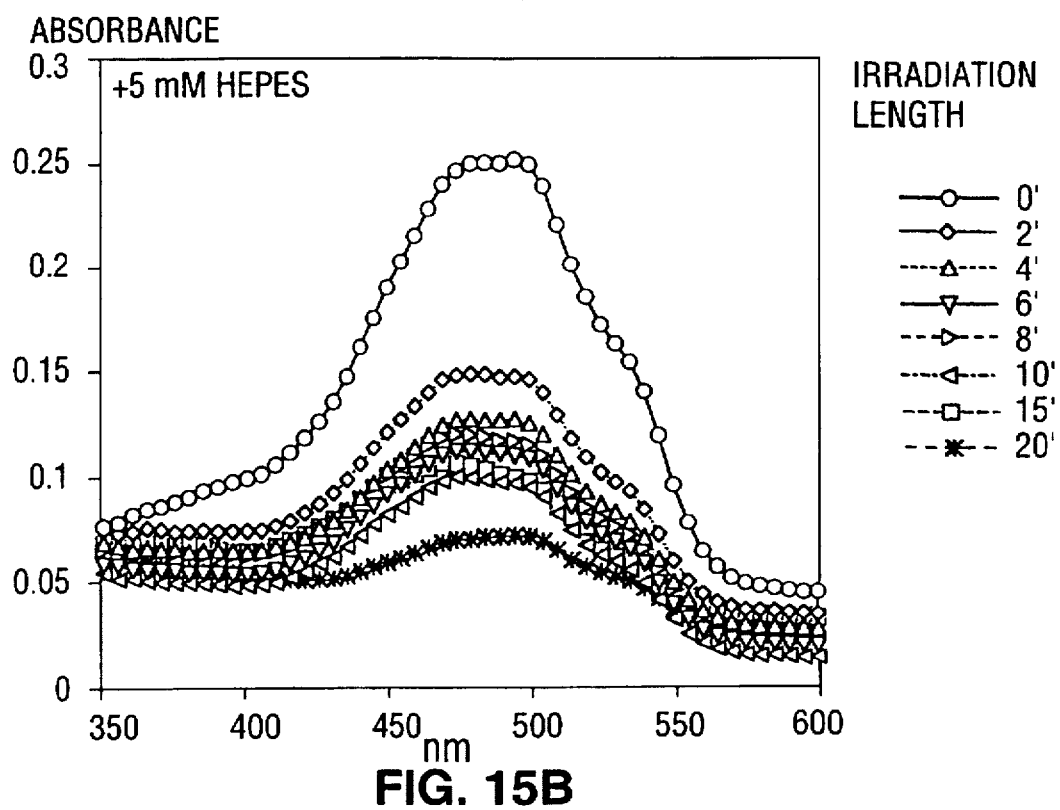

In FIG. 15, the effect of UVA irradiation of solutions containing 20 µM DOX and 20 µM riboflavin in PBS (pH 7.2) in the presence or absence of 5 mM HEPES on the absorbance spectrum of DOX is shown. FIGS. 15A and 15B show the spectrum obtained from solutions containing 20 µM DOX and 20 µM riboflavin in PBS (pH 7.2) with and without 5 mM HEPES, respectively. In FIG. 15, the following symbols represent 0, 2, 4, 6, 8, 10, 15 and 20 minutes of irradiation, respectively: ●, ◊, ▲, ▽, ▶, ◀, □, and *.

Figure 16:
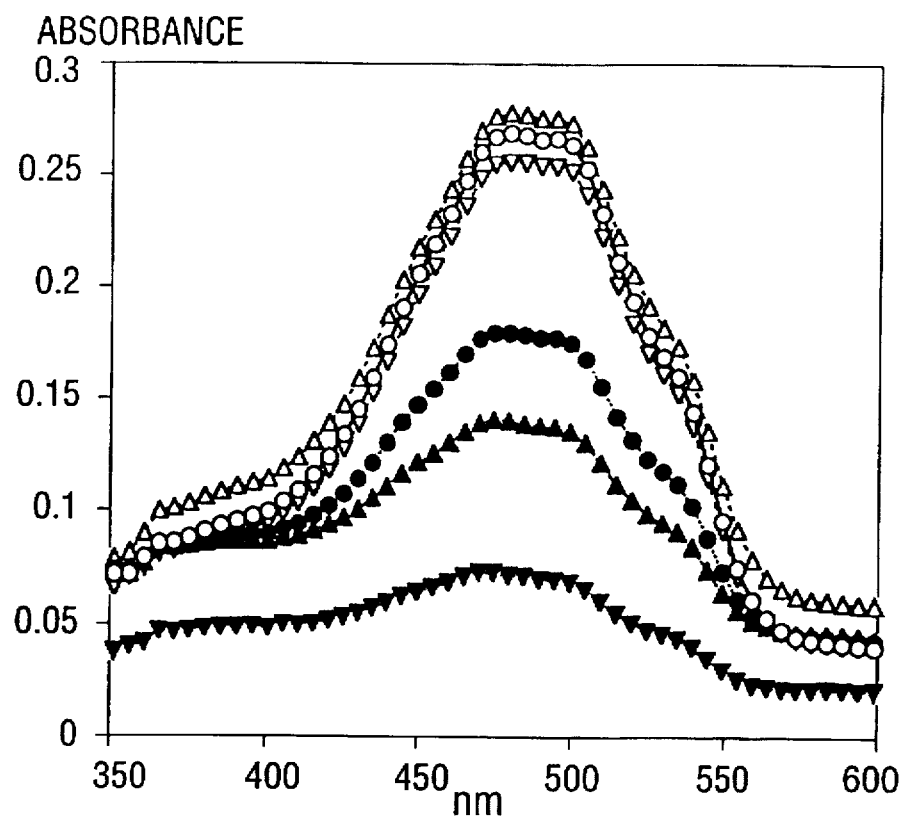
FIG. 16 shows the effect of UVA irradiation of 20 µM DOX with 5 µM riboflavin, 5 mM HEPES and 0, 20 or 80 µM tyrosine in 0.1M NaCl on the absorbance spectrum of DOX.

In FIG. 16, the effect of UVA irradiation of solutions containing 20 µM DOX, 0.5 µM riboflavin and 5 mM HEPES with 0, 20 or 80 µM tyrosine in 0.1M NaCl on the absorbance spectrum of DOX is shown. In FIG. 16, the open symbols represent solutions which were not irradiated and the filled symbols represent solutions which received 20 minutes of UVA irradiation. The circles, triangles and inverted triangles represent solutions containing 0, 20 and 80 µM tyrosine, respectively.

Figure 17:
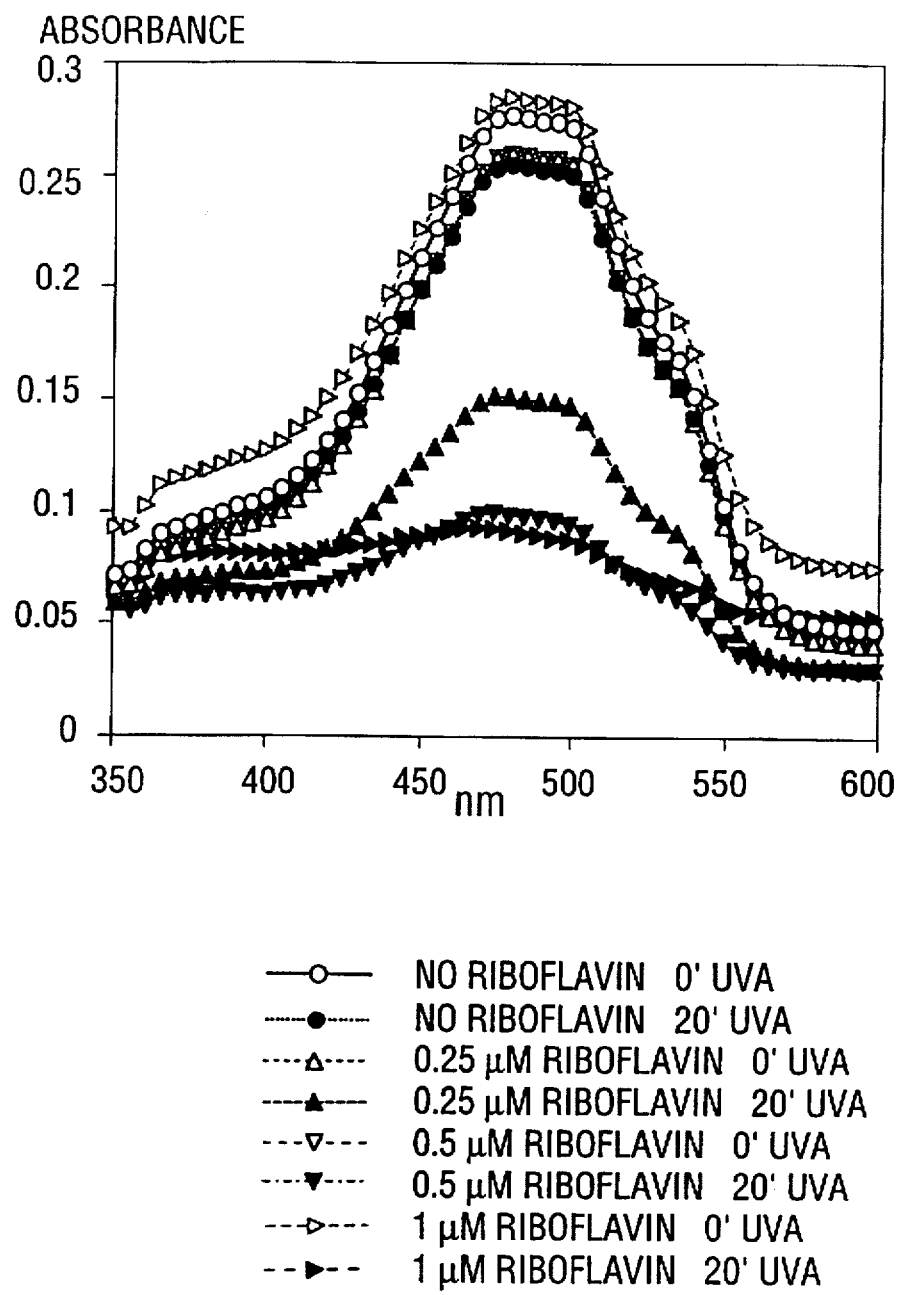
FIG. 17 shows the effect of UVA irradiation of 20 µM DOX with 40 µM tyrosine, 5 mM HEPES and 0, 0.25, 0.5 or 1 µM riboflavin in 0.1M NaCl on the absorbance spectrum of DOX.

In FIG. 17, the effect of UVA irradiation of solutions containing 20 µM DOX, 40 µM tyrosine and 5 mM HEPES with 0, 0.25, 0.5 or 1 µM riboflavin in 0.1M NaCl on the absorbance spectrum of DOX is shown. In FIG. 17, the open symbols represent solutions which were not irradiated and the filled symbols represent solutions which received 20 minutes of UVA irradiation. The circles, triangles, inverted triangles and side-ways triangles (▸) represent solutions containing 0, 0.25, 0.5 and 1 μM riboflavin, respectively.

Figure 18:
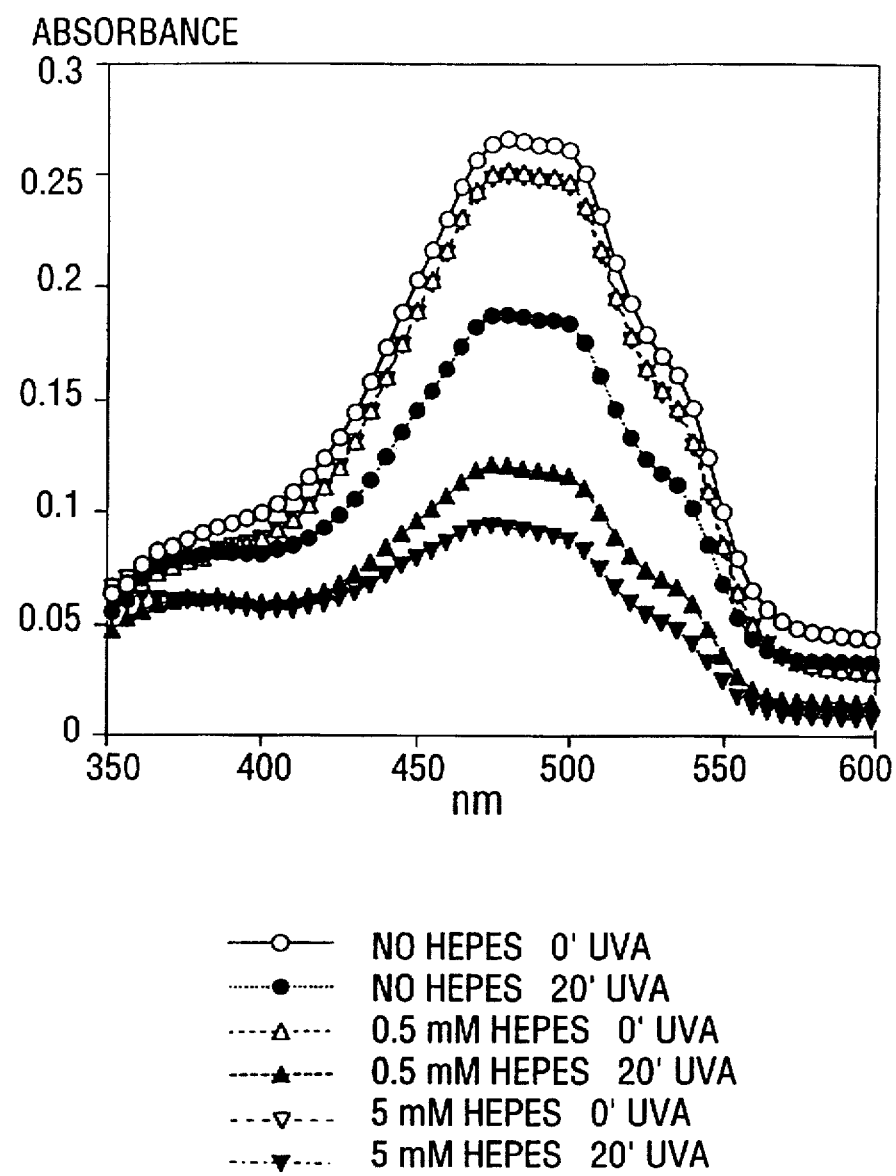
FIG. 18 shows the effect of UVA irradiation of 20 µM DOX with 0.5 µM riboflavin, 100 µM tyrosine and 0, 0.5, or 5 mM HEPES in PBS on the absorbance spectrum of DOX.

In FIG. 18, the effect of UVA irradiation of solutions containing 20 μM DOX, 0.5 μM riboflavin and 100 μM tyrosine with 0, 0.5, or 5 mM HEPES tyrosine in PBS (pH 7.2) on the absorbance spectrum of DOX is shown. In FIG. 18, the open symbols represent solutions which were not irradiated and the filled symbols represent solutions which received 20 minutes of UVA irradiation. The circles, triangles and inverted triangles represent solutions containing 0, 0.5 and 5 mM HEPES, respectively.

Figure 19A:
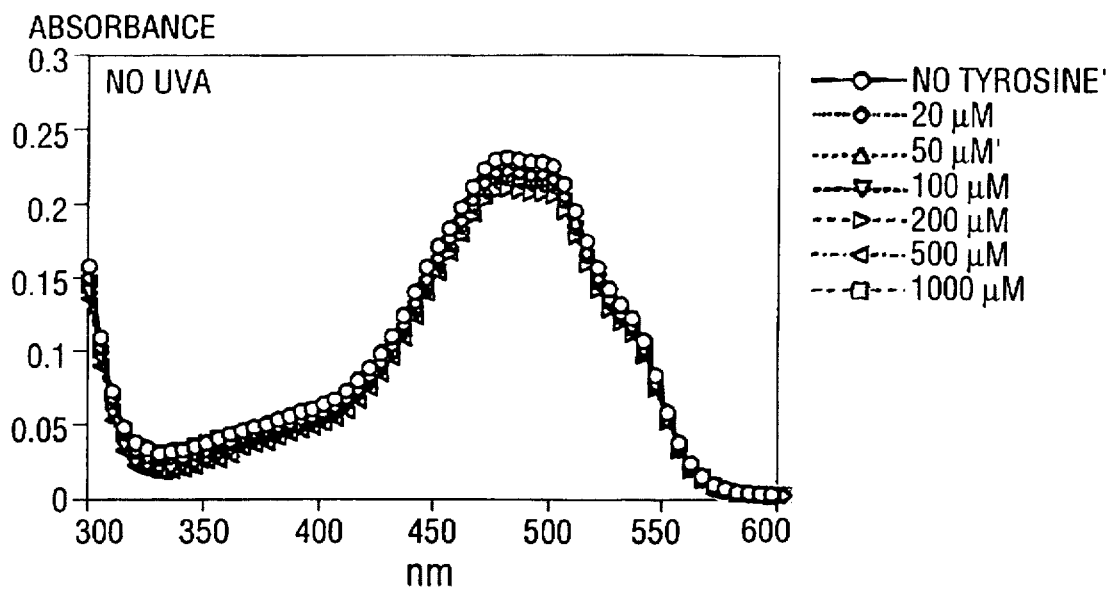
FIGS. 19A–19C show the effect of 0 to 20 minutes of UVA irradiation of 20 µM DOX with 0.5 µM riboflavin and increasing concentrations of tyrosine in PBS (lacking $Ca^{2+}$ and $Mg^{2+}$) on the absorbance spectrum of DOX.
Figure 19B:
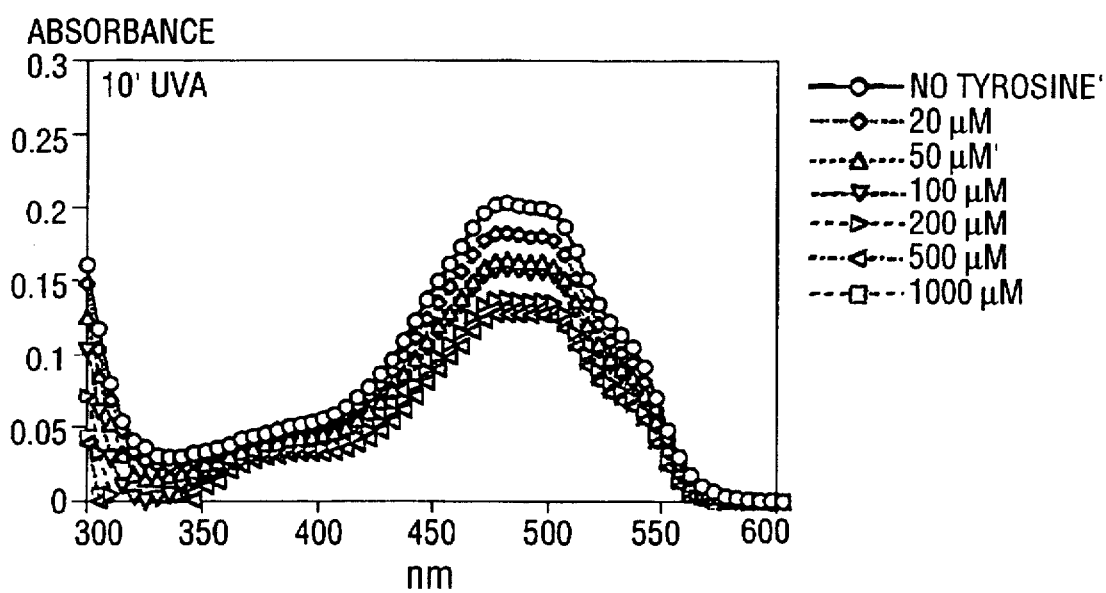
Figure 19C:
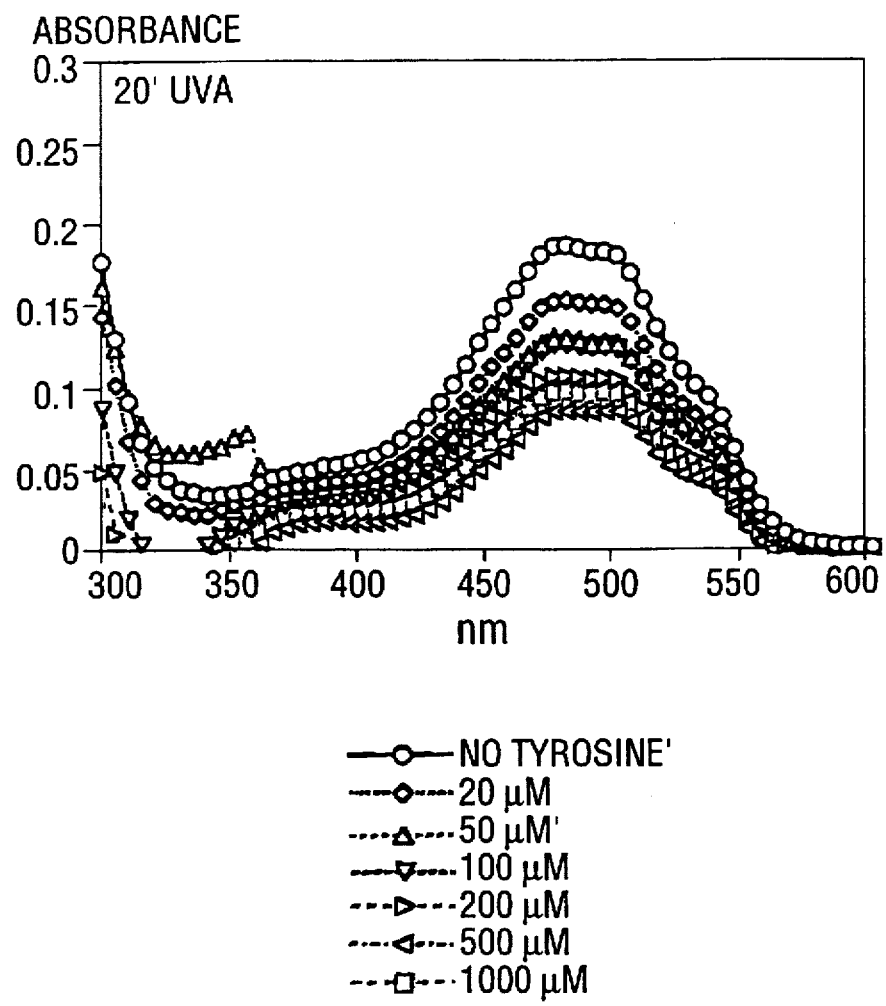

The results shown in FIG. 18 demonstrate that in the presence of 100 μM tyrosine 0.5 μM riboflavin with 20 minutes of UVA irradiation caused a decrease in the absorbance of a 20 μM DOX solution (even in the absence of HEPES). In FIGS. 19A–C, the decrease in the absorbance of DOX exposed to UVA in the presence of 0.5 μM riboflavin was shown to be directly proportional to the concentration of tyrosine. In FIGS. 19A–C, the following symbols represent solutions containing 0, 20, 50, 100, 200, 500 and 1000 μM tyrosine, respectively: ○, ◇, △, ▽, ▸, ◂, and □. FIGS. 19A–C show the absorbance spectrum obtained when a 20 μM DOX solution containing 0.5 μM riboflavin and 0 to 1000 μM tyrosine was either not exposed to UVA irradiation (19A) or exposed to UVA irradiation for 10 (19B) or 20 minutes (19C).

Figure 20A:
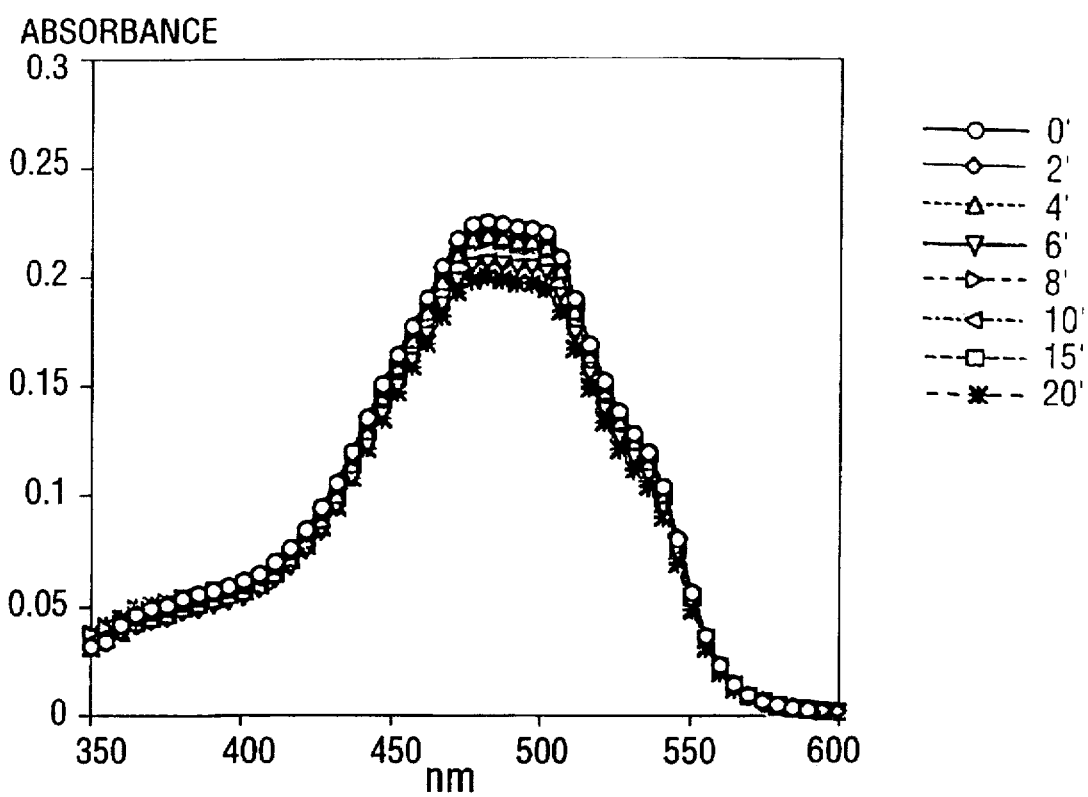
FIGS. 20A and 20B show the effect of UVA irradiation of 20 µM DOX with 100 µM tyrosine and with or without 0.5 µM riboflavin in PBS on the absorbance spectrum of DOX.
Figure 20B:
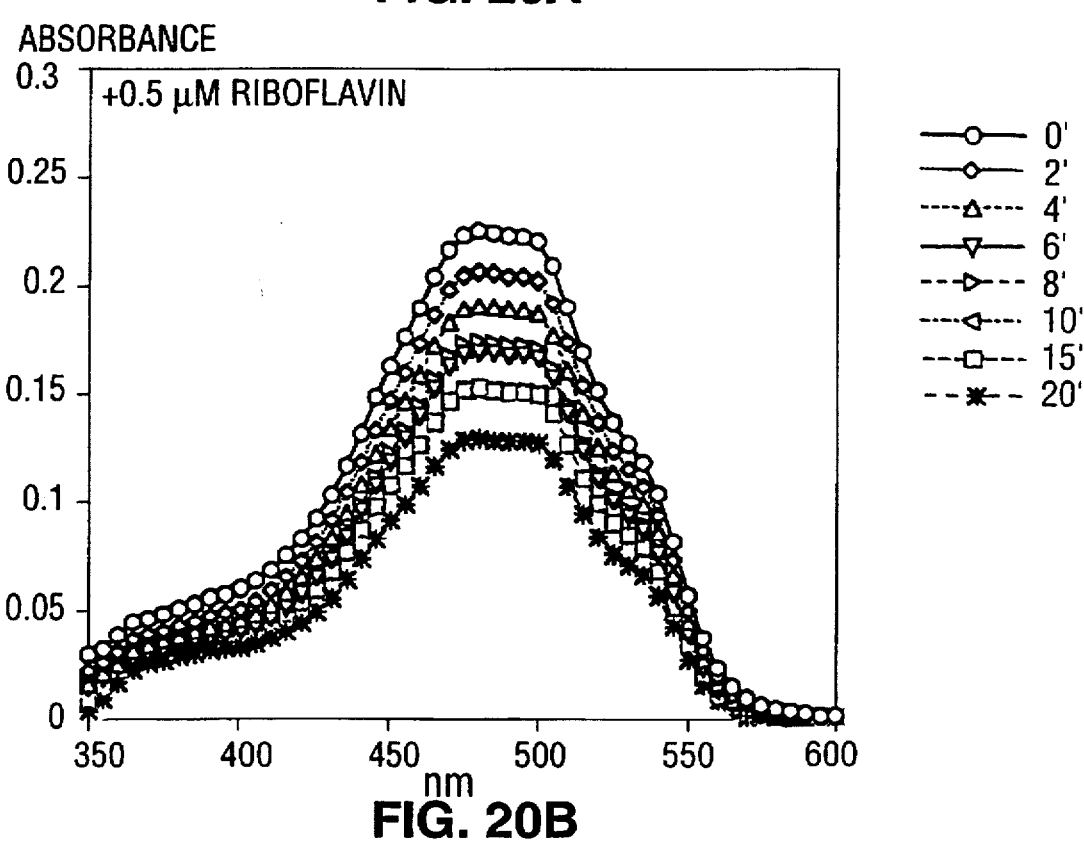

The results shown in FIGS. 20A–B demonstrate that irradiation of a 20 μM DOX solution (in PBS, pH 7.2) containing 100 μM tyrosine has essentially no impact on the absorbance spectrum of DOX but that the addition of 0.5 μM riboflavin to the solution of DOX and tyrosine causes a decrease in the absorbance spectrum of DOX. In FIGS. 20A and B, the following symbols represent 0, 2, 4, 6, 8, 10, 15 and 20 minutes of irradiation, respectively: ○, ◇, △, ▽, ▸, ◂, □, and *. FIG. 20A shows the absorbance spectra obtained by irradiation of a 20 μM DOX solution (in PBS, pH 7.2) containing 100 μM tyrosine. FIG. 20B shows the asorbance spectra obtained by irradiation of a 20 μM DOX solution (in PBS, pH 7.2) containing 100 μM tyrosine and 0.5 μM riboflavin.

Figure 21A:
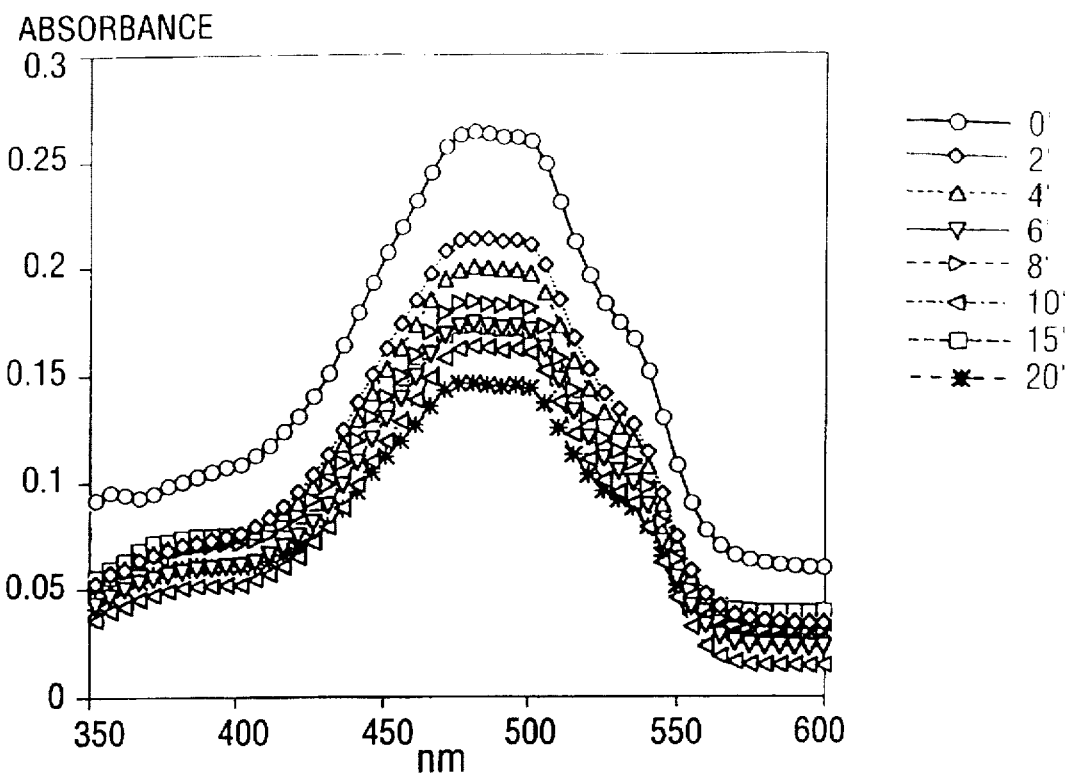
FIGS. 21A and 21B show the effect of UVA irradiation of 20 µM DOX with 0.5 µM riboflavin, 100 µM tyrosine and 0 or 5 mM 1,4-Dimethylpiperazine in PBS on the absorbance spectrum of DOX.
Figure 21B:
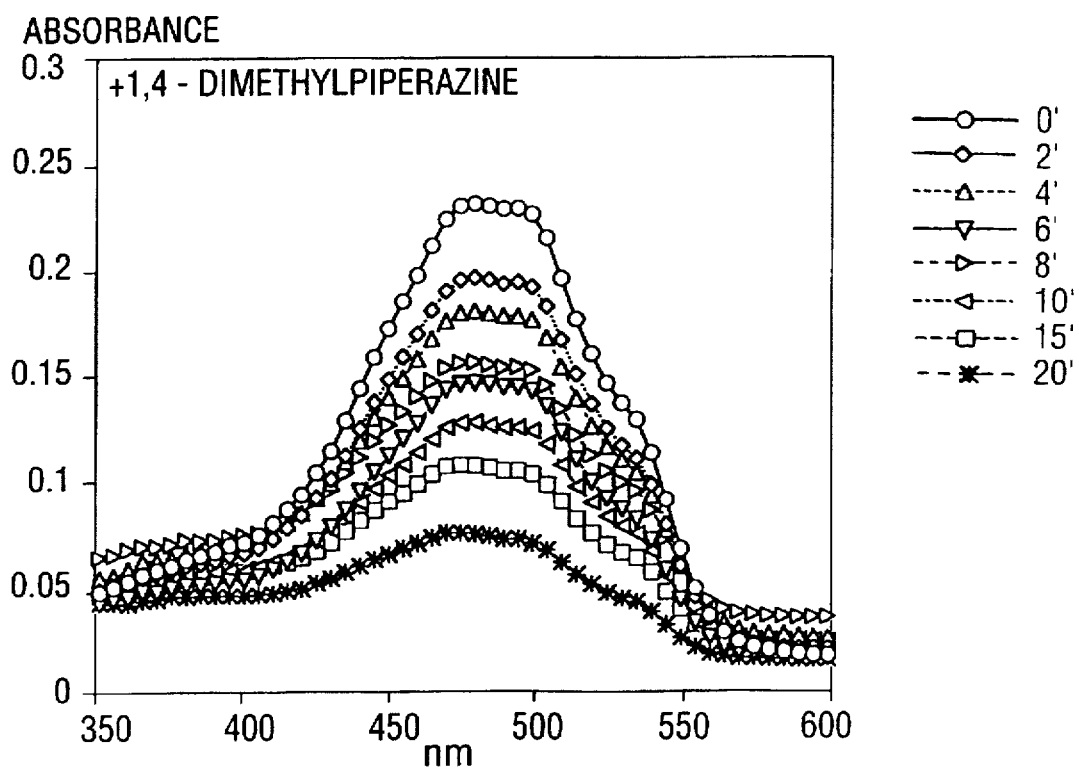

In FIG. 21, the effect of UVA irradiation of solutions containing 20 μM DOX, 0.5 μM riboflavin and 100 μM tyrosine in PBS (pH 7.2) in the presence or absence of 5 mM 1,4-Dimethylpiperazine on the absorbance spectrum of DOX is shown. FIGS. 21A and 21B show the spectrum obtained from solutions containing 20 μM DOX, 0.5 μM riboflavin and 100 μM tyrosine in PBS (pH 7.2) with and without 5 mM 1,4-Dimethylpiperazine, respectively. In FIG. 21, the following symbols represent 0, 2, 4, 6, 8, 10, 15 and 20 minutes of irradiation, respectively: ○, ◇, △, ▽, ▸, ◂, □, and *.

The results shown in FIGS. 15–21 demonstrate that piperazine compounds, such as HEPES, accelerate the riboflavin-mediated photoinactivation of DOX as does DABCO (section a above). However, unlike DABCO, HEPES and other piperazines also enhance the destruction of DOX by the combination of UVA-riboflavin-tyrosine. As shown in FIG. 16, tyrosine (20 to 80 μM) allowed the concentration of riboflavin to be reduced to 0.5 μM (1/40 of the DOX concentration) in the HEPES-containing solution. The results shown in FIG. 17 demonstrate that in the presence of 40 μM tyrosine and 5 mM HEPES, the concentration of riboflavin needed to mediate the destruction of DOX by UVA light was considerably lower than that required for solutions lacking tyrosine and HEPES (FIG. 10). The results shown in FIG. 18 demonstrate that in the presence of 0.5 μM riboflavin and 100 μM tyrosine, much shorter UVA exposure times were required to destroy DOX in the presence of 5 mM HEPES as compared to solutions containing 0.5 mM or no HEPES. In FIG. 19, it was shown that the decrease in absorbance of DOX exposed to UVA in the presence of 0.5 μM riboflavin and tyrosine is directly proportional to the concentration of tyrosine present in the solution. The results shown in FIG. 21 demonstrate that the enhancement of the destruction of DOX by UVA-riboflavin-tyrosine was also achieved using piperazines other than HEPES.

EXAMPLE 7

The Presence Of DABCO Greatly Accelerates The UVA-Riboflavin-Mediated Inactivation Of Doxorubicin The benefit of the formulation of DOX with riboflavin and DABCO for the treatment of drug extravasation (with UVA irradiation) is demonstrated in the following in vitro experiments. In a previous experiment it was found that irradiation periods longer than 10 minutes were required to prevent the growth inhibitory effects of DOX solutions upon P388 cells when the cell suspensions contained 0 to 3 μM DOX and 2 μM riboflavin. The period of irradiation required to reduce or prevent the cytotoxicity of DOX to P388 cells was next examined using solutions containing DOX and 2 μM Riboflavin and 5 mM DABCO as follows.

Using the cell culture assay described in Example 1, P388 cells were exposed to solutions containing 0 to 3 μM DOX, 2 μM riboflavin and 5 mM DABCO in PBS (pH 7.2) and were irradiated for 0 to 90 seconds. The results are shown in FIG. 22.

Figure 22:
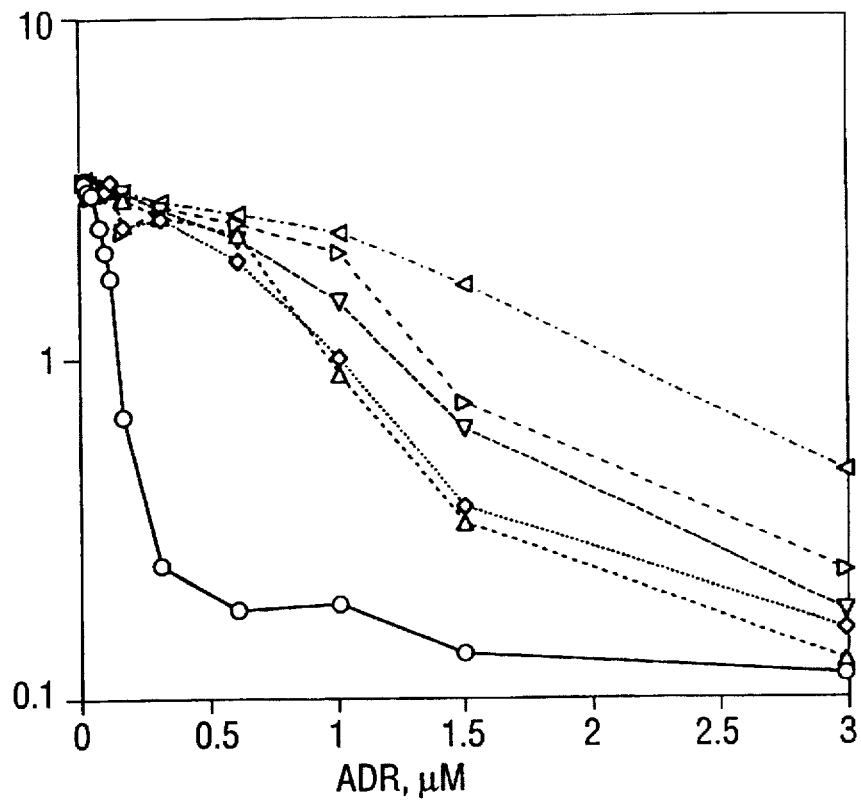
FIG. 22 shows the effect of the length of UVA irradiation of various concentrations of DOX containing 2 µM riboflavin and 5 mM DABCO in PBS on the growth inhibitory effect of DOX on P388 cells.

In FIG. 22, the following symbols represent the density of cells present 4 days after exposure of cells to UVA in the above solutions for 0, 15, 30, 45, 60 and 90 seconds, respectively: ○, ◇, △, ▽, ▸, and ◂. It is noted that the final concentration (i.e., after the addition of the cells) of DOX present in each well is 5-fold lower than the value shown along the x-axis of FIG. 22.

In experiments described above, it was shown that without UVA irradiation, the presence of 2 μm riboflavin and 5 mM DABCO does not reduce the cytotoxicity of DOX to P388 cells. However, the cytotoxicity of the drug was considerably lowered even after 15 seconds of UVA irradiation and after 1.5 minutes of irradiation about 90% of the drug toxicity was abolished (FIG. 22). This experiment shows that the destruction of DOX cytotoxicity by UVA-riboflavin-DABCO can be achieved without causing damage to the cells that are present throughout the UVA exposure.

EXAMPLE 8

Figure 23A:
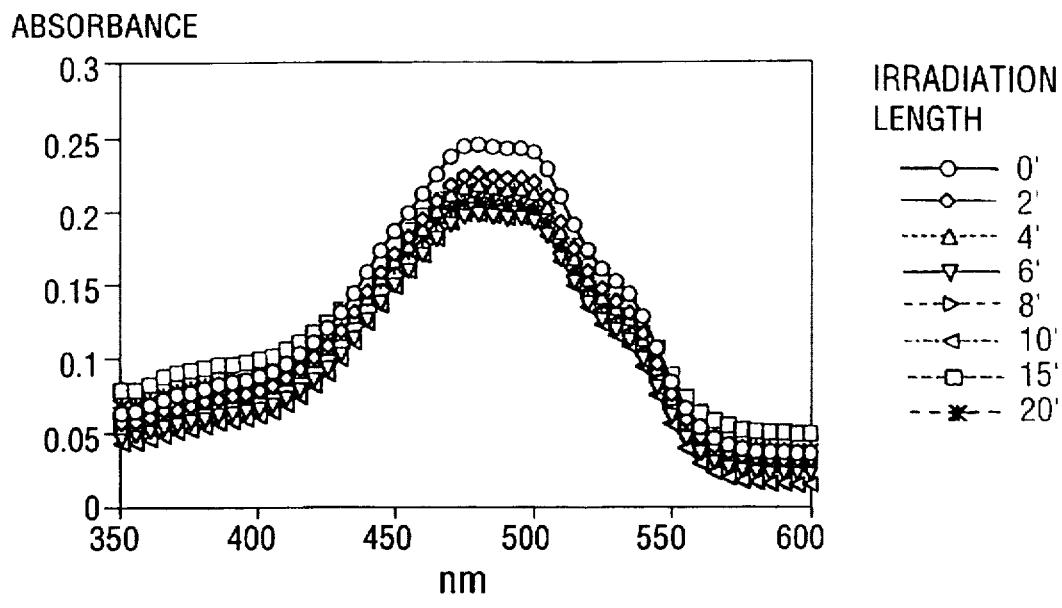
FIGS. 23A–23C show the effect of UVA irradiation of 20 µM DOX with 0.5 µM riboflavin with or without 100 µM tryptophan and with or without 5 mM HEPES in PBS on the absorbance spectrum of DOX.
Figure 23B:
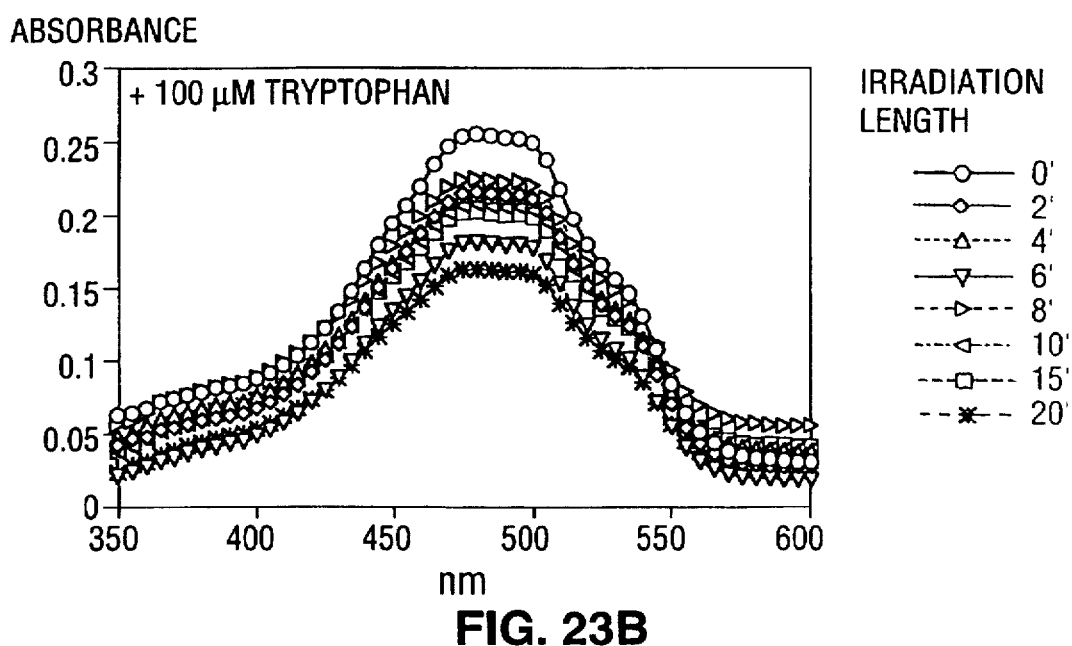
Figure 23C:
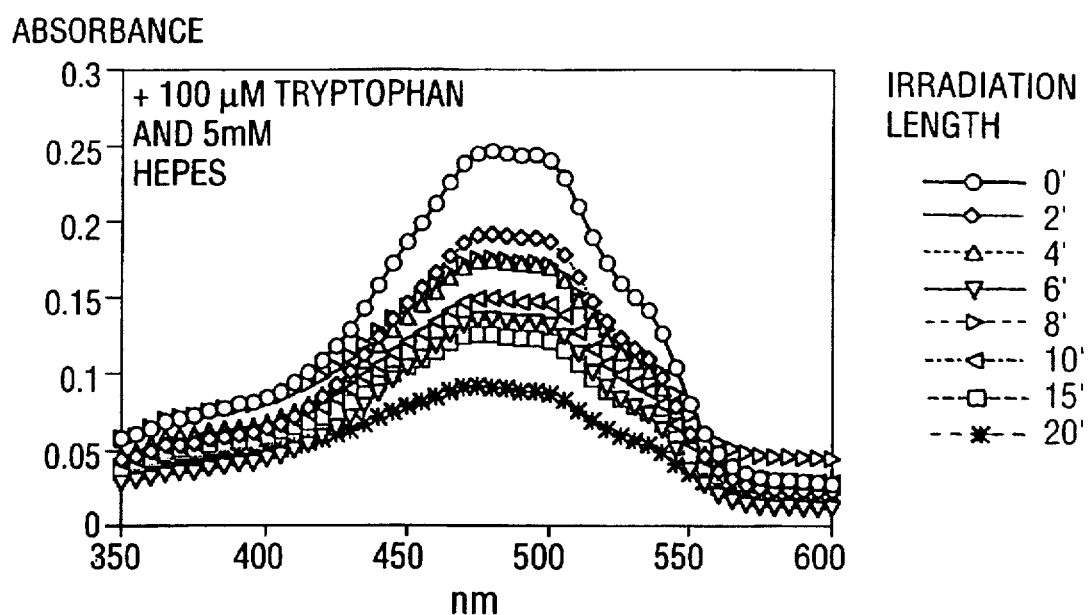

Tryptophan, Methionine, Histidine And EDTA Enhance The Photoinactivation Of Doxorubicin The preceding examples demonstrated that the addition of tyrosine to formulations of DOX and riboflavin accelerated the UVA-riboflavin-mediated destruction of DOX (i.e., tyrosine acts an a photoenhancer). In this example, the ability of tryptophan, methionine, histidine and EDTA to enhance the photoinactivation of DOX was demonstrated.
a) Tryptophan Enhances The Photoinactivation Of Doxorubicin The absorbance spectrum of solutions containing 20 μM DOX, 0.5 μM riboflavin in PBS with and without 100 μM tryptophan and with or without 5 mM HEPES was determined as described in Example 2. The results are shown in FIG. 23. In FIG. 23, the following symbols represent 0, 2, 4, 6, 8, 10, 15 and 20 minutes of irradiation, respectively: ○, ◊, Δ, ∇, ▶, ◀, □, and *. FIG. 23A shows the spectrum obtained from solutions containing 20 μM DOX and 0.5 μM riboflavin in PBS. FIG. 23B shows the spectrum obtained from solutions containing 20 μM DOX and 0.5 μM riboflavin in PBS with 100 μM tryptophan. FIG. 23C shows the spectrum obtained from solutions containing 20 μM DOX and 0.5 μM riboflavin in PBS with 100 μM tryptophan and 5 mM HEPES.

Figure 24:
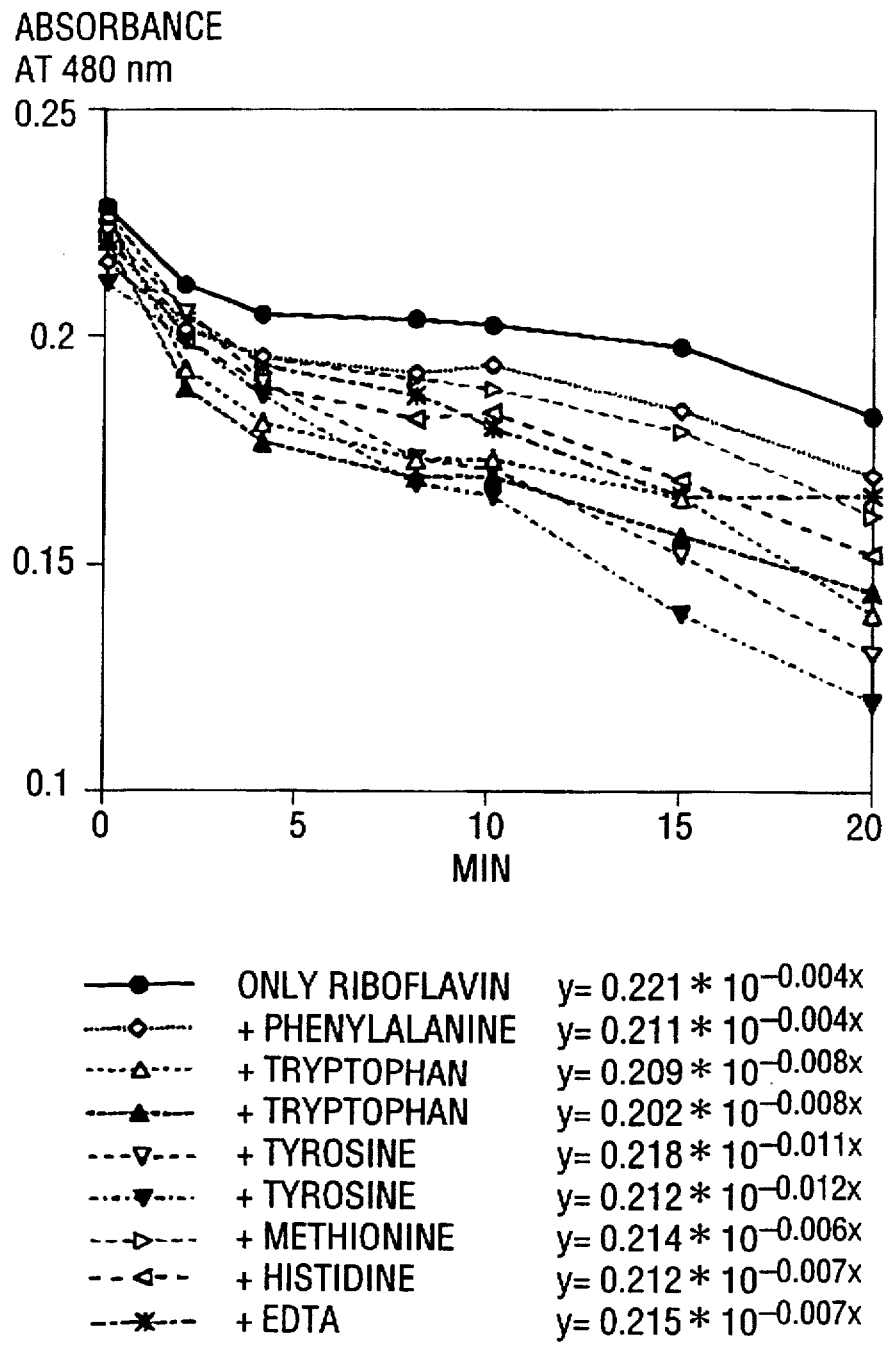
FIG. 24 shows the effect of UVA irradiation of 20 µM DOX with 0.5 µM riboflavin with or without 100 µM phenylalanine, tryptophan, tyrosine, methionine, histidine or EDTA in PBS (without $Ca^{2+}$ and $Mg^{2+}$) on the absorbance spectrum of DOX.

The results shown in FIG. 23 shows that the destruction of DOX in a riboflavin formulation by UVA irradiation was enhanced in the presence of tryptophan (FIG. 23B). This effect was further accelerated by adding HEPES (FIG. 23C).

b) Methionine, Histidine And EDTA Also Enhance The Photoinactivation Of Doxorubicin The absorbance spectrum of solutions containing 20 μM DOX, 0.5 μM riboflavin in PBS (without $Ca^{2+}$ and $Mg^{2+}$, pH 7.2) with and without 100 μM phenylalanine, tryptophan, tyrosine, methionine, histidine or EDTA was determined as described in Example 2. The results are shown in FIG. 24 where the absorbance at 480 nm is plotted against the time of UVA irradiation (0 to 20 minutes). In FIG. 24, the following symbols represent solutions containing only riboflavin, 100 μM phenylalanine, 100 μM tryptophan, 100 μM tyrosine, 100 μM tyrosine, 100 μM methionine, 100 μM histidine, and 100 μM EDTA, respectively: ●, ◊, Δ, ▲, ∇, ▼, ▶, ◀, and *.

The results shown in FIG. 24 demonstrate that the destruction of DOX in a riboflavin formulation by UVA irradiation was enhanced in the presence of tyrosine, tryptophan, histidine, EDTA, and methionine. From the results shown in FIG. 24, it was determined that tyrosine had the greatest photoenhancing effect followed by tryptophan, histidine, EDTA, and methionine. Phenylalanine did not enhance the riboflavin-mediated destruction of DOX to a significant degree.

EXAMPLE 9

Superoxide Dismutase Enhances The Photoinactivation of Doxorubicin

As it has been reported that oxygen radicals may be formed when amino acids are exposed to UVA in the presence of photosensitizers, such as flavins, the effect of adding superoxide dismutase (SOD) to formulations of DOX-riboflavin with or without tyrosine upon the UVA-mediated destruction of DOX was examined.

Figure 25A:
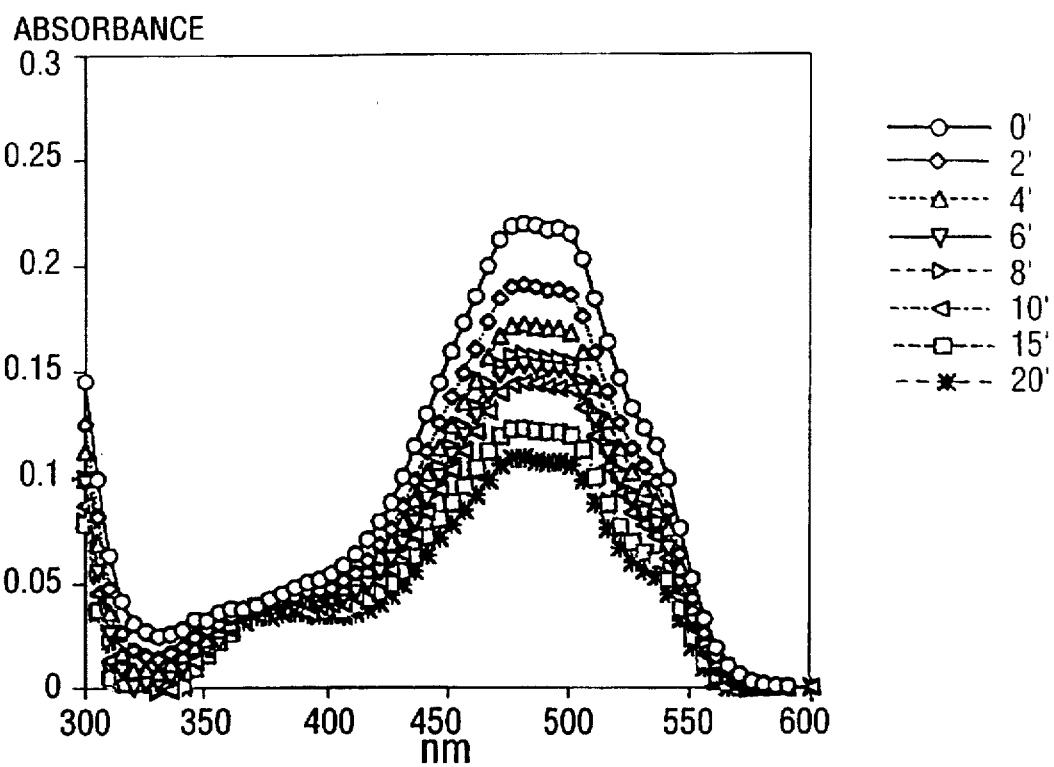
FIGS. 25A and 25B show the effect of UVA irradiation of 20 µM DOX with 0.5 µM riboflavin, 100 µM tyrosine and with or without 300 U/mi SOD in PBS (without $Ca^{2+}$ and $Mg^{2+}$) on the absorbance spectrum of DOX.
Figure 25B:
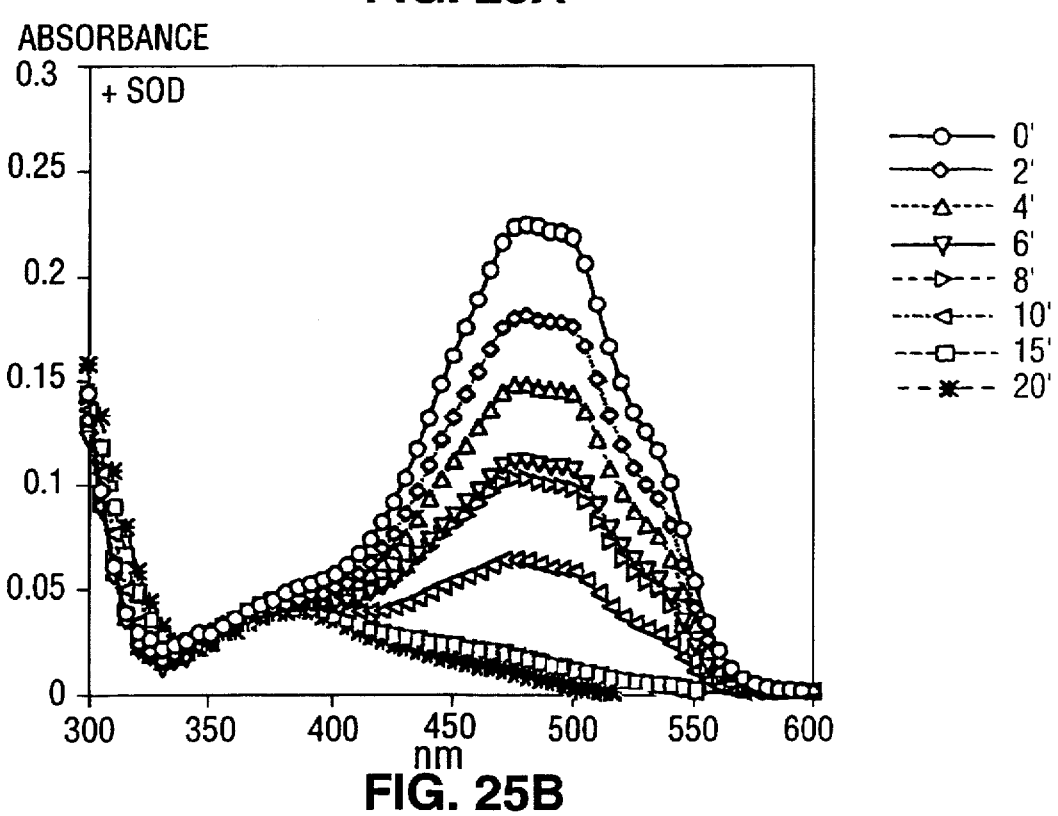

The absorbance spectrum of solutions containing 20 μM DOX, 0.5 μM riboflavin, 100 μM tyrosine in PBS (without $Ca^{2+}$ and $Mg^{2+}$, pH 7.2) with and without 300 U/ml SOD was determined as described in Example 2. The results are shown in FIGS. 25A and 25B. In FIG. 25, the following symbols represent 0, 2, 4, 6, 8, 10, 15 and 20 minutes of irradiation, respectively: ○, ◊, Δ, ∇, ▶, ◀, □, and *. FIG. 25A shows the spectrum obtained from solutions containing 20 μM DOX, 0.5 μM riboflavin and 100 μM tyrosine in PBS. FIG. 25B shows the spectrum obtained from solutions containing 20 μM DOX, 0.5 μM riboflavin and 100 μM tyrosine in PBS with 300 U/ml SOD.

Figure 26A:
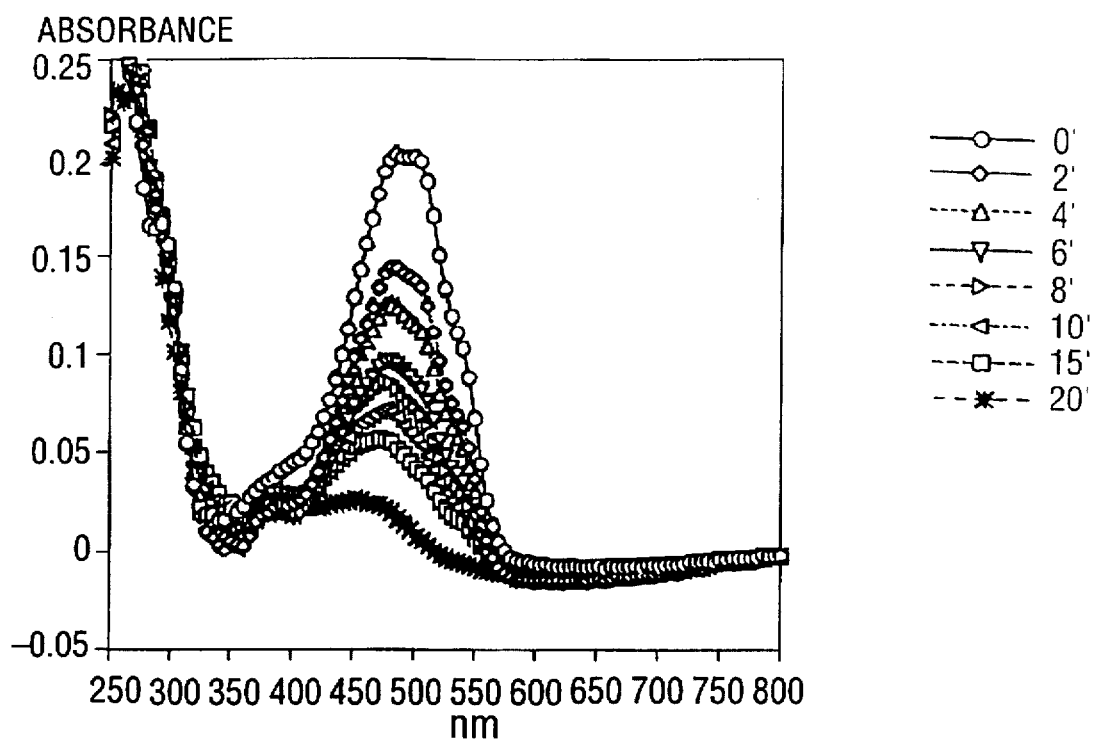
FIGS. 26A and 26B show the effect of UVA irradiation of 20 µM DOX with 20 µM riboflavin and with or without 300 U/ml SOD in PBS (without $Ca^{2+}$ and $Mg^{2+}$) on the absorbance spectrum of DOX.
Figure 26B:
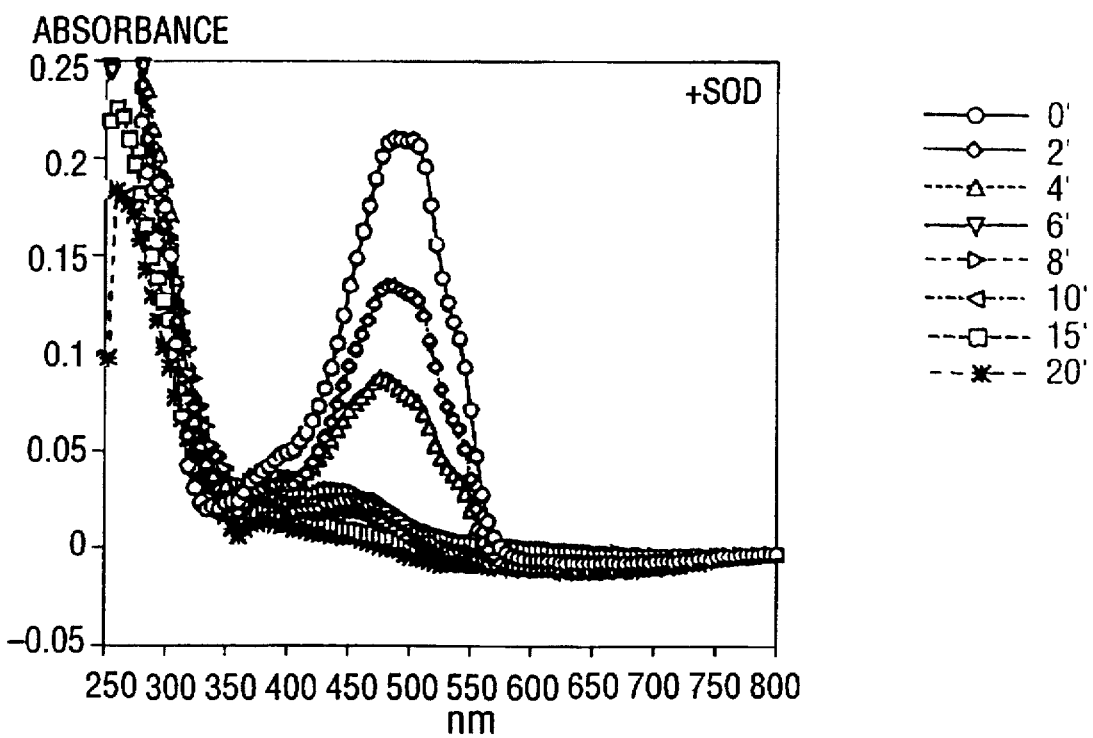

The absorbance spectrum of solutions containing 20 μM DOX and 20 μM riboflavin in PBS (without $Ca^{2+}$ and $Mg^{2+}$, pH 7.2) with and without 300 U/ml SOD was determined as described in Example 2. The results are shown in FIGS. 26A and 26B. In FIG. 26, the following symbols represent 0, 2, 4, 6, 8, 10, 15 and 20 minutes of irradiation, respectively: ○, ◊, Δ, ∇, ▶, ◀, □, and *. FIG. 26A shows the spectrum obtained from solutions containing 20 μM DOX and 20 μM riboflavin in PBS. FIG. 22B shows the spectrum obtained from solutions containing 20 μM DOX and 20 μM riboflavin in PBS with 300 U/ml SOD.

Figure 27A:
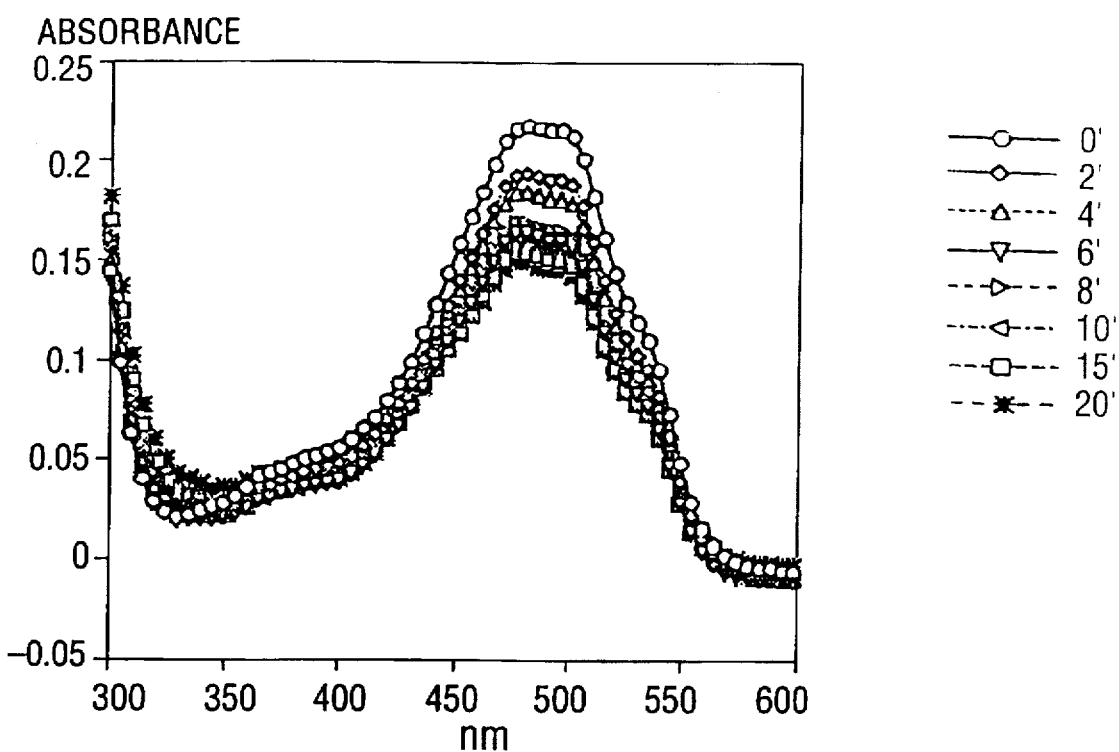
FIGS. 27A and 27B show the effect of UVA irradiation of 20 µM DOX with 2 µM riboflavin and with or without 300 U/ml SOD in PBS (without $Ca^{2+}$ and $Mg^{2+}$) on the absorbance spectrum of DOX.
Figure 27B:
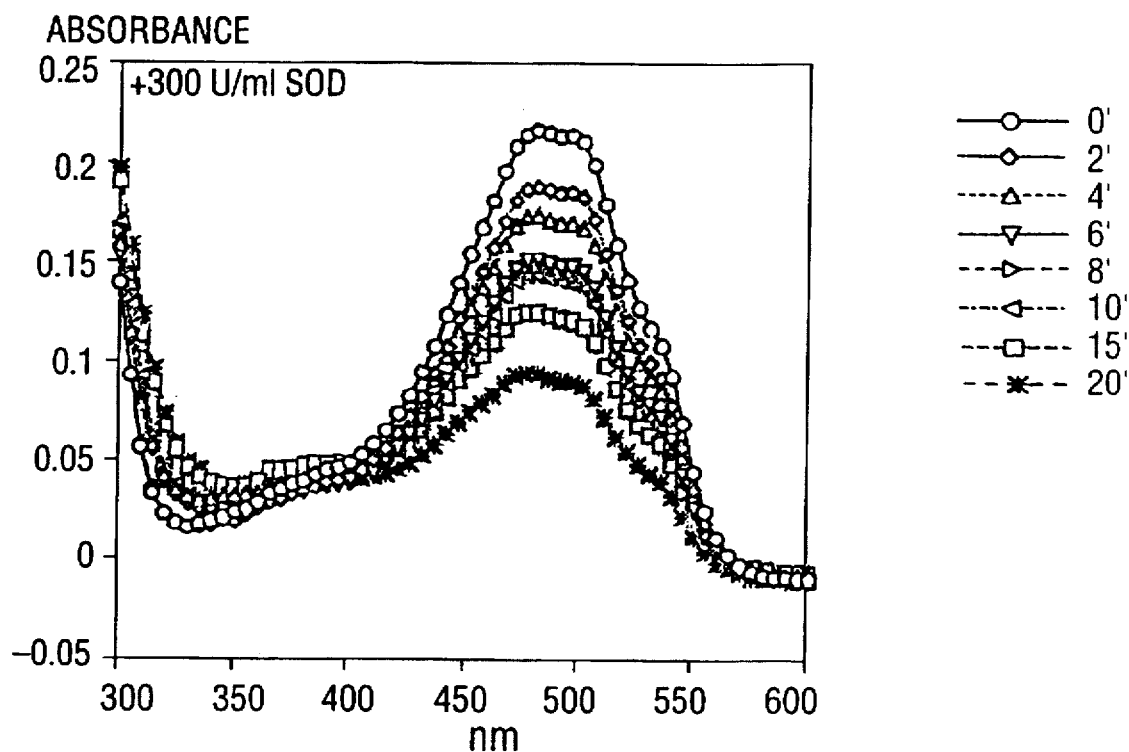
Figure 28A:
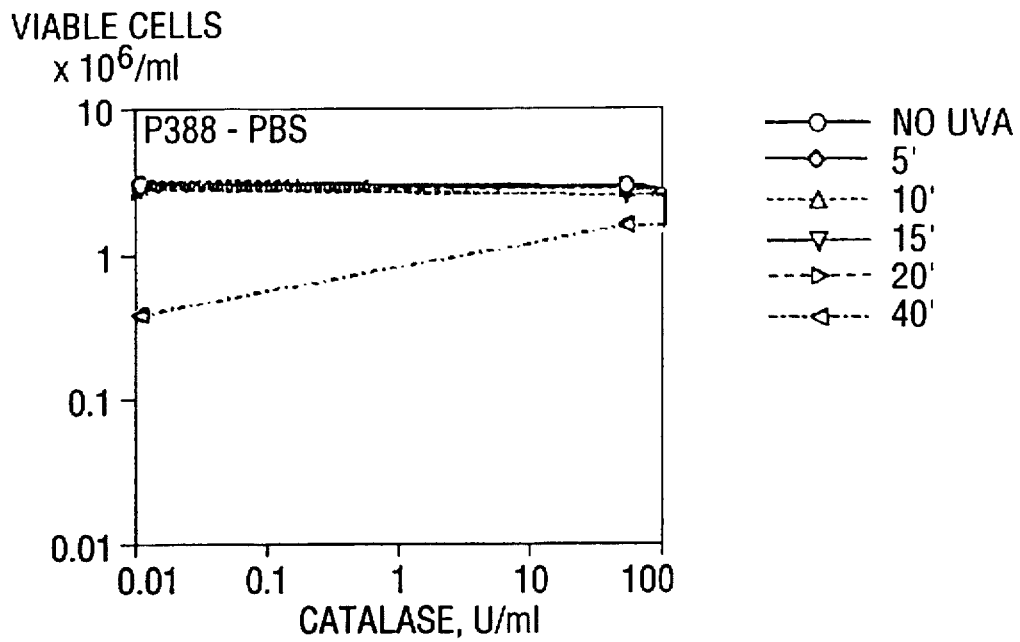
FIGS. 28A–28D show the effect of catalase (21,000 U/ml) on the growth inhibition of P388 cells and P388/ADR cells by UVA irradiation in 0.2 ml of either PBS or RPMI medium 1640.
Figure 28B:
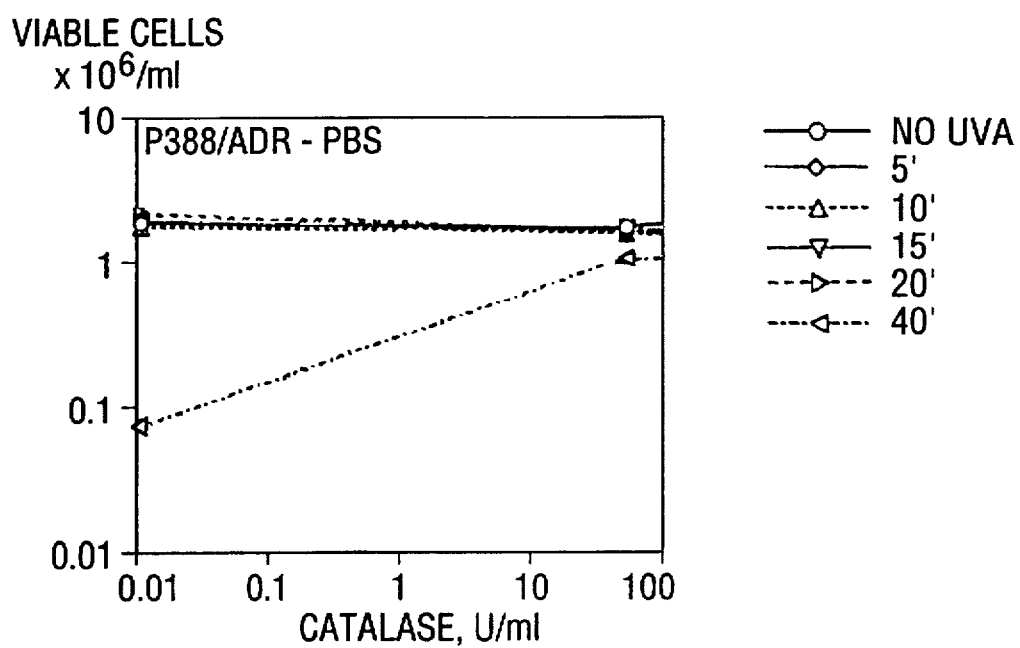
Figure 28C:
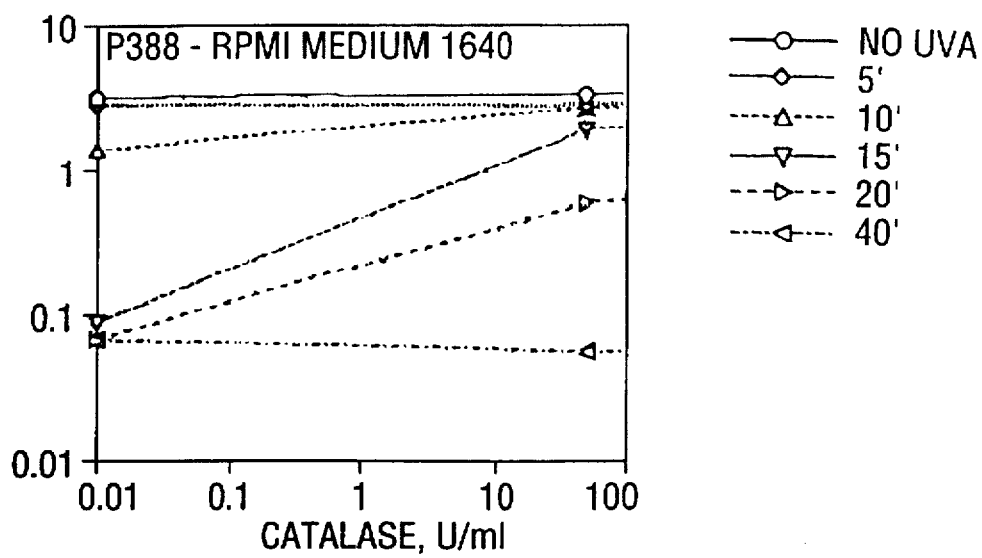
Figure 28D:
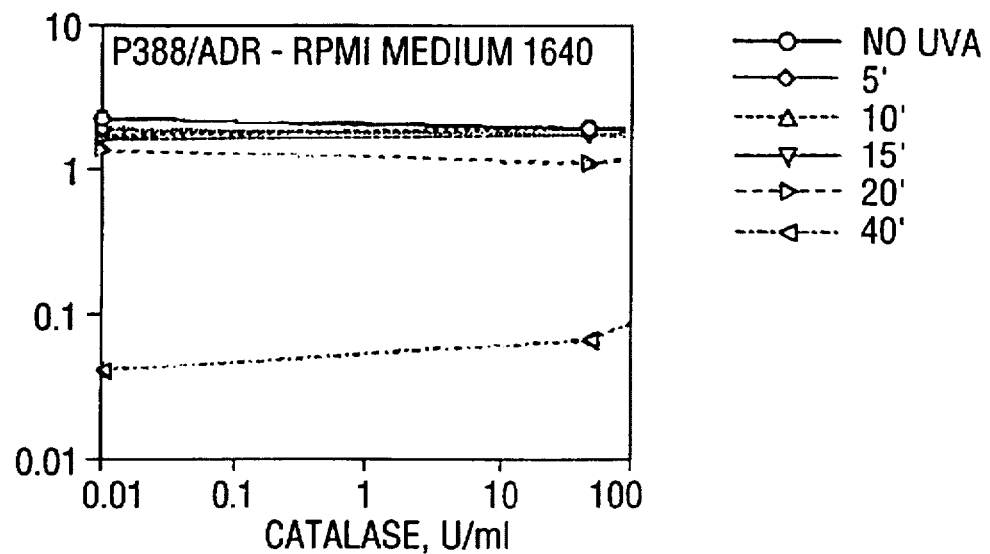

The absorbance spectrum of solutions containing 20 μM DOX and 2 μM riboflavin (i.e., 10-fold less than that used in FIG. 26) in PBS (without $Ca^{2+}$ and $Mg^{2+}$, pH 7.2) with and without 300 U/ml SOD was next determined as described in Example 2. The results are shown in FIGS. 27A and 27B. In FIG. 27, the following symbols represent 0, 2, 4, 6, 8, 10, 15 and 20 minutes of irradiation, respectively: ○, ◊, Δ, ∇, ▶, ◀, □, and *. FIG. 27A shows the spectrum obtained from solutions containing 20 μM DOX and 2 μM riboflavin in PBS. FIG. 27B shows the spectrum obtained from solutions containing 20 μM DOX and 2 μM riboflavin in PBS with 300 U/ml SOD.

The results shown in FIGS. 25–27 demonstrate that superoxide dismutase acts as a photoenhancer and accelerates the rate at which DOX is inactivated by either riboflavin or riboflavin-tyrosine. Because oxygen radicals may be generated during the photoinactivation of DOX formulations containing flavins and amino acid enhancers (e.g., tyrosine), the addition of SOD to the DOX formulation serves the dual purpose of protecting the UVA irradiated tissue from free radicals as well as enhancing the destruction of DOX.

EXAMPLE 10

Catalase Protects Cells From The Effects of UVA Irradiation

It has been reported that hydrogen peroxide may be formed when amino acids are exposed to UVA in the presence of photosensitizers, such as flavins (Brawley et al., supra). Therefore, the addition of agents capable of degrading hydrogen peroxide to DOX formulations containing flavins and/or amino acids would serve to protect tissue exposed to UVA from damage due to the production of hydrogen peroxide. In this example the ability of catalase to protect cells from damage caused by protracted UVA irradiation was examined.

P388 cells and P388/ADR cells in either PBS or RPMI 1640 medium containing 0.01 to 100 U/ml catalase were exposed to UVA light for increasing periods of time as described in Example 1b with the exception that $1 \times 10^5$ cells were placed in the 0.2 ml solution (PBS or RPMI with catalase) prior to irradiation. After irradiation, 0.8 ml complete culture medium was added to each well and the cell density was measured after 4 days of culture. The P388/ADR cell line is a subclone of the P388 cell line which was selected for multidrug resistance. The results are shown in FIGS. 28A–D (the number of viable cells×$10^6$/ml is plotted against the concentration of catalase).

In FIG. 28, the following symbols represent 0, 5, 10, 15, 20 and 40 minutes of irradiation, respectively: ○, ◊, Δ, ∇, ▶, and ◀. FIGS. 28A and 28B show the results obtained using P388 and P388/ADR cells in PBS, respectively. FIGS. 28C and 28D show the results obtained using P388 and P388/ADR cells in RPMI 1640, respectively.

The results shown in FIG. 28 demonstrate that UVA irradiation has a greater growth inhibitory effect upon cells which are irradiation in RPMI 1640, which contains flavins and amino acids, than upon cells which are irradiated in PBS. The addition of catalase to cell suspensions containing either PBS or RPMI 1640, protected the cells from damage (as judged by inhibition of growth) caused by protracted UVA irradiation. These results demonstrate that the addition of catalase to formulations of DOX containing flavins and/or amino acid photoenhancers protects UVA irradiated cells from damage due to the production of oxygen radicals.

Figure 29:
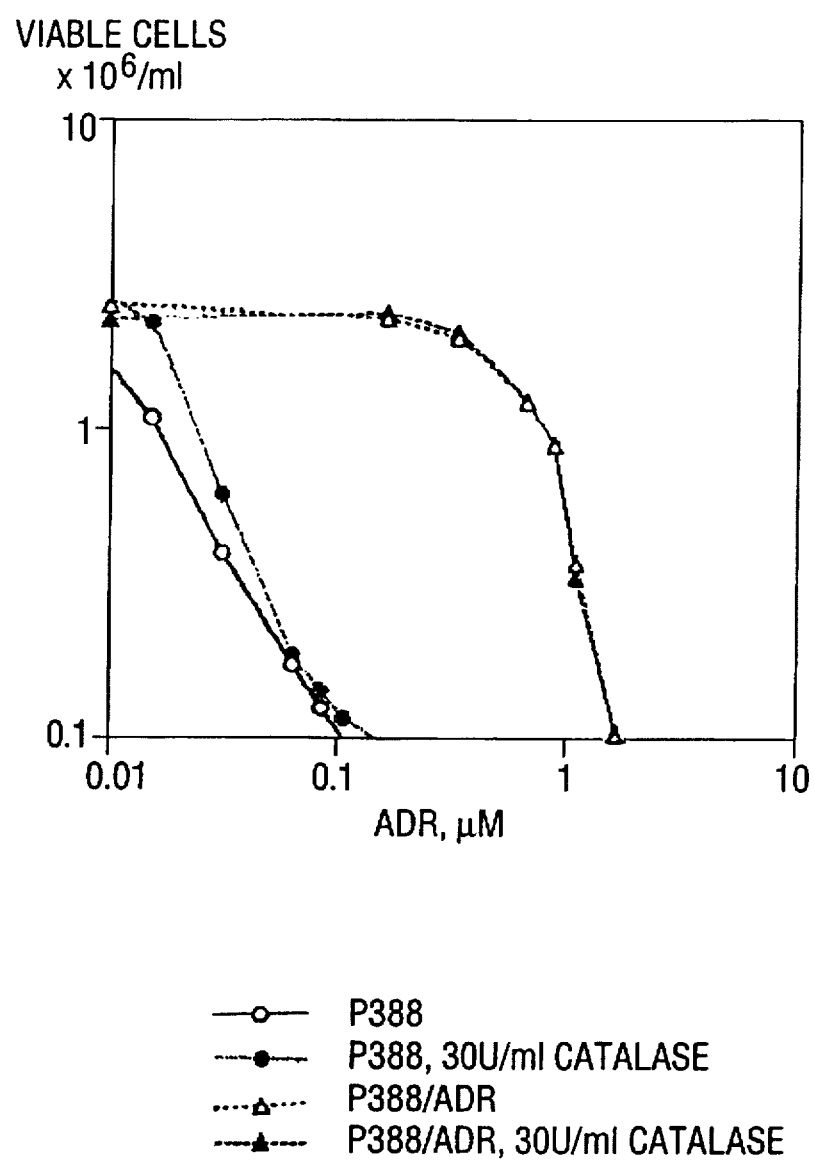
FIG. 29 shows the effect of 30 U/ml catalase (21,000 U/ml) on the growth inhibitory effect of DOX on P388 cells and P388/ADR cells.

In FIG. 29, it is shown that in the absence of UVA irradiation, catalase does not interfere with the growth inhibitory effect of DOX upon either the P388 or P388/ADR cell lines. For the results shown in FIG. 29, solutions containing increasing amounts of DOX in 0.2 ml PBS with or without 30 U/ml catalase were irradiated and then $1 \times 10^5$ viable cells in 0.8 ml complete growth medium were added to each well as described in Ex. 1. After 4 days in culture, the cell density was measured. In FIG. 29, the number of viable cells ($\times 10^6$/ml) is plotted against the concentration of DOX present in the PBS solution during irradiation. The following symbols represent P388 cells grown in the presence of irradiated DOX solutions lacking catalase, P388/ADR cells grown in the presence of irradiated DOX solutions lacking catalase, P388 cells grown in the presence of irradiated DOX solutions containing 30 U/ml catalase and P388/ADR cells grown in the presence of irradiated DOX solutions containing 30 U/ml catalase, respectively: ○, △, ●, and ▲.

The above results demonstrate that catalase has no effect upon the growth inhibitory effect of DOX; however, these results show that catalase can protect cells from damage caused by protracted irradiation with UVA.

EXAMPLE 11

Formulation Of Solutions Containing Anthracyclines And Flavins

The preceding examples demonstrate that DOX in solution can be chemically changed (loss of growth inhibitory activity and absorbance spectrum) by long ultraviolet light in intensities that are used clinically (e.g., in the treatment of patients with psoriasis). To obtain this effect DOX (and other anthracycline drugs and/or other antineoplastic agents such as mithramycin, mitomycin C, taxol or Vinca alkaloids) are formulated with flavins (such as riboflavin, FMN, FAD) at molar quantity ratios of 1:80 to 1:1 flavin:DOX and the following enhancers:

a) 1:50 to 1:500 DOX:DABCO molar ratio (or other tertiary aliphatic amines such as triethylamine); or b) 1:50 to 1:500 DOX:HEPES molar ratio (or other piperazines such as 1,4-dimethylpiperazine); or c) 1:1 to 1:6 DOX:tyrosine or tryptophan molar ratio (histidine, methionine or EDTA may be employed in place of tyrosine or tryptophan) and 1:50 to 1:500 DOX:piperazine (e.g., HEPES or 1,4-Dimethylpiperazine).

It has been reported that hydrogen peroxide and oxygen radicals may be formed when amino acids are exposed to UVA in the presence of photosensitizers. Accordingly, catalase (about 100 U/ml) and/or superoxide dismutase (50–300 U/ml) may be added to the above formulations. Superoxide dismutase (shown herein to act as a photoenhancer) converts superoxide radicals into hydrogen peroxide. Catalase converts hydrogen peroxide into $H_2O$ and molecular oxygen. Recombinant human CuZn superoxide dismutase is available from Bio-Technology General Corp. (Iselin, N.J.).

These formulations of DOX, while not interfering with the systemic cytotoxic activity of the drug, allows the destruction of DOX locally by clinically permissible quantities of long ultraviolet light (e.g., 3 to 5 $mW/Cm^2$ for up to 20 minutes) will be delivered to the injection area once it is realized that extravasation has occurred (determined by swelling, pain and tissue staining by the drug).

EXAMPLE 12

Established murine and pig models are employed to demonstrate the prevention and/or treatment of DOX induced extravasation ulcers using the formulations and methods of the present invention.

a) Murine Model

An established murine model which allows the quantitation of DOX skin toxicity is used to demonstrate the effectiveness of the formulations and methods of |Dorr et al. (1980) J. Pharmacol. Methods 4:321 and Dorr et al. (1980) Cancer Chemother. Pharmacol. 5:17|.

Dorsal hair is removed (3×3 cm area) from adult BALB/c mice (~25 g) (Jackson Laboratories, Bar Harbor, Me.) 24 hours prior to the ID injection of DOX solutions using a topical depilatory agent (e.g., Neet lotion). Animals are divided into groups of four each and are housed together for the duration of the experiment. Positive control injections contain 0.5 and 0.05 mg DOX diluted into 0.05 ml sterile normal (0.9%) saline (without preservatives); this dose corresponds to approximately 70 and 7 $mg/m^2$, respectively. Negative control injections comprise 0.05 ml sterile 0.9% saline (without preservatives). Test or experimental injections contain the DOX formulations described in Example 11.

Following ID injection, the injection area is exposed to UVA light using an suitable lamp assembly (e.g., Vilber-Lourmat lamps containing blacklight blue tubes T-40LN (Cole-Parmer Instrument Co., Niles, Ill.)| to permit the delivery of 3 to 5 $mW/cm^2$ for 0 to 20 minutes. The injected area is exposed to UVA light at 0 (i.e., immediately after injection), 1, 3 and 6 hours after injection. Following injection and exposure to UVA, all skin lesions are evaluated daily by measurement of the widest perpendicular width of ulceration, erythema and induration of the skin lesions are measured daily using a micrometer. The ulceration area×day ($cm^2$×days) is calculated to quantitate an area under the toxicity-time curve (AUC) or the sum of total ulceration over time. In this mouse model, it has been shown that the above toxicity parameters increase in a DOX dose-dependent manner with respect to both the total area of the lesion ($cm^2$/day) and the peak toxicity level ($cm^2$) and the duration of toxicity (days). Statistical analyses (intergroup) may be conducted using standard techniques (e.g., Student's t-test or Student-Newman-Keuls multiple range test).

Desirable DOX formulations and UVA exposure levels are those which reduce or eliminate the DOX-induced lesions as compared to the positive control |i.e., they result in a statistically lower level of toxicity as compared to the control DOX solution (i.e., lacking either a PIC or a photoenhancer)|.

b) Pig Model

An established swine model which allows the quantitation of DOX skin toxicity is used to demonstrate the effectiveness of the formulations and methods of the present invention for the treatment of injury caused by the extravasation of DOX |Averbuch et al. (1986) J. Clin. Oncol. 4:88|. In this swine model, it has been shown that DOX produces a predictable and reproducible skin ulceration and the total toxicity (AUC) increases in a DOX dose-dependent manner (Averbuch et al., supra).

Inbred weanling miniature white swine (~12 kg) (Veterinary Resources Branch, National Institutes of Health, Bethesda, Md.) are anesthetized using standard techniques (e.g., an initial IM injection of ketamine, xylazine and atropine followed by intubation and administration of nitrous oxide, halothane and oxygen gas or administration of pentobarbital). DOX solutions are administered ID using a 25-gauge needle inserted approximately 4–5 mm into the skin. Each pig may receive multiple injections (up to 6 sites per midlateral aspect of each side) spaced 4–5 cm apart.

Positive control injections contain 1.0 to 2.0 mg DOX; a stock solution containing 2.0 mg/ml DOX in sterile 0.9% saline (may also contain lactose) is used for the injections. Negative control injections comprise 0.5 to 1.0 ml sterile 0.9% saline. Test or experimental injections contain the DOX formulations described in Example 11.

Following ID injection, the injection area is exposed to various doses of UVA light for various lengths of time as described above for the mouse model. Following injection and exposure to UVA, all skin lesions are measured using calipers 3 times per week for 2 weeks, followed by weekly measurements. Each animal is observed for an 8 week period. Areas of induration and skin ulceration are estimated by the product of the cross-perpendicular diameters. The total toxicity of the DOX-induced ulceration is calculated as the AUC in $mm^2 \times days$. Statistical analyses (intergroup) may be conducted using standard techniques (e.g., Student's t-test or Student-Newman-Keuls multiple range test).

Desirable DOX formulations and UVA exposure levels are those which reduce or eliminate the DOX-induced lesions as compared to the positive control [i.e., they result in a statistically lower level of toxicity as compared to the control DOX solution (i.e., lacking either a PIC or a photoenhancer)].

From the above, it is evident that the anthracycline formulations of the present invention comprising a photosensitizer (e.g., a flavin), a photoenhancer (e.g., DABCO, piperazines, tyrosine, tryptophan, superoxide dismutase) and optionally catalase provide an improvement to present anthracycline formulations. These improved anthracycline formulations allow the prevention and/or treatment of injury due to extravasation of anthracyclines. In particular, these formulations when employed with the methods described herein (i.e., exposure to UVA) allow for the destruction of extravasated anthracyclines thereby preventing injury to the tissue surrounding the injection site.

I claim:

1. A method of treatment of extravasation injury, comprising:
   a) providing:
      i) a subject; and
      ii) a formulation comprising a photoinactivation inducing compound; and
   b) administering intravenously said formulation to said subject; and
   c) exposing the intravenous administration site to UVA light.

2. The method of claim 1, wherein said formulation further comprises a vesicant chemotherapeutic.

3. The method of claim 2, wherein said chemotherapeutic is an antineoplastic drug.

4. The method of claim 3 wherein said antineoplastic is a Vinca alkaloid.

5. The method of claim 3, wherein said antineoplastic drug is an anthracycline.

6. The method of claim 5, wherein said anthracycline is doxorubicin.

7. The method of claim 1, wherein said photoinactivation inducing compound is a flavin.

8. The method of claim 7, wherein said flavin is selected from the group consisting of riboflavin, flavin mononucleotide, and flavin adenine dinucleotide.

9. The method of claim 1, wherein said formulation further comprises at least one photoenhancer compound.

10. The method of claim 9, wherein said photoenhancer compound is a tertiary aliphatic amine.

11. The method of claim 10, wherein said tertiary aliphatic amine is 1,4-diazabicyclo(2.2.2)octane.

12. The method of claim 9, wherein said photoenhancer compound is a piperazine.

13. The method of claim 12, wherein said piperazine is selected from the group consisting of N-2-hydroxyethylpiperazine-N'-2-ethanesulfonic acid and 1,4-dimethylpiperazine.

14. The method of claim 9, wherein said photoenhancer compound is selected from the group consisting of tyrosine, tryptophan, histidine, methionine, superoxide dismutase and ethylenediaminetetraacetic acid.

15. The method of claim 1, wherein said formulation further comprises catalase.

16. A composition comprising a serum-free saline solution comprising a vesicant chemotherapeutic, a photoinactivation inducing compound, and catalase.

17. A composition comprising vesicant chemotherapeutic, a photoinactivation inducing compound and at least one photoenhancer compound.

18. The composition of claim 17, wherein said vesicant chemotherapeutic is an antineoplastic drug.

19. The composition of claim 18, wherein said antineoplastic drug is an anthracycline.

20. The composition of claim 19, wherein said anthracycline is doxorubicin.

21. The composition of claim 17, wherein said photoinactivation inducing compound is a flavin.

22. The composition of claim 21, wherein said flavin is selected from the group consisting of riboflavin, flavin mononucleotide, and flavin adenine dinucleotide.

23. The composition of claim 17, wherein said photoenhancer compound is a tertiary aliphatic amine.

24. The composition of claim 23, wherein said tertiary aliphatic amine is 1,4-diazabicyclo(2.2.2)octane.

25. The composition of claim 17, wherein said photoenhancer compound is a piperazine.

26. The composition of claim 25, wherein said piperazine is selected from the group consisting of N-2-hydroxyethylpiperazine-N'-2-ethanesulfonic acid and 1,4-dimethylpiperazine.

27. The composition of claim 17, wherein said photoenhancer compound is selected from the group consisting of tyrosine, tryptophan, histidine, methionine, superoxide dismutase and ethylenediaminetetraacetic acid.

28. The composition of claim 17, further comprising catalase.

29. A method for preventing extravasation injury, comprising:
   a) providing:
      i) a subject; and
      ii) a formulation comprising a photoinactivation inducing compound comprising a flavin and a vesicant chemotherapeutic; and
   b) administering intravenously said formulation to said subject; and
   c) exposing the intravenous administration site to UVA light.

30. The method of claim 29, wherein said chemotherapeutic is an antineoplastic drug.

31. The method of claim 30, wherein said antineoplastic drug is an anthracycline.

32. The method of claim 31, wherein said anthracycline is doxorubicin.

33. The method of claim 30, wherein said antineoplastic is a Vinca alkaloid.

34. The method of claim 29, wherein said flavin is selected from the group consisting of riboflavin, flavin mononucleotide, and flavin adenine dinucleotide.

35. The method of claim 34, wherein said formulation further comprises at least one photoenhancer compound.

36. The method of claim 35, wherein said photoenhancer compound is selected from the group consisting of tyrosine, tryptophan, histidine, methionine, superoxide dismutase and ethylenediaminetetraacetic acid.

37. The method of claim 35, wherein said photoenhancer compound is a tertiary aliphatic amine.

38. The method of claim 37, wherein said tertiary aliphatic amine is 1,4-diazabicyclo(2.2.2)octane.

39. The method of claim 37, wherein said photoenhancer compound is a piperazine.

40. The method of claim 39, wherein said piperazine is selected from the group consisting of N-2-hydroxyethylpiperazine-N'-2-ethanesulfonic acid and 1,4-dimethylpiperazine.

41. The method of claim 29, wherein said formulation further comprises catalase.

* * * * *